US007834171B2

(12) United States Patent
Leake et al.

(10) Patent No.: US 7,834,171 B2
(45) Date of Patent: *Nov. 16, 2010

(54) MODIFIED POLYNUCLEOTIDES FOR REDUCING OFF-TARGET EFFECTS IN RNA INTERFERENCE

(75) Inventors: Devin Leake, Denver, CO (US); Angela R Reynolds, Conifer, CO (US); Anastasia Khvorova, Boulder, CO (US); William Marshall, Boulder, CO (US)

(73) Assignee: Dharmacon, Inc., Lafayette, CO (US)

( * ) Notice: Subject to any disclaimer, the term of this patent is extended or adjusted under 35 U.S.C. 154(b) by 303 days.

This patent is subject to a terminal disclaimer.

(21) Appl. No.: 11/857,732

(22) Filed: Sep. 19, 2007

(65) Prior Publication Data

US 2008/0242851 A1 Oct. 2, 2008

Related U.S. Application Data

(63) Continuation of application No. 11/019,831, filed on Dec. 22, 2004, now Pat. No. 7,595,387, which is a continuation-in-part of application No. 10/551,350, filed as application No. PCT/US2004/010343 on Apr. 1, 2004, and a continuation of application No. 10/613,077, filed on Jul. 1, 2003, now abandoned, which is a continuation-in-part of application No. 10/406,908, filed on Apr. 2, 2003, now abandoned.

(60) Provisional application No. 60/630,228, filed on Nov. 22, 2004, provisional application No. 60/543,640, filed on Feb. 10, 2004, provisional application No. 60/543,661, filed on Feb. 10, 2004, provisional application No. 60/542,646, filed on Feb. 6, 2004, provisional application No. 60/542,668, filed on Feb. 6, 2004.

(51) Int. Cl.
C07H 21/04 (2006.01)
A61K 48/00 (2006.01)

(52) U.S. Cl. .................. 536/24.5; 536/24.31; 536/24.1; 514/44; 435/6; 435/325; 435/375

(58) Field of Classification Search ....................... None
See application file for complete search history.

(56) References Cited

U.S. PATENT DOCUMENTS

| | | |
|---|---|---|
| 4,924,624 A | 5/1990 | Suhadolnik et al. |
| 5,023,243 A | 6/1991 | Tullis |
| 5,138,045 A | 8/1992 | Cook et al. |
| 5,151,510 A | 9/1992 | Stec et al. |
| 5,214,136 A | 5/1993 | Lin et al. |
| 5,264,562 A | 11/1993 | Matteucci |
| 5,264,564 A | 11/1993 | Matteucci |
| 5,286,717 A | 2/1994 | Cohen et al. |
| 5,399,676 A | 3/1995 | Froehler |
| 5,414,077 A | 5/1995 | Lin et al. |
| 5,434,257 A | 7/1995 | Matteucci et al. |
| 5,457,191 A | 10/1995 | Cook et al. |
| 5,457,527 A | 10/1995 | Manns |
| 5,459,255 A | 10/1995 | Cook et al. |
| 5,484,908 A | 1/1996 | Froehler et al. |
| 5,487,872 A | 1/1996 | Hafeman |
| 5,489,677 A | 2/1996 | Sanghvi et al. |
| 5,502,177 A | 3/1996 | Matteucci et al. |
| 5,514,786 A | 5/1996 | Cook et al. |
| 5,532,130 A | 7/1996 | Alul |
| 5,578,718 A | 11/1996 | Cook et al. |
| 5,580,767 A | 12/1996 | Cowsert et al. |
| 5,587,361 A | 12/1996 | Cook et al. |
| 5,587,469 A | 12/1996 | Cook et al. |
| 5,587,470 A | 12/1996 | Cook et al. |
| 5,591,721 A | 1/1997 | Agrawal et al. |
| 5,594,121 A | 1/1997 | Froehler et al. |
| 5,596,086 A | 1/1997 | Matteucci et al. |
| 5,608,046 A | 3/1997 | Cook et al. |
| 5,610,289 A | 3/1997 | Cook et al. |
| 5,614,617 A | 3/1997 | Cook et al. |
| 5,635,488 A | 6/1997 | Cook et al. |
| 5,637,573 A | 6/1997 | Agrawal et al. |
| 5,644,048 A | 7/1997 | Yau |

(Continued)

FOREIGN PATENT DOCUMENTS

EP 1 114 623 10/2001

(Continued)

OTHER PUBLICATIONS

European Search Report from European Patent Application No. 05734330.3, dated Feb. 10, 2009, 4 pages.

(Continued)

Primary Examiner—Kimberly Chong
(74) Attorney, Agent, or Firm—Kalow & Springut, LLP; Scott D. Locke, Esq.

(57) ABSTRACT

Methods and compositions for performing RNA interference with decreased off-target effects are provided. The methods and compositions permit effective and efficient applications of RNA interference to applications such as diagnostics and therapeutics through the use of modifications to the siRNA. Uniquely modified siRNAs have been developed that reduce off-target effects incurred in gene-silencing. The modifications comprise 2'-O-alkyl or mismatch modification(s) at specific positions on the sense and/or antisense strands.

9 Claims, 29 Drawing Sheets

U.S. PATENT DOCUMENTS

| | | | |
|---|---|---|---|
| 5,645,985 A | 7/1997 | Froehler et al. |
| 5,652,355 A | 7/1997 | Metelev et al. |
| 5,652,356 A | 7/1997 | Agrawal |
| 5,658,731 A | 8/1997 | Sproat et al. |
| 5,670,633 A | 9/1997 | Cook et al. |
| 5,674,108 A | 10/1997 | Rolle |
| 5,674,908 A | 10/1997 | Haces |
| 5,677,437 A | 10/1997 | Teng et al. |
| 5,681,941 A | 10/1997 | Cook et al. |
| 5,708,161 A | 1/1998 | Reese |
| 5,734,041 A | 3/1998 | Just et al. |
| 5,750,666 A | 5/1998 | Caruthers et al. |
| 5,756,710 A | 5/1998 | Stein et al. |
| 5,757,710 A | 5/1998 | Li et al. |
| 5,763,588 A | 6/1998 | Matteucci et al. |
| 5,767,264 A | 6/1998 | Otvos et al. |
| 5,770,713 A | 6/1998 | Imbach et al. |
| 5,773,601 A | 6/1998 | Agrawal |
| 5,777,092 A | 7/1998 | Cook et al. |
| 5,792,844 A | 8/1998 | Sanghvi et al. |
| 5,792,847 A | 8/1998 | Buhr et al. |
| 5,811,274 A | 9/1998 | Palsson |
| 5,811,534 A | 9/1998 | Cook et al. |
| 5,817,781 A | 10/1998 | Swaminathan et al. |
| 5,830,653 A | 11/1998 | Froehler et al. |
| 5,834,439 A | 11/1998 | Haces |
| 5,834,607 A | 11/1998 | Manoharan et al. |
| 5,849,902 A | 12/1998 | Arrow et al. |
| 5,852,182 A | 12/1998 | Cook et al. |
| 5,852,188 A | 12/1998 | Cook |
| 5,856,455 A | 1/1999 | Cook |
| 5,859,221 A | 1/1999 | Cook et al. |
| 5,872,232 A | 2/1999 | Cook et al. |
| 5,883,237 A | 3/1999 | Stec et al. |
| 5,889,136 A | 3/1999 | Scaringe et al. |
| 5,898,031 A | 4/1999 | Crooke |
| 5,912,339 A | 6/1999 | Miller |
| 5,914,396 A | 6/1999 | Cook et al. |
| 5,919,619 A | 7/1999 | Tullis |
| 5,948,903 A | 9/1999 | Cook et al. |
| 5,965,722 A | 10/1999 | Ecker et al. |
| 5,973,136 A | 10/1999 | Agrawal |
| 5,989,835 A | 11/1999 | Dunlay |
| 5,989,912 A | 11/1999 | Arrow et al. |
| 5,998,203 A | 12/1999 | Matulic-Adamic et al. |
| 5,998,206 A | 12/1999 | Cowsert |
| 6,005,087 A | 12/1999 | Cook et al. |
| 6,005,094 A | 12/1999 | Simon et al. |
| 6,005,096 A | 12/1999 | Matteucci et al. |
| 6,007,992 A | 12/1999 | Lin et al. |
| 6,008,400 A | 12/1999 | Scaringe et al. |
| 6,028,183 A | 2/2000 | Lin et al. |
| 6,043,352 A | 3/2000 | Manoharan et al. |
| 6,060,592 A | 5/2000 | Acevedo et al. |
| 6,110,916 A | 8/2000 | Dunlay |
| 6,111,085 A | 8/2000 | Cook et al. |
| 6,111,086 A | 8/2000 | Scaringe |
| 6,114,513 A | 9/2000 | Cook et al. |
| 6,127,533 A | 10/2000 | Cook et al. |
| 6,140,482 A | 10/2000 | Iyer et al. |
| 6,143,881 A | 11/2000 | Metelev et al. |
| 6,147,200 A | 11/2000 | Manoharan et al. |
| 6,153,737 A | 11/2000 | Manoharan et al. |
| 6,166,188 A | 12/2000 | Cook et al. |
| 6,166,197 A | 12/2000 | Cook |
| 6,172,209 B1 | 1/2001 | Manoharan et al. |
| 6,197,944 B1 | 3/2001 | Walder et al. |
| 6,204,027 B1 | 3/2001 | Goodchild |
| 6,222,025 B1 | 4/2001 | Cook et al. |
| 6,235,886 B1 | 5/2001 | Manoharan et al. |
| 6,239,265 B1 | 5/2001 | Cook |
| 6,242,589 B1 | 6/2001 | Cook et al. |
| 6,242,591 B1 | 6/2001 | Cole et al. |
| 6,265,558 B1 | 7/2001 | Cook et al. |
| 6,271,358 B1 | 8/2001 | Manoharan et al. |
| 6,277,967 B1 | 8/2001 | Manoharan |
| 6,277,982 B1 | 8/2001 | Fraser et al. |
| 6,300,319 B1 | 10/2001 | Manoharan |
| 6,307,040 B1 | 10/2001 | Cook |
| 6,322,987 B1 | 11/2001 | Cook et al. |
| 6,326,358 B1 | 12/2001 | Manoharan |
| 6,331,441 B1 | 12/2001 | Balch |
| 6,335,437 B1 | 1/2002 | Manoharan |
| 6,346,614 B1 | 2/2002 | Metelev et al. |
| 6,348,312 B1 | 2/2002 | Peyman et al. |
| 6,358,931 B1 | 3/2002 | Cook et al. |
| 6,359,124 B1 | 3/2002 | Ecker et al. |
| 6,369,040 B1 | 4/2002 | Acevedo et al. |
| 6,369,209 B1 | 4/2002 | Manoharan |
| 6,380,368 B1 | 4/2002 | Froehler |
| 6,391,636 B1 | 5/2002 | Monia |
| 6,395,492 B1 | 5/2002 | Manoharan et al. |
| 6,399,297 B1 | 6/2002 | Baker et al. |
| 6,399,663 B1 | 6/2002 | Haces |
| 6,403,781 B2 | 6/2002 | Cole et al. |
| 6,410,702 B1 | 6/2002 | Swaminathan |
| 6,414,127 B1 | 7/2002 | Lin et al. |
| 6,416,959 B1 | 7/2002 | Giuliano |
| 6,420,546 B1 | 7/2002 | Seliger et al. |
| 6,440,943 B1 | 8/2002 | Cook et al. |
| 6,447,998 B1 | 9/2002 | Froehler et al. |
| 6,451,991 B1 | 9/2002 | Martin et al. |
| 6,458,940 B2 | 10/2002 | Roberts et al. |
| 6,476,205 B1 | 11/2002 | Buhr et al. |
| 6,485,974 B1 | 11/2002 | Popoff |
| 6,495,672 B1 | 12/2002 | Froehler et al. |
| 6,506,559 B1 | 1/2003 | Fire |
| 6,514,464 B1 | 2/2003 | Knebel |
| 6,525,031 B2 | 2/2003 | Manoharan |
| 6,531,584 B1 | 3/2003 | Cook et al. |
| 6,534,639 B1 | 3/2003 | Manoharan et al. |
| 6,544,790 B1 | 4/2003 | Sabatini |
| 6,573,039 B1 | 6/2003 | Dunlay |
| 6,576,752 B1 | 6/2003 | Manoharan et al. |
| 6,590,093 B1 | 7/2003 | Scaringe |
| 6,600,032 B1 | 7/2003 | Manoharan et al. |
| 6,608,035 B1 | 8/2003 | Agrawal et al. |
| 6,620,591 B1 | 9/2003 | Dunlay |
| 6,624,293 B1 | 9/2003 | Agrawal |
| 6,645,943 B1 | 11/2003 | Agrawal et al. |
| 6,653,458 B1 | 11/2003 | Manoharan et al. |
| 6,671,624 B1 | 12/2003 | Dunlay |
| 6,673,611 B2 | 1/2004 | Thompson et al. |
| 6,677,445 B1 | 1/2004 | Innis et al. |
| 6,716,582 B2 | 4/2004 | Gonye |
| 6,716,588 B2 | 4/2004 | Sammak |
| 6,716,882 B2 | 4/2004 | Haces |
| 6,759,206 B1 | 7/2004 | Rubin |
| 6,809,193 B2 | 10/2004 | McKay et al. |
| 6,841,542 B2 | 1/2005 | Bartelmez |
| 6,875,578 B2 | 4/2005 | Giuliano |
| 6,902,883 B2 | 6/2005 | Dunlay |
| 6,924,109 B2 | 8/2005 | Melcher |
| 6,951,757 B2 | 10/2005 | Sabatini |
| 2001/0003132 A1 | 6/2001 | Cole et al. |
| 2001/0027251 A1 | 10/2001 | Cook et al. |
| 2001/0044528 A1 | 11/2001 | Innis et al. |
| 2002/0006664 A1 | 1/2002 | Sabatini |
| 2002/0099192 A1 | 7/2002 | Metelev et al. |
| 2002/0128466 A1 | 9/2002 | Cole et al. |
| 2002/0142980 A1 | 10/2002 | Thompson et al. |
| 2002/0160379 A1 | 10/2002 | Cook et al. |
| 2003/0036516 A1 | 2/2003 | Agrawal |
| 2003/0045698 A1 | 3/2003 | Manoharan et al. |

| | | | |
|---|---|---|---|
| 2003/0051270 A1 | 3/2003 | Kmiec et al. | |
| 2003/0060440 A1 | 3/2003 | Klinman et al. | |
| 2003/0083477 A1 | 5/2003 | Arrow et al. | |
| 2003/0096770 A1 | 5/2003 | Krotz et al. | |
| 2003/0096776 A1 | 5/2003 | Hanecak et al. | |
| 2003/0100521 A1 | 5/2003 | Agrawal | |
| 2003/0109471 A1 | 6/2003 | Iyer et al. | |
| 2003/0135033 A1 | 7/2003 | Klippel-Giese et al. | |
| 2003/0148980 A1 | 8/2003 | Metelev et al. | |
| 2003/0170642 A1 | 9/2003 | Caldwell | |
| 2003/0170891 A1 | 9/2003 | McSwiggen | |
| 2003/0190626 A1 | 10/2003 | Ravikumar | |
| 2003/0203486 A1 | 10/2003 | Sabatini | |
| 2003/0206887 A1 | 11/2003 | Morrissey | |
| 2003/0228601 A1 | 12/2003 | Sabatini | |
| 2004/0009938 A1 | 1/2004 | Manoharan et al. | |
| 2004/0014108 A1 | 1/2004 | Eldrup et al. | |
| 2004/0014956 A1 | 1/2004 | Woolf et al. | |
| 2004/0014957 A1 | 1/2004 | Eldrup et al. | |
| 2004/0019008 A1 | 1/2004 | Lewis | |
| 2004/0043948 A1 | 3/2004 | Baker et al. | |
| 2004/0053875 A1 | 3/2004 | Kreutzer et al. | |
| 2004/0054155 A1 | 3/2004 | Woolf et al. | |
| 2004/0058886 A1 | 3/2004 | Scaringe | |
| 2004/0072779 A1 | 4/2004 | Kreutzer et al. | |
| 2004/0096880 A1 | 5/2004 | Kmiec et al. | |
| 2004/0102408 A1 | 5/2004 | Kreutzer et al. | |
| 2004/0110296 A1 | 6/2004 | Vargeese | |
| 2004/0147022 A1 | 7/2004 | Baker et al. | |
| 2004/0147023 A1 | 7/2004 | Baker et al. | |
| 2004/0167090 A1 | 8/2004 | Monahan et al. | |
| 2004/0180351 A1 | 9/2004 | Giese | |
| 2004/0198640 A1 | 10/2004 | Leake et al. | |
| 2004/0204420 A1 | 10/2004 | Rana | |
| 2004/0229266 A1 | 11/2004 | Tuschl et al. | |
| 2004/0248299 A1 | 12/2004 | Jayasena et al. | |
| 2004/0266707 A1 | 12/2004 | Leake et al. | |
| 2005/0014257 A1 | 1/2005 | Crooke et al. | |
| 2005/0020521 A1 | 1/2005 | Rana et al. | |
| 2005/0020525 A1 | 1/2005 | McSwiggen et al. | |
| 2005/0026160 A1 | 2/2005 | Allerson et al. | |
| 2005/0059044 A1 | 3/2005 | Graham | |
| 2005/0130181 A1 | 6/2005 | McSwiggen | |
| 2005/0181385 A1 | 8/2005 | Linsley | |
| 2005/0223427 A1 | 10/2005 | Leake | |
| 2005/0239728 A1 | 10/2005 | Pachuk | |
| 2005/0255487 A1 | 11/2005 | Khvorova | |
| 2006/0110766 A1 | 5/2006 | Robertson | |
| 2006/0110829 A1 | 5/2006 | Robertson | |
| 2006/0115461 A1 | 6/2006 | Robertson | |
| 2006/0127891 A1 | 6/2006 | McSwiggen | |
| 2006/0166234 A1 | 7/2006 | Robertson | |
| 2006/0178324 A1 | 8/2006 | Hadwiger | |
| 2006/0223777 A1 | 10/2006 | Vermeulen | |
| 2007/0167384 A1 | 7/2007 | Leake | |
| 2007/0173476 A1 | 7/2007 | Leake | |
| 2007/0269889 A1 | 11/2007 | Leake | |

FOREIGN PATENT DOCUMENTS

| | | |
|---|---|---|
| EP | 1114623 | 10/2001 |
| EP | 1 389 637 | 2/2004 |
| EP | 1559785 | 8/2005 |
| WO | WO/93/04204 | 3/1993 |
| WO | 94-01550 | 1/1994 |
| WO | WO/94/21825 | 9/1994 |
| WO | WO/94/26887 | 11/1994 |
| WO | 97-42819 | 11/1997 |
| WO | 99-32619 | 7/1999 |
| WO | WO/99/32619 | 7/1999 |
| WO | 00-12454 | 3/2000 |
| WO | 01-20015 | 3/2001 |
| WO | 01-75164 | 10/2001 |
| WO | WO/01/75164 | 10/2001 |
| WO | 02-44321 | 6/2002 |
| WO | WO/02/44321 | 6/2002 |
| WO | WO/02/094185 | 11/2002 |
| WO | 03-064625 | 8/2003 |
| WO | 03-064626 | 8/2003 |
| WO | WO/03/064625 | 8/2003 |
| WO | WO/03/064626 | 8/2003 |
| WO | WO/03/070193 | 8/2003 |
| WO | WO/03/070918 | 8/2003 |
| WO | 03-072705 A2 | 9/2003 |
| WO | 03-072705 A3 | 9/2003 |
| WO | WO/03/072705 | 9/2003 |
| WO | WO/03/074654 | 9/2003 |
| WO | 2004-009847 | 1/2004 |
| WO | 2004-011624 | 2/2004 |
| WO | 2004-015107 A2 | 2/2004 |
| WO | 2004-015107 A3 | 2/2004 |
| WO | WO/2004/015107 | 2/2004 |
| WO | WO/2004/045543 | 6/2004 |
| WO | 2004-078946 | 9/2004 |
| WO | 2004-080406 | 9/2004 |
| WO | WO/2004/080406 | 9/2004 |
| WO | 2004-091515 | 10/2004 |
| WO | WO/2004/090105 | 10/2004 |
| WO | WO/2004/091515 | 10/2004 |
| WO | 2004-109290 | 12/2004 |
| WO | WO/2004/109290 | 12/2004 |
| WO | WO/2005/019453 | 3/2005 |
| WO | 2005-078094 | 8/2005 |
| WO | 2005-097992 | 10/2005 |
| WO | 2006-058046 | 6/2006 |
| WO | 2006-058048 | 6/2006 |
| WO | 2006-060246 | 6/2006 |
| WO | 2006-071410 | 7/2006 |

OTHER PUBLICATIONS

Amarzguioui et al., "Tolerance for mutations and chemical modifications in a siRNA," Nucleic Acids Research, 2003, vol. 31, No. 2, pp. 589-595, Oxford University Press.
Braasch, D. et al. (2003) *RNA Interference in Mammalian Cells by Chemically-modified RNA*, Biochemistry 42/26:7967-7995.
Boiziau et al. (1995) Antisense 2'-O-alkyl Oligoribonucleotides are efficient inhibitors of revers transcription, Nucleic Acids Res. 23/1:64-71.
Chiu, et al. (2003) siRNA function in RNAi: A chemical modification analyisis, RNA 9/9:1034-1048.
Conrad et al. (1995) Enzymatic synthesis of 2'-modified nucleic acids: identification of important phosphate and ribose moieties in RNase P substrates, Nucleic Acids Res. 23/11:1845-1853.
Czauderna et al. (2003) Structural variations and stabilizing modifications of synthetic siRNAs in mammalian cells, Nucleic Acids Res. 31/11:2705-2716.
Elbashir et al., RNA interference is mediated by 21-22-nucleotide RNAs, Jan. 2001, Genes & Development, vol. 15, pp. 188-200.
Grünweller, et al. (2003) Comparison of different antisense strategies in mammalian cells using locked nucleic acids, 2'-O-methyl RNA, phosphorothioates and small interfering RNA, Nucleic Acids Res. 31/12:3185-3193.
Harborth, J. et al. (2003-4) *Sequence, Chemical, and Structural Variation of Small Interfering RNAs and Short Hairkpin RNAs and the Effecgt on Mammalian Gene Silencing*, Antisense & Nucleic Acid Drug Development 13/2:83-105.
Holen et al. (2003) Similar behaviour of single-strand and double-strand siRNA's suggests they act through a common RNAi pathway, Nucleic Acids Res. 31/9:2401-2407.
International Search Report for PCT/US2005/011008, dated Nov. 2, 2005 (5 pages).
Jackson, A.L. et al. (2003) Expression Profiling Reveals off-target Gene Regulation by RNAI, Nature Biotechnology 21/6:635-637.

Johansson et al. (1994) Target-specific arrest of mRNA translation by antisense 2'-O-Alkyloligoribonucleotides, Nucleic Acids Res. 22/22:4591-4598.

Larrouy et al. (1995) RNase H is responsible for the non-specific inhibition of in vitro translation by 2'O-alkyl chimeric oligonucleotides: high affinity or selectivity, a dilemma to design antisense oligomers, Nucleic Acids Res. 23/17:3434-3440.

Liang, L. et al. (2002) Optimizing the delivery systems of chimeric RNA-DNA oligonucleotides: Beyond general oligonucleotide transfer, Eur. J. Biochem 269:5753-5758.

Letsigner et al., Cholesteryl-conjugated oligonucleotides: Synthesis, properties, and activity as inhibitors of replication of human immunodeficiency virus in cell culture, Sep. 1989, Proc. Natl. Acad. Sci., vol. 86, pp. 6553-6556.

Lubini et al., Stabilizing effects of the RNA 2'-sistitutent: crystal structure oligodeoxynucleotide duplex containing 2'-O-methylated adenosines. Chem Biol. 1004 Sep. 1(1): 39-45.

Majlessi, et al. (1998) Advantages of 2'-O-methyl oligoribonucleotide probes for detecting RNA targets, Nucleic Acids Res. 26/9:2224-2229.

Monia, et al. (1993) Evaluation of 2'-Modified Oligonucleotides Containing 2'-Deoxy Gaps as Antisense Inhibitors of Gene Expression, J. Biol. Chem. 268/19:14514-14522.

Nykänen, et al. (2001) ATP Requirements and Small Interfering RNA Structure in the RNA Interference Pathway, Cell 107:309-321.

Parrish et al., Functional Anatomy of a dsRNA Trigger: Differential Requirement for the Two Trigger Strands in RNA Interference, Nov. 2000, Molecular Cell, vol. 6, pp. 1077-1087.

Rossi, J., "A Cholesterol Connection in RNAi," Nature, Nov. 2004, vol. 432, pp. 155-156.

Soutscheck, J., et al., "Therapeutic Silencing of an Endogenous Gene by Systemic Administration of Modified siRNAs," Nature, Nov. 2004, vol. 432, pp. 173-178.

Stump, et al. (1999) The use of modified primers to eliminate cycle sequencing artifacts, Nucleic Acids Res. 27/23:4642-4648.

Uchiyama, et al. (1994) Studies of the Interactions Between *Escherichia coli* Ribonuclease HI and Its Substrate, J. Mol. Boil. 243-782-791.

Written Opinion of the International Searching Authority for PCT/US2005/011008 (6 pages).

Office Action, U.S. Appl. No. 10/406,908, Mail Date: Jan. 14, 2005.
Office Action, U.S. Appl. No. 10/406,908, Mail Date: Apr. 5, 2005.
Office Action, U.S. Appl. No. 10/406,908, Mail Date: Sep. 23, 2005.
Office Action, U.S. Appl. No. 10/406,908, Mail Date: Jan. 30, 2006.
Office Action, U.S. Appl. No. 10/406,908, Mail Date: Sep. 22, 2006.
Office Action, U.S. Appl. No. 10/613,077, Mail Date: Jan. 27, 2005.
Office Action, U.S. Appl. No. 10/613,077, Mail Date: Apr. 12, 2005.
Office Action, U.S. Appl. No. 10/613,077, Mail Date: Sep. 7, 2005.
Office Action, U.S. Appl. No. 10/613,077, Mail Date: Apr. 3, 2006.
Office Action, U.S. Appl. No. 11/019,831, Mail Date: Aug. 23, 2005.
Office Action, U.S. Appl. No. 11/019,831, Mail Date: Feb. 21, 2006.
Office Action, U.S. Appl. No. 11/019,831, Mail Date: Jun. 28, 2006.
Office Action, U.S. Appl. No. 11/019,831, Mail Date: Feb. 9, 2007.
Examiner's First Report Australian Patent Application No. 2005230850. Mar. 18, 2008.
Office Action Canadian Patent Application No. 2,561,868. Mar. 19, 2010.
Communication Pursuant to Article 96(2) EPC. European Patent Application No. 05734 330.3 -2405. Apr. 16, 2007.
Office Action Japanese Patent Application No. 2007-506294. 2010.
Examination Report Singapore Patent Application No. 200606767-2. Feb. 11, 2010.
U.S. Appl. No. 11/857,732, filed Sep. 19, 2007, Khvorova.

Vermeulen, A. et al., "The Contribution of dsRNA Structure to Dicer Specificity and Efficiency"; RNA, 11:674-682 (2005).

Atlas Venture, Dharmacon and Akceli Announce Research Collaboration to Combine reverse Transfection and siRNA for High Throughput Gene Silencing, www.atlasventure.com/home/news_content.asp?ne_id=1741 (Aug. 24, 2004).

Ambion, High Throughput siRNA Delivery in Vitro: From Cell Lines to Primary Cells, TechNotes 12(2); ww.ambion.com/techlib/tn/122/3.html (Downloaded Jul. 18, 2005).

Boston Business Journal, "Biotech firm Akceli wins first patent," www.bizhournals.com/boston/stories/2003/04/07/daily13.html.

Dhellin, Oliver et al., "Functional differences between the human LINE retrotransposition and retroviral reverse transcripts for in vivo mRNA reverse transcription," the EMBO Journal, vol. 16, pp. 6590-6602; 1997.

Press Release, Dharmacon Launches siArray RTF™ siRNA Libraries—First Ever Using Reverse Transfection Technology, qb Perbio Solutions for Life Science; Layfayette, Colo.; Apr. 22, 2005.

Hannon, Gregory J., "RNA Interference," Nature, vol. 418; Jul. 11, 2002, (www.nature.com/nature).

Ketting, R.F. et al., (2001) Dicer Functions in RNA Interference and in Synthesis of small RNA Involved in Developmental Timing in C. elegans Genes Dev., Oct. 15, 2001, 15(20):2654-9.

Paddison, P.J., et al., "A Resource for Large-Scale RNA Interference-Based screens in mammals," Nature, vol. 428; Mar. 25, 2004, (www.nature.com/nature).

He, L. et al, "MicroRNAs with a big role in gene regulation," Nature, vol. 5, pp. 522-532, Jul. 2004, (www.nature.com/reviews/genetics).

Hannon, Gregory J. et al, "Unlocking the Potential of the Human Genome with RNA Interference," Nature, vol. 431; Sep. 16, 2004, (www.nature.com/nature).

Hammond, S.M., et al. "Post-Transcriptional Gene Splicing by Double-Stranded RNA," Nature, vol. 2; Feb. 2001, (www.nature.com/reviews/genetics).

Harmon G., "Growth control in mammalian cells: Post transcriptional gene silencing" (wwww.cshl.org/public/SCIENCE/hannon.html) (2004).

Denali, A.M. et al., "RNAi: an ever growing puzzle," TRENDS in Biochemical Sciences, vol. 28, No. 4, Apr. 2003.

Silva, J.M. et al., "RNA interference: a promising approach to antiviral therapy?" Trends in Molecular Medicine, vol. 8, No. 11, Nov. 2002.

"The HiPerformance Algorithm Designs Highly Potent and Specific siRNA", Technical Information, www1.qiagen.com/literature/resources/RNAi/1030174_TI_GS_siRNA_0105.pdf; downloaded Jul. 18, 2005.

Ziauddin, J. et al., "Microarrays of cells expressing defined cDNAs," Letters to Nature, Nature, 411, pp. 107-110 (May 3, 2001); doi:10.1038/35075114.

Reverse Transfection Homepage and Guide, Ziauddin, J. and Sabatini, D., http://staffa.wi.mit.edu/sabatini_public/reverse/transfection/content (downloaded Aug. 24, 2004).

Product Insert, siARRAY™ siRNA Libraries, Version 2.0 Dharmacon RNA Technologies, 2004.

SuperArray Bioscience Corporation, Introducing siRNA Array Plates, www.superarray.com/RNAiArrayPlates.php (downloaded Jul. 18, 2005).

SuperArray Bioscience Corporation, siRNA Array Plates, www.superarray.com/manuals/Present_ArrayPlates.pdf (downloaded Jul. 18, 2005).

SuperArray Bioscience Corporation, Newly Released SureSilencing™ Mouse siRNA Products, www.superarray.com/siRNAnew.php?sp=Mouse (downloaded Jul. 18, 2005).

SuperArray Bioscience Corporation, Newly Released SureSilencing™ Human siRNA Products, www.superarray.com/siRNAnew.php?sp=Human (downloaded Jul. 18, 2005).

Qiagen, Transfection Reagent Selector Kit Handbook, Jan. 1999.

Bernstein, E., et al., "The rest is Silence," RNA (2001), 7:1509-1521. Cambridge University Press.

Mousses et al., RNAi Microarray Analysis in Cultured Mammalian Cells. Genome Research 2003, vol. 13, pp. 2341-2347.

Vanhecke et al., High-Throughput Gene Silencing Using Cell Arrays, Oncogene Nov. 1, 2004 vol. 23, pp. 8353-8358.

Silva et al., RNA Interference Microarrays, High-Throughput Loss-of-Function Genetics in Mammalian Cells. PNAS. Apr. 27, 2004, vol. 101, No. 17, pp. 6548-6552.

Kumar et al., High-Throughput Selection of Effective RNAi Probes for Gene Silencing, Genome Research, 2003, vol. 13, pp. 2333-2340.

Bailey et al, Applications of Transfected Cell Microarrays in High-Throughput Drug Discovery Today, 2002, vol. 7, pp. S113-S118.

Homna et al., The Role of Atelococollagen-based cell Transfection array in High-Throughput Screening of Gene Functions and in Drug Discover, Current Drug Discovery Technologies, Dec. 2004, vol. 1, pp. 287-294.
International Search Report from PCT/US2005/042407, Sep. 8, 2006, 2 pages.
International Preliminary Report on Patentability from PCT/US2005/042407, May 22, 2007, 4 pages.
Written Opinion from PCT/US2005/042407, Jun. 20, 2006, 3 pages.
International Search Report from PCT/US2005/042403, Sep. 26, 2006, 4 pages.
International Preliminary Report on Patentability from PCT/US2005/042403, May 22, 2007, 4 pages.
Written Opinion from PCT/US2005/042403, Jun. 8, 2006, 3 pages.
International Search Report from PCT/US/042385, Apr. 5, 2007, 3 pages.
International Preliminary Report on Patentability from PCT/US2005/042385, May 22, 2007, 4 pages.
Written Opinion from PCT/US2005/042385 Jan. 29, 2007, 3 pages.
International Search Report from PCT/US2005/042404, May 22, 2007, 5 pages.
International Preliminary Report on Patentability from PCT/US2006/042404, May 22, 2007, 5 pages.
Written Opinion from PCT/US2006/042404, Mar. 7, 2007, 4 pages.
Amarzguioui et al., Tolerance for Mutations and Chemical Modifications in siRNA, 2003, Nucleic Acids Research, vol. 31, No. 2, pp. 589-595 Oxford University Press.
Elbashir et al., RNA Interference is Mediated by 21- and 22-Nucleotide RNAs, Jan. 2001, Genes & Development, vol. 15, pp. 188-200.
Letsinger et al. Cholesteryl-conjugated Oligonucleotides: Synthesis, properties, and activity as inhibitors of replication of human immunodeficiency virus in cell culture, Sep. 1989, Proc. Natl. Acad. Sci. vol. 86, pp. 6553-6556.
Boiziau et al, (1995) Antisense 2"-O-alkyl Oligoribinucleotides are efficient inhibitors of reverse transcription, Nucleic Acids Res. 23/1:64-71.
Chiu et al. (2003) siRNA function in RNAi: A Chemical Modification Analysis, RNA 9/9:1034-1048.
Grunweller et al. (2003) Comparison of different antisense strategies in mammalian cells using locked nucleic acid, 2'-O-methyl RNA, phosphorothioates and small interfering RNA, Nucleic Acids Res. 31/12:3185-3193.
Holen et al. (2003) Similar behavior of single-strand and double-strand siRNAs suggests they act through a common RNAi pathway, Nucleic Acids Res. 31/9:2401-2407.
Liang, L. et al (2002) Optimizing the delivery systems of chimeric RNA-DNA oligonucleotides: Beyond general oligonucleotide transfer, Eur J. Biochem 269:5953-5758.
Majlessi et al. (1998) Advantages of 2'-O-methyl oligoribonucleotide probes for detecting RNA targets, Nuclic Acids Res.26/9:2224-2229.
Monia et al. (1993) Evaluation of 2'-Modified Oligonucleotides Containing 2'-Deoxy gaps as Antisense Inhibitors of Gens Expression, J. Biol. Chem. 268/19:14514-14522.
Nykanen et al. (2001) ATP Requirements and Small Interfering RNA Structure in the RNA Interference Pathway, Cell 107:309-321.
Stump et al. (1999) The use of modified primers to eliminate cycle sequencing artifacts, Nucleic Acids Res. 27/23:4642-4648.
Uchiyama et al. (1994) Studies of the Interactions Between Escherichia coli Ribonuclease HI and Its Substrate, J Mol. Biol. 243:782-791.
Braasch, D. et al (2003) "RNA Interference in Mammalian Cells by Chemically-modified RNA" Biochemistry 42/26:7967-7995.
Harborth, J. et al. (2003-4) "Sequence, Chemical, and Structural Cariation of Small Interfering RNAs and Short Harpin RNAs and the Effect on Mammalian Gene Silencing" Antisense & Nucleic Acid Drug Development 13/2:83-105.

Elbashir, S. M. et al (2001) Functional Anatomy of siRNAs for Mediating efficient RNAi in Drosophila melanogaster embyro lysate, The EMBO Journal 20/23:6877-6888.
Jackson, A. L. et al. (2003) Expression Profiling Reveals off-target Gene Regulation by RNAI, Nature Biotechnology 21/6:635-637.
Lubini et al. Stabilizing effects of the RNA 2'-sustitutent Crystal Structure of an Oligodeoxynucleotide duplex Containing 2'-O-methylated adenosines Chem. Biol. 1004 Sep. 1(1):39-45.
Dharmacon RNA Technologies, Dharmacon and Merck's Rosetta Collaborate to Assess Multiple Factors Affecting Efficacy and Specificity of siRNA for Gene Silencing, Oct. 8, 2003, Press Release, Layfette, CO.
Rosetta siRNA Experiments Performed in 2007, pp. 1-11.
Kim, D. H. et al., Synthetic dsRNA Dicer Substrates Enhance RNAi Patency and efficacy, Nature Biotechnology, Advanced Online Publication, (2004), p. 1-5, Published Online Dec. 26, 2004.
Paddison, Patrick J. et al., "Short hairpin RNAs shRNAs) induce sequence-specific silencing in mammalian cells", Genes & Development 16, (2002), p. 946-958.
Zhang, Haidi et al., "Human Dicer Preferentially cleaves dsRNAs at their termini without a requirement for ATP", The EMBO Journal vol. 21, No. 21, (2002), p. 5875-5885.
Hohjoh, Hirohiko, "Enhancement of RNAi activity by improved siRNA duplexes", FEBS letters 557, (2004), p. 193-198.
Ma, Jin-Baio et al., "Structural basis for overhanging-specific small interfering RNA recognition by PAZ domain", Nature, vol. 429, May 20, 2004, p. 318-322.
Siolas, Despina, "Synthetic shRNAs as potent RNAi triggers", Nature Biotechnology, p. 1-5, published online Dec. 26, 2004.
Zeng, Yan et al., "Both Natural and Designed Micro RNAs Technique Can Inhibit the Expression of Cognate mRNAs When Expressed in Human Cells", Molecular Cell, vol. 9, Jun. 2002, p. 1327-1333.
Holen et al. (2002) Positional Effects of short interfering RNAs targeting the human coagulation trigger Tissue Factor, Nucleic Acid Research, 30/8:1757-1766.
International Search Report from PCT/US05/011008, Mar. 31, 2005, 5 Pages.
Written Opinion from PCT/US05/011008, Mar. 31, 2005, 6 Pages.
International Search Report from PCT/US05/003365, Apr. 2, 2005, 7 Pages.
Written Opinion from PCT/US05/003365, Apr. 2, 2005, 10 Pages.
Notification Regarding Review of Justification for Invitation to Pay Additional Fees from PCT/US05.003365, Apr. 2, 2005, 4 Pages.
Office Action dated Mar. 21, 2007 cited in U.S. Appl. No. 11/283,484.
Office Action dated Jul. 8, 2008 cited in U.S. Appl. No. 11/283,484.
Office Action dated Oct. 15, 2008 cited in U.S. Appl. No. 11/283,482.
Office Action dated Nov. 3, 2008 cited in U.S. Appl. No. 11/283,483.
Office Action dated Dec. 9, 2008 cited in U.S. Appl. No. 11/283,481.
Office Action dated Oct. 30, 2007 cited in U.S. Appl. No. 11/019,831.
Office Action dated Sep. 4, 2008 cited in U.S. Appl. No. 11/019,831.
Office Action dated Sep. 12, 2008 cited in U.S. Appl. No. 11/390,829.
Office Action dated Feb. 22, 2008 cited in U.S. Appl. No. 11/051,195.
Office Action dated Dec. 18, 2008 cited in U.S. Appl. No. 11/051,195.
Office Action dated Sep. 8, 2008 cited in U.S. Appl. No. 10/551,350.
Office Action dated Dec. 31, 2008 cited in U.S. Appl. No. 11/619,993.
Office Action dated Jan. 14, 2005 cited in U.S. Appl. No. 10/406,908.
Office Action dated Apr. 5, 2005 cited in U.S. Appl. No. 10/406,908.
Office Action dated Sep. 23, 2005 cited in U.S. Appl. No. 10/406,908.
Office Action dated Jan. 27, 2005 cited in U.S. Appl. No. 10/613,077.
Office Action dated Apr. 12, 2005 cited in U.S. Appl. No. 10/613,077.
Office Action dated Sep. 7, 2005 cited in U.S. Appl. No. 10/613,077.

(i) Couple next nucleoside with S-ethyl-tetrazole catalyst, 60 seconds
(ii) Cap unreacted 5'-hydroxyls, 20 seconds
(iii) Oxidize phosphorus linkage (t-butyl hydroperoxide)
(iv) 5'-deprotection with triethylammonium fluoride ions (TEAHF), 30 seconds

SEQUENCE LISTING

<160> NUMBER OF SEQ ID NOS: 301

<210> SEQ ID NO 1
<211> LENGTH: 19
<212> TYPE: RNA
<213> ORGANISM: Homo Sapiens
<220> FEATURE:

<400> SEQUENCE: 1
ugcugaccuc uguuaccuc                                            19

<210> SEQ ID NO 2
<211> LENGTH: 19
<212> TYPE: RNA
<213> ORGANISM: Homo Sapiens
<220> FEATURE:

<400> SEQUENCE: 2
gacaugcgaa ugacacuag                                            19

<210> SEQ ID NO 3
<211> LENGTH: 19
<212> TYPE: RNA
<213> ORGANISM: Homo Sapiens
<220> FEATURE:

<400> SEQUENCE: 3
ccuacagaga acugcgguu                                            19

<210> SEQ ID NO 4
<211> LENGTH: 19
<212> TYPE: RNA
<213> ORGANISM: Homo Sapiens
<220> FEATURE:

<400> SEQUENCE: 4
ugcugaccuc uguuaccuc                                            19

<210> SEQ ID NO 5
<211> LENGTH: 19

```
<212> TYPE: RNA
<213> ORGANISM: Homo Sapiens
<220> FEATURE:

<400> SEQUENCE: 5
ccuacagaga acugcgguu                                                   19

<210> SEQ ID NO 6
<211> LENGTH: 19
<212> TYPE: RNA
<213> ORGANISM: Homo Sapiens
<220> FEATURE:

<400> SEQUENCE: 6
gucaucagcu uugugccac                                                   19

<210> SEQ ID NO 7
<211> LENGTH: 19
<212> TYPE: RNA
<213> ORGANISM: Homo Sapiens
<220> FEATURE:

<400> SEQUENCE: 7
gacaugcgaa ugacacuag                                                   19

<210> SEQ ID NO 8
<211> LENGTH: 19
<212> TYPE: RNA
<213> ORGANISM: Homo Sapiens
<220> FEATURE:

<400> SEQUENCE: 8
agaggaacuc ucugcaagc                                                   19

<210> SEQ ID NO 9
<211> LENGTH: 19
<212> TYPE: RNA
<213> ORGANISM: Homo Sapiens
<220> FEATURE:

<400> SEQUENCE: 9
uggaggggaa ugcucagaa                                                   19

<210> SEQ ID NO 10
<211> LENGTH: 19
<212> TYPE: RNA
<213> ORGANISM: Homo Sapiens
<220> FEATURE:

<400> SEQUENCE: 10
uaaagauggc acuucccg                                                    19

<210> SEQ ID NO 11
<211> LENGTH: 19
<212> TYPE: RNA
<213> ORGANISM: Homo Sapiens
<220> FEATURE:

<400> SEQUENCE: 11
ugcugaccuc uguuaccuc                                                   19

<210> SEQ ID NO 12
<211> LENGTH: 19
<212> TYPE: RNA
<213> ORGANISM: Homo Sapiens
```

```
<220> FEATURE:

<400> SEQUENCE: 12
gcucacgguc auuaccgag                                                        19

<210> SEQ ID NO 13
<211> LENGTH: 19
<212> TYPE: RNA
<213> ORGANISM: Homo Sapiens
<220> FEATURE:

<400> SEQUENCE: 13
ccuacagaga acugcgguu                                                        19

<210> SEQ ID NO 14
<211> LENGTH: 19
<212> TYPE: RNA
<213> ORGANISM: Homo Sapiens
<220> FEATURE:

<400> SEQUENCE: 14
ggcuuccuua caaggagau                                                        19

<210> SEQ ID NO 15
<211> LENGTH: 19
<212> TYPE: RNA
<213> ORGANISM: Homo Sapiens
<220> FEATURE:

<400> SEQUENCE: 15
ccuacagaga acugcgguu                                                        19

<210> SEQ ID NO 16
<211> LENGTH: 19
<212> TYPE: RNA
<213> ORGANISM: Homo Sapiens
<220> FEATURE:

<400> SEQUENCE: 16
cgggucuugu guccuucaa                                                        19

<210> SEQ ID NO 17
<211> LENGTH: 19
<212> TYPE: RNA
<213> ORGANISM: Homo Sapiens
<220> FEATURE:

<400> SEQUENCE: 17
gucaucagcu uugugccac                                                        19

<210> SEQ ID NO 18
<211> LENGTH: 4
<212> TYPE: RNA
<213> ORGANISM: Homo Sapiens
<220> FEATURE:

<400> SEQUENCE: 18 uucg                                                                         4

<210> SEQ ID NO 19
<211> LENGTH: 9
<212> TYPE: RNA
<213> ORGANISM: Homo Sapiens
<220> FEATURE:
```

```
<400> SEQUENCE: 19 uuuguguag                                                          9

<210> SEQ ID NO 20
<211> LENGTH: 10
<212> TYPE: RNA
<213> ORGANISM: Homo Sapiens
<220> FEATURE:

<400> SEQUENCE: 20
cuuccuguca                                                        10

<210> SEQ ID NO 21
<211> LENGTH: 7
<212> TYPE: RNA
<213> ORGANISM: Homo Sapiens
<220> FEATURE:

<400> SEQUENCE: 21 auaugug                                                            7

<210> SEQ ID NO 22
<211> LENGTH: 21
<212> TYPE: RNA
<213> ORGANISM: Homo Sapiens
<220> FEATURE:
<221> NAME/KEY: misc_feature
<222> LOCATION: (20)...(21)
<223> OTHER INFORMATION: n is 2 prime deoxythimidine

<400> SEQUENCE: 22
gugauguaug ucagagagun n                                           21

<210> SEQ ID NO 23
<211> LENGTH: 19
<212> TYPE: RNA
<213> ORGANISM: Homo Sapiens
<220> FEATURE:

<400> SEQUENCE: 23
gaaaaaucag agagauccu                                              19

<210> SEQ ID NO 24
<211> LENGTH: 19
<212> TYPE: RNA
<213> ORGANISM: Homo Sapiens
<220> FEATURE:

<400> SEQUENCE: 24
uaccggaaaa cucgacgca                                              19

<210> SEQ ID NO 25
<211> LENGTH: 19
<212> TYPE: RNA
<213> ORGANISM: Homo Sapiens
<220> FEATURE:

<400> SEQUENCE: 25
acgucgccag ucaaguaac                                              19

<210> SEQ ID NO 26
<211> LENGTH: 19
<212> TYPE: RNA
<213> ORGANISM: Homo Sapiens
<220> FEATURE:
```

<400> SEQUENCE: 26
gauuacgucg ccagucaag                                                    19

<210> SEQ ID NO 27
<211> LENGTH: 19
<212> TYPE: RNA
<213> ORGANISM: Homo Sapiens
<220> FEATURE:

<400> SEQUENCE: 27
agagaucgug gauuacguc                                                    19

<210> SEQ ID NO 28
<211> LENGTH: 19
<212> TYPE: RNA
<213> ORGANISM: Homo Sapiens
<220> FEATURE:

<400> SEQUENCE: 28 uguuguuug gagcacgga                                                     19

<210> SEQ ID NO 29
<211> LENGTH: 19
<212> TYPE: RNA
<213> ORGANISM: Homo Sapiens
<220> FEATURE:

<400> SEQUENCE: 29
ccuacagaga acugcgguu                                                    19

<210> SEQ ID NO 30
<211> LENGTH: 19
<212> TYPE: RNA
<213> ORGANISM: Homo Sapiens
<220> FEATURE:

<400> SEQUENCE: 30
ggcuuccuua caaggagau                                                    19

<210> SEQ ID NO 31
<211> LENGTH: 19
<212> TYPE: RNA
<213> ORGANISM: Homo Sapiens
<220> FEATURE:

<400> SEQUENCE: 31
cgggucuugu guccuucaa                                                    19

<210> SEQ ID NO 32
<211> LENGTH: 19
<212> TYPE: RNA
<213> ORGANISM: Homo Sapiens
<220> FEATURE:

<400> SEQUENCE: 32
acgggcaagg ccaauggg                                                     19

<210> SEQ ID NO 33
<211> LENGTH: 19
<212> TYPE: RNA
<213> ORGANISM: Homo Sapiens
<220> FEATURE:

<400> SEQUENCE: 33

```
cgggcaaggc caagugggga                                              19
```

```
<210> SEQ ID NO 34
<211> LENGTH: 19
<212> TYPE: RNA
<213> ORGANISM: Homo Sapiens
<220> FEATURE:

<400> SEQUENCE: 34
gggcaaggcc aagugggau                                               19
```

```
<210> SEQ ID NO 35
<211> LENGTH: 19
<212> TYPE: RNA
<213> ORGANISM: Homo Sapiens
<220> FEATURE:

<400> SEQUENCE: 35
ggcaaggcca agugggaug                                               19
```

```
<210> SEQ ID NO 36
<211> LENGTH: 19
<212> TYPE: RNA
<213> ORGANISM: Homo Sapiens
<220> FEATURE:

<400> SEQUENCE: 36
gcaaggccaa gugggaugc                                               19
```

```
<210> SEQ ID NO 37
<211> LENGTH: 19
<212> TYPE: RNA
<213> ORGANISM: Homo Sapiens
<220> FEATURE:

<400> SEQUENCE: 37
caaggccaag ugggaugcc                                               19
```

```
<210> SEQ ID NO 38
<211> LENGTH: 19
<212> TYPE: RNA
<213> ORGANISM: Homo Sapiens
<220> FEATURE:

<400> SEQUENCE: 38
aaggccaagu gggaugccu                                               19
```

```
<210> SEQ ID NO 39
<211> LENGTH: 19
<212> TYPE: RNA
<213> ORGANISM: Homo Sapiens
<220> FEATURE:

<400> SEQUENCE: 39
aggccaagug ggaugccug                                               19
```

```
<210> SEQ ID NO 40
<211> LENGTH: 19
<212> TYPE: RNA
<213> ORGANISM: Homo Sapiens
<220> FEATURE:

<400> SEQUENCE: 40
ggccaagugg gaugccugg                                               19
```

<210> SEQ ID NO 41
<211> LENGTH: 19
<212> TYPE: RNA
<213> ORGANISM: Homo Sapiens
<220> FEATURE:

<400> SEQUENCE: 41
gccaaguggg augccugga                                        19

<210> SEQ ID NO 42
<211> LENGTH: 19
<212> TYPE: RNA
<213> ORGANISM: Homo Sapiens
<220> FEATURE:

<400> SEQUENCE: 42
ccaaguggga ugccuggaa                                        19

<210> SEQ ID NO 43
<211> LENGTH: 19
<212> TYPE: RNA
<213> ORGANISM: Homo Sapiens
<220> FEATURE:

<400> SEQUENCE: 43
caagugggau gccuggaau                                        19

<210> SEQ ID NO 44
<211> LENGTH: 19
<212> TYPE: RNA
<213> ORGANISM: Homo Sapiens
<220> FEATURE:

<400> SEQUENCE: 44
aagugggaug ccuggaaug                                        19

<210> SEQ ID NO 45
<211> LENGTH: 19
<212> TYPE: RNA
<213> ORGANISM: Homo Sapiens
<220> FEATURE:

<400> SEQUENCE: 45
agugggaugc cuggaauga                                        19

<210> SEQ ID NO 46
<211> LENGTH: 19
<212> TYPE: RNA
<213> ORGANISM: Homo Sapiens
<220> FEATURE:

<400> SEQUENCE: 46
gugggaugcc uggaaugag                                        19

<210> SEQ ID NO 47
<211> LENGTH: 19
<212> TYPE: RNA
<213> ORGANISM: Homo Sapiens
<220> FEATURE:

<400> SEQUENCE: 47
ugggaugccu ggaaugagc                                        19

```
<210> SEQ ID NO 48
<211> LENGTH: 19
<212> TYPE: RNA
<213> ORGANISM: Homo Sapiens
<220> FEATURE:

<400> SEQUENCE: 48
gggaugccug gaaugagcu                                               19

<210> SEQ ID NO 49
<211> LENGTH: 19
<212> TYPE: RNA
<213> ORGANISM: Homo Sapiens
<220> FEATURE:

<400> SEQUENCE: 49
ggaugccugg aaugagcug                                               19

<210> SEQ ID NO 50
<211> LENGTH: 19
<212> TYPE: RNA
<213> ORGANISM: Homo Sapiens
<220> FEATURE:

<400> SEQUENCE: 50
gaugccugga augagcuga                                               19

<210> SEQ ID NO 51
<211> LENGTH: 19
<212> TYPE: RNA
<213> ORGANISM: Homo Sapiens
<220> FEATURE:

<400> SEQUENCE: 51
augccuggaa ugagcugaa                                               19

<210> SEQ ID NO 52
<211> LENGTH: 19
<212> TYPE: RNA
<213> ORGANISM: Homo Sapiens
<220> FEATURE:

<400> SEQUENCE: 52
ugccuggaau gagcugaaa                                               19

<210> SEQ ID NO 53
<211> LENGTH: 19
<212> TYPE: RNA
<213> ORGANISM: Homo Sapiens
<220> FEATURE:

<400> SEQUENCE: 53
gccuggaaug agcugaaag                                               19

<210> SEQ ID NO 54
<211> LENGTH: 19
<212> TYPE: RNA
<213> ORGANISM: Homo Sapiens
<220> FEATURE:

<400> SEQUENCE: 54
ccuggaauga gcugaaagg                                               19

<210> SEQ ID NO 55
<211> LENGTH: 19
```

```
<212> TYPE: RNA
<213> ORGANISM: Homo Sapiens
<220> FEATURE:

<400> SEQUENCE: 55
cuggaaugag cugaaaggg                                            19

<210> SEQ ID NO 56
<211> LENGTH: 19
<212> TYPE: RNA
<213> ORGANISM: Homo Sapiens
<220> FEATURE:

<400> SEQUENCE: 56
uggaaugagc ugaaaggga                                            19

<210> SEQ ID NO 57
<211> LENGTH: 19
<212> TYPE: RNA
<213> ORGANISM: Homo Sapiens
<220> FEATURE:

<400> SEQUENCE: 57
ggaaugagcu gaaagggac                                            19

<210> SEQ ID NO 58
<211> LENGTH: 19
<212> TYPE: RNA
<213> ORGANISM: Homo Sapiens
<220> FEATURE:

<400> SEQUENCE: 58
gaaugagcug aaagggacu                                            19

<210> SEQ ID NO 59
<211> LENGTH: 19
<212> TYPE: RNA
<213> ORGANISM: Homo Sapiens
<220> FEATURE:

<400> SEQUENCE: 59
aaugagcuga aagggacuu                                            19

<210> SEQ ID NO 60
<211> LENGTH: 19
<212> TYPE: RNA
<213> ORGANISM: Homo Sapiens
<220> FEATURE:

<400> SEQUENCE: 60
augagcugaa agggacuuc                                            19

<210> SEQ ID NO 61
<211> LENGTH: 19
<212> TYPE: RNA
<213> ORGANISM: Homo Sapiens
<220> FEATURE:

<400> SEQUENCE: 61
ugagcugaaa gggacuucc                                            19

<210> SEQ ID NO 62
<211> LENGTH: 19
<212> TYPE: RNA
<213> ORGANISM: Homo Sapiens
```

```
<220> FEATURE:

<400> SEQUENCE: 62
gagcugaaag ggacuucca                                                      19

<210> SEQ ID NO 63
<211> LENGTH: 19
<212> TYPE: RNA
<213> ORGANISM: Homo Sapiens
<220> FEATURE:

<400> SEQUENCE: 63
agcugaaagg gacuuccaa                                                      19

<210> SEQ ID NO 64
<211> LENGTH: 19
<212> TYPE: RNA
<213> ORGANISM: Homo Sapiens
<220> FEATURE:

<400> SEQUENCE: 64
gcugaaaggg acuuccaag                                                      19

<210> SEQ ID NO 65
<211> LENGTH: 19
<212> TYPE: RNA
<213> ORGANISM: Homo Sapiens
<220> FEATURE:

<400> SEQUENCE: 65
cugaaaggga cuuccaagg                                                      19

<210> SEQ ID NO 66
<211> LENGTH: 19
<212> TYPE: RNA
<213> ORGANISM: Homo Sapiens
<220> FEATURE:

<400> SEQUENCE: 66
ugaaagggac uuccaagga                                                      19

<210> SEQ ID NO 67
<211> LENGTH: 19
<212> TYPE: RNA
<213> ORGANISM: Homo Sapiens
<220> FEATURE:

<400> SEQUENCE: 67
gaaagggacu uccaaggaa                                                      19

<210> SEQ ID NO 68
<211> LENGTH: 19
<212> TYPE: RNA
<213> ORGANISM: Homo Sapiens
<220> FEATURE:

<400> SEQUENCE: 68
aaagggacuu ccaaggaag                                                      19

<210> SEQ ID NO 69
<211> LENGTH: 19
<212> TYPE: RNA
<213> ORGANISM: Homo Sapiens
<220> FEATURE:
```

-continued

```
<400> SEQUENCE: 69
aagggacuuc caaggaaga                                          19

<210> SEQ ID NO 70
<211> LENGTH: 19
<212> TYPE: RNA
<213> ORGANISM: Homo Sapiens
<220> FEATURE:

<400> SEQUENCE: 70
agggacuucc aaggaagau                                          19

<210> SEQ ID NO 71
<211> LENGTH: 19
<212> TYPE: RNA
<213> ORGANISM: Homo Sapiens
<220> FEATURE:

<400> SEQUENCE: 71
gggacuucca aggaagaug                                          19

<210> SEQ ID NO 72
<211> LENGTH: 19
<212> TYPE: RNA
<213> ORGANISM: Homo Sapiens
<220> FEATURE:

<400> SEQUENCE: 72
ggacuuccaa ggaagaugc                                          19

<210> SEQ ID NO 73
<211> LENGTH: 19
<212> TYPE: RNA
<213> ORGANISM: Homo Sapiens
<220> FEATURE:

<400> SEQUENCE: 73
gacuuccaag gaagaugcc                                          19

<210> SEQ ID NO 74
<211> LENGTH: 19
<212> TYPE: RNA
<213> ORGANISM: Homo Sapiens
<220> FEATURE:

<400> SEQUENCE: 74
acuuccaagg aagaugcca                                          19

<210> SEQ ID NO 75
<211> LENGTH: 19
<212> TYPE: RNA
<213> ORGANISM: Homo Sapiens
<220> FEATURE:

<400> SEQUENCE: 75
cuuccaagga agaugccau                                          19

<210> SEQ ID NO 76
<211> LENGTH: 19
<212> TYPE: RNA
<213> ORGANISM: Homo Sapiens
<220> FEATURE:

<400> SEQUENCE: 76
```

|  |  |
|---|---|
| uuccaaggaa gaugccaug | 19 |

<210> SEQ ID NO 77
<211> LENGTH: 19
<212> TYPE: RNA
<213> ORGANISM: Homo Sapiens
<220> FEATURE:

<400> SEQUENCE: 77

| | |
|---|---|
| uccaaggaag augccauga | 19 |

<210> SEQ ID NO 78
<211> LENGTH: 19
<212> TYPE: RNA
<213> ORGANISM: Homo Sapiens
<220> FEATURE:

<400> SEQUENCE: 78

| | |
|---|---|
| ccaaggaaga ugccaugaa | 19 |

<210> SEQ ID NO 79
<211> LENGTH: 19
<212> TYPE: RNA
<213> ORGANISM: Homo Sapiens
<220> FEATURE:

<400> SEQUENCE: 79

| | |
|---|---|
| caaggaagau gccaugaaa | 19 |

<210> SEQ ID NO 80
<211> LENGTH: 19
<212> TYPE: RNA
<213> ORGANISM: Homo Sapiens
<220> FEATURE:

<400> SEQUENCE: 80

| | |
|---|---|
| aaggaagaug ccaugaaag | 19 |

<210> SEQ ID NO 81
<211> LENGTH: 19
<212> TYPE: RNA
<213> ORGANISM: Homo Sapiens
<220> FEATURE:

<400> SEQUENCE: 81

| | |
|---|---|
| aggaagaugc caugaaagc | 19 |

<210> SEQ ID NO 82
<211> LENGTH: 19
<212> TYPE: RNA
<213> ORGANISM: Homo Sapiens
<220> FEATURE:

<400> SEQUENCE: 82

| | |
|---|---|
| ggaagaugcc augaaagcu | 19 |

<210> SEQ ID NO 83
<211> LENGTH: 19
<212> TYPE: RNA
<213> ORGANISM: Homo Sapiens
<220> FEATURE:

<400> SEQUENCE: 83

| | |
|---|---|
| gaagaugcca ugaaagcuu | 19 |

```
<210> SEQ ID NO 84
<211> LENGTH: 19
<212> TYPE: RNA
<213> ORGANISM: Homo Sapiens
<220> FEATURE:

<400> SEQUENCE: 84
aagaugccau gaaagcuua                                                   19

<210> SEQ ID NO 85
<211> LENGTH: 19
<212> TYPE: RNA
<213> ORGANISM: Homo Sapiens
<220> FEATURE:

<400> SEQUENCE: 85
agaugccaug aaagcuuac                                                   19

<210> SEQ ID NO 86
<211> LENGTH: 19
<212> TYPE: RNA
<213> ORGANISM: Homo Sapiens
<220> FEATURE:

<400> SEQUENCE: 86
gaugccauga aagcuuaca                                                   19

<210> SEQ ID NO 87
<211> LENGTH: 19
<212> TYPE: RNA
<213> ORGANISM: Homo Sapiens
<220> FEATURE:

<400> SEQUENCE: 87
augccaugaa agcuuacau                                                   19

<210> SEQ ID NO 88
<211> LENGTH: 19
<212> TYPE: RNA
<213> ORGANISM: Homo Sapiens
<220> FEATURE:

<400> SEQUENCE: 88
ugccaugaaa gcuuacauc                                                   19

<210> SEQ ID NO 89
<211> LENGTH: 19
<212> TYPE: RNA
<213> ORGANISM: Homo Sapiens
<220> FEATURE:

<400> SEQUENCE: 89
gccaugaaag cuuacauca                                                   19

<210> SEQ ID NO 90
<211> LENGTH: 19
<212> TYPE: RNA
<213> ORGANISM: Homo Sapiens
<220> FEATURE:

<400> SEQUENCE: 90
ccaugaaagc uuacaucaa                                                   19

<210> SEQ ID NO 91
```

```
<211> LENGTH: 19
<212> TYPE: RNA
<213> ORGANISM: Homo Sapiens
<220> FEATURE:

<400> SEQUENCE: 91
caugaaagcu uacaucaac                                                    19

<210> SEQ ID NO 92
<211> LENGTH: 19
<212> TYPE: RNA
<213> ORGANISM: Homo Sapiens
<220> FEATURE:

<400> SEQUENCE: 92
augaaagcuu acaucaaca                                                    19

<210> SEQ ID NO 93
<211> LENGTH: 19
<212> TYPE: RNA
<213> ORGANISM: Homo Sapiens
<220> FEATURE:

<400> SEQUENCE: 93
ugaaagcuua caucaacaa                                                    19

<210> SEQ ID NO 94
<211> LENGTH: 19
<212> TYPE: RNA
<213> ORGANISM: Homo Sapiens
<220> FEATURE:

<400> SEQUENCE: 94
gaaagcuuac aucaacaaa                                                    19

<210> SEQ ID NO 95
<211> LENGTH: 19
<212> TYPE: RNA
<213> ORGANISM: Homo Sapiens
<220> FEATURE:

<400> SEQUENCE: 95
aaagcuuaca ucaacaaag                                                    19

<210> SEQ ID NO 96
<211> LENGTH: 19
<212> TYPE: RNA
<213> ORGANISM: Homo Sapiens
<220> FEATURE:

<400> SEQUENCE: 96
aagcuuacau caacaaagu                                                    19

<210> SEQ ID NO 97
<211> LENGTH: 19
<212> TYPE: RNA
<213> ORGANISM: Homo Sapiens
<220> FEATURE:

<400> SEQUENCE: 97
agcuuacauc aacaaagua                                                    19

<210> SEQ ID NO 98
<211> LENGTH: 19
<212> TYPE: RNA
```

```
<213> ORGANISM: Homo Sapiens
<220> FEATURE:

<400> SEQUENCE: 98
gcuuacauca acaaaguag                                                       19

<210> SEQ ID NO 99
<211> LENGTH: 19
<212> TYPE: RNA
<213> ORGANISM: Homo Sapiens
<220> FEATURE:

<400> SEQUENCE: 99
cuuacaucaa caaaguaga                                                       19

<210> SEQ ID NO 100
<211> LENGTH: 19
<212> TYPE: RNA
<213> ORGANISM: Homo Sapiens
<220> FEATURE:

<400> SEQUENCE: 100
uuacaucaac aaaguagaa                                                       19

<210> SEQ ID NO 101
<211> LENGTH: 19
<212> TYPE: RNA
<213> ORGANISM: Homo Sapiens
<220> FEATURE:

<400> SEQUENCE: 101
uacaucaaca aaguagaag                                                       19

<210> SEQ ID NO 102
<211> LENGTH: 19
<212> TYPE: RNA
<213> ORGANISM: Homo Sapiens
<220> FEATURE:

<400> SEQUENCE: 102
acaucaacaa aguagaaga                                                       19

<210> SEQ ID NO 103
<211> LENGTH: 19
<212> TYPE: RNA
<213> ORGANISM: Homo Sapiens
<220> FEATURE:

<400> SEQUENCE: 103
caucaacaaa guagaagag                                                       19

<210> SEQ ID NO 104
<211> LENGTH: 19
<212> TYPE: RNA
<213> ORGANISM: Homo Sapiens
<220> FEATURE:

<400> SEQUENCE: 104
aucaacaaag uagaagagc                                                       19

<210> SEQ ID NO 105
<211> LENGTH: 19
<212> TYPE: RNA
<213> ORGANISM: Homo Sapiens
<220> FEATURE:
```

```
<400> SEQUENCE: 105
ucaacaaagu agaagagcu                                                   19

<210> SEQ ID NO 106
<211> LENGTH: 19
<212> TYPE: RNA
<213> ORGANISM: Homo Sapiens
<220> FEATURE:

<400> SEQUENCE: 106
caacaaagua gaagagcua                                                   19

<210> SEQ ID NO 107
<211> LENGTH: 19
<212> TYPE: RNA
<213> ORGANISM: Homo Sapiens
<220> FEATURE:

<400> SEQUENCE: 107
aacaaaguag aagagcuaa                                                   19

<210> SEQ ID NO 108
<211> LENGTH: 19
<212> TYPE: RNA
<213> ORGANISM: Homo Sapiens
<220> FEATURE:

<400> SEQUENCE: 108
acaaaguaga agagcuaaa                                                   19

<210> SEQ ID NO 109
<211> LENGTH: 19
<212> TYPE: RNA
<213> ORGANISM: Homo Sapiens
<220> FEATURE:

<400> SEQUENCE: 109
caaaguagaa gagcuaaag                                                   19

<210> SEQ ID NO 110
<211> LENGTH: 19
<212> TYPE: RNA
<213> ORGANISM: Homo Sapiens
<220> FEATURE:

<400> SEQUENCE: 110
aaaguagaag agcuaaaga                                                   19

<210> SEQ ID NO 111
<211> LENGTH: 19
<212> TYPE: RNA
<213> ORGANISM: Homo Sapiens
<220> FEATURE:

<400> SEQUENCE: 111
aaguagaaga gcuaaagaa                                                   19

<210> SEQ ID NO 112
<211> LENGTH: 19
<212> TYPE: RNA
<213> ORGANISM: Homo Sapiens
<220> FEATURE:

<400> SEQUENCE: 112
```

```
aguagaagag cuaaagaaa                                                19

<210> SEQ ID NO 113
<211> LENGTH: 19
<212> TYPE: RNA
<213> ORGANISM: Homo Sapiens
<220> FEATURE:

<400> SEQUENCE: 113
guagaagagc uaagaaaa                                                 19

<210> SEQ ID NO 114
<211> LENGTH: 19
<212> TYPE: RNA
<213> ORGANISM: Homo Sapiens
<220> FEATURE:

<400> SEQUENCE: 114
uagaagagcu aagaaaaa                                                 19

<210> SEQ ID NO 115
<211> LENGTH: 19
<212> TYPE: RNA
<213> ORGANISM: Homo Sapiens
<220> FEATURE:

<400> SEQUENCE: 115
agaagagcua agaaaaaa                                                 19

<210> SEQ ID NO 116
<211> LENGTH: 19
<212> TYPE: RNA
<213> ORGANISM: Homo Sapiens
<220> FEATURE:

<400> SEQUENCE: 116
gaagagcuaa agaaaaau                                                 19

<210> SEQ ID NO 117
<211> LENGTH: 19
<212> TYPE: RNA
<213> ORGANISM: Homo Sapiens
<220> FEATURE:

<400> SEQUENCE: 117
aagagcuaaa gaaaaaua                                                 19

<210> SEQ ID NO 118
<211> LENGTH: 19
<212> TYPE: RNA
<213> ORGANISM: Homo Sapiens
<220> FEATURE:

<400> SEQUENCE: 118
agagcuaaag aaaaauac                                                 19

<210> SEQ ID NO 119
<211> LENGTH: 19
<212> TYPE: RNA
<213> ORGANISM: Homo Sapiens
<220> FEATURE:

<400> SEQUENCE: 119
gagcuaaaga aaaauacg                                                 19
```

-continued

<210> SEQ ID NO 120
<211> LENGTH: 19
<212> TYPE: RNA
<213> ORGANISM: Homo Sapiens
<220> FEATURE:

<400> SEQUENCE: 120
agcuaaagaa aaauacgg                                              19

<210> SEQ ID NO 121
<211> LENGTH: 19
<212> TYPE: RNA
<213> ORGANISM: Homo Sapiens
<220> FEATURE:

<400> SEQUENCE: 121
gcuaaagaaa aaauacggg                                             19

<210> SEQ ID NO 122
<211> LENGTH: 19
<212> TYPE: RNA
<213> ORGANISM: Homo Sapiens
<220> FEATURE:

<400> SEQUENCE: 122
gaaguacauc cauuauaag                                             19

<210> SEQ ID NO 123
<211> LENGTH: 19
<212> TYPE: RNA
<213> ORGANISM: Homo Sapiens
<220> FEATURE:

<400> SEQUENCE: 123
aaacagaucu uuacaagcu                                             19

<210> SEQ ID NO 124
<211> LENGTH: 19
<212> TYPE: RNA
<213> ORGANISM: Homo Sapiens
<220> FEATURE:

<400> SEQUENCE: 124
uuucaagugu cuccuaaua                                             19

<210> SEQ ID NO 125
<211> LENGTH: 19
<212> TYPE: RNA
<213> ORGANISM: Homo Sapiens
<220> FEATURE:

<400> SEQUENCE: 125
gcaaagaaca ucauccaua                                             19

<210> SEQ ID NO 126
<211> LENGTH: 19
<212> TYPE: RNA
<213> ORGANISM: Homo Sapiens
<220> FEATURE:

<400> SEQUENCE: 126
gcagagagag cagauuuga                                             19

```
<210> SEQ ID NO 127
<211> LENGTH: 19
<212> TYPE: RNA
<213> ORGANISM: Homo Sapiens
<220> FEATURE:

<400> SEQUENCE: 127
ucaaggaacu cgaucguau                                                    19

<210> SEQ ID NO 128
<211> LENGTH: 19
<212> TYPE: RNA
<213> ORGANISM: Homo Sapiens
<220> FEATURE:

<400> SEQUENCE: 128
gacaugaaau ccaacaaua                                                    19

<210> SEQ ID NO 129
<211> LENGTH: 19
<212> TYPE: RNA
<213> ORGANISM: Homo Sapiens
<220> FEATURE:

<400> SEQUENCE: 129
ucaagugucu ccuaauaug                                                    19

<210> SEQ ID NO 130
<211> LENGTH: 19
<212> TYPE: RNA
<213> ORGANISM: Homo Sapiens
<220> FEATURE:

<400> SEQUENCE: 130
caaagacgau gacuucgaa                                                    19

<210> SEQ ID NO 131
<211> LENGTH: 19
<212> TYPE: RNA
<213> ORGANISM: Homo Sapiens
<220> FEATURE:

<400> SEQUENCE: 131
ggaagcugau ccaccuuga                                                    19

<210> SEQ ID NO 132
<211> LENGTH: 19
<212> TYPE: RNA
<213> ORGANISM: Homo Sapiens
<220> FEATURE:

<400> SEQUENCE: 132
caagaggauu gaaguagaa                                                    19

<210> SEQ ID NO 133
<211> LENGTH: 19
<212> TYPE: RNA
<213> ORGANISM: Homo Sapiens
<220> FEATURE:

<400> SEQUENCE: 133
ccaaagcucu ggacuuauu                                                    19

<210> SEQ ID NO 134
<211> LENGTH: 19
```

-continued

```
<212> TYPE: RNA
<213> ORGANISM: Homo Sapiens
<220> FEATURE:

<400> SEQUENCE: 134
guacgacaac cgggagaua                                              19

<210> SEQ ID NO 135
<211> LENGTH: 19
<212> TYPE: RNA
<213> ORGANISM: Homo Sapiens
<220> FEATURE:

<400> SEQUENCE: 135
agauagugau gaaguacau                                              19

<210> SEQ ID NO 136
<211> LENGTH: 19
<212> TYPE: RNA
<213> ORGANISM: Homo Sapiens
<220> FEATURE:

<400> SEQUENCE: 136
gggagauagu gaugaagua                                              19

<210> SEQ ID NO 137
<211> LENGTH: 19
<212> TYPE: RNA
<213> ORGANISM: Homo Sapiens
<220> FEATURE:

<400> SEQUENCE: 137
gaaaugauug cacuauuga                                              19

<210> SEQ ID NO 138
<211> LENGTH: 19
<212> TYPE: RNA
<213> ORGANISM: Homo Sapiens
<220> FEATURE:

<400> SEQUENCE: 138
gcacggagau guugcagua                                              19

<210> SEQ ID NO 139
<211> LENGTH: 19
<212> TYPE: RNA
<213> ORGANISM: Homo Sapiens
<220> FEATURE:

<400> SEQUENCE: 139
gcuacuaucu gauuuacug                                              19

<210> SEQ ID NO 140
<211> LENGTH: 19
<212> TYPE: RNA
<213> ORGANISM: Homo Sapiens
<220> FEATURE:

<400> SEQUENCE: 140
caagggaggu uacaccaaa                                              19

<210> SEQ ID NO 141
<211> LENGTH: 19
<212> TYPE: RNA
<213> ORGANISM: Homo Sapiens
```

-continued

```
<220> FEATURE:

<400> SEQUENCE: 141
gagguucucu ggaucaagu                                               19

<210> SEQ ID NO 142
<211> LENGTH: 19
<212> TYPE: RNA
<213> ORGANISM: Homo Sapiens
<220> FEATURE:

<400> SEQUENCE: 142
gcuacacgca guugcagua                                               19

<210> SEQ ID NO 143
<211> LENGTH: 19
<212> TYPE: RNA
<213> ORGANISM: Homo Sapiens
<220> FEATURE:

<400> SEQUENCE: 143
agacugaccu guacaaguu                                               19

<210> SEQ ID NO 144
<211> LENGTH: 19
<212> TYPE: RNA
<213> ORGANISM: Homo Sapiens
<220> FEATURE:

<400> SEQUENCE: 144
gaucagcauu ugcauggaa                                               19

<210> SEQ ID NO 145
<211> LENGTH: 19
<212> TYPE: RNA
<213> ORGANISM: Homo Sapiens
<220> FEATURE:

<400> SEQUENCE: 145
ggaacucgau cguaucauu                                               19

<210> SEQ ID NO 146
<211> LENGTH: 19
<212> TYPE: RNA
<213> ORGANISM: Homo Sapiens
<220> FEATURE:

<400> SEQUENCE: 146
cgacaagacu gccgagaga                                               19

<210> SEQ ID NO 147
<211> LENGTH: 19
<212> TYPE: RNA
<213> ORGANISM: Homo Sapiens
<220> FEATURE:

<400> SEQUENCE: 147
gagccuuacu gccuuugua                                               19

<210> SEQ ID NO 148
<211> LENGTH: 19
<212> TYPE: RNA
<213> ORGANISM: Homo Sapiens
<220> FEATURE:
```

```
<400> SEQUENCE: 148
cugaagaaag cauugacua                                              19

<210> SEQ ID NO 149
<211> LENGTH: 19
<212> TYPE: RNA
<213> ORGANISM: Homo Sapiens
<220> FEATURE:

<400> SEQUENCE: 149
ggccggaggc gcuuuacua                                              19

<210> SEQ ID NO 150
<211> LENGTH: 19
<212> TYPE: RNA
<213> ORGANISM: Homo Sapiens
<220> FEATURE:

<400> SEQUENCE: 150
guacagggcu ccagaaauu                                              19

<210> SEQ ID NO 151
<211> LENGTH: 19
<212> TYPE: RNA
<213> ORGANISM: Homo Sapiens
<220> FEATURE:

<400> SEQUENCE: 151
ucgacgcagu ggacauuaa                                              19

<210> SEQ ID NO 152
<211> LENGTH: 19
<212> TYPE: RNA
<213> ORGANISM: Homo Sapiens
<220> FEATURE:

<400> SEQUENCE: 152
aacuagaagu auguugcua                                              19

<210> SEQ ID NO 153
<211> LENGTH: 19
<212> TYPE: RNA
<213> ORGANISM: Homo Sapiens
<220> FEATURE:

<400> SEQUENCE: 153
gaccggaugu uaaccuuua                                              19

<210> SEQ ID NO 154
<211> LENGTH: 19
<212> TYPE: RNA
<213> ORGANISM: Homo Sapiens
<220> FEATURE:

<400> SEQUENCE: 154 uuggugucu ucuuauuua                                               19

<210> SEQ ID NO 155
<211> LENGTH: 19
<212> TYPE: RNA
<213> ORGANISM: Homo Sapiens
<220> FEATURE:

<400> SEQUENCE: 155
```

-continued

| | |
|---|---|
| aauggcuuug aaucuuugg | 19 |

<210> SEQ ID NO 156
<211> LENGTH: 19
<212> TYPE: RNA
<213> ORGANISM: Homo Sapiens
<220> FEATURE:

<400> SEQUENCE: 156

| | |
|---|---|
| gcacauggau ggagguucu | 19 |

<210> SEQ ID NO 157
<211> LENGTH: 19
<212> TYPE: RNA
<213> ORGANISM: Homo Sapiens
<220> FEATURE:

<400> SEQUENCE: 157

| | |
|---|---|
| ggauucaguu ggagugauu | 19 |

<210> SEQ ID NO 158
<211> LENGTH: 19
<212> TYPE: RNA
<213> ORGANISM: Homo Sapiens
<220> FEATURE:

<400> SEQUENCE: 158

| | |
|---|---|
| caaagaacau cauccauag | 19 |

<210> SEQ ID NO 159
<211> LENGTH: 19
<212> TYPE: RNA
<213> ORGANISM: Homo Sapiens
<220> FEATURE:

<400> SEQUENCE: 159

| | |
|---|---|
| gaaagccuau gccacuguu | 19 |

<210> SEQ ID NO 160
<211> LENGTH: 19
<212> TYPE: RNA
<213> ORGANISM: Homo Sapiens
<220> FEATURE:

<400> SEQUENCE: 160

| | |
|---|---|
| gcuaugcccu ggccacuug | 19 |

<210> SEQ ID NO 161
<211> LENGTH: 19
<212> TYPE: RNA
<213> ORGANISM: Homo Sapiens
<220> FEATURE:

<400> SEQUENCE: 161

| | |
|---|---|
| gagcagauuu gaagcaacu | 19 |

<210> SEQ ID NO 162
<211> LENGTH: 19
<212> TYPE: RNA
<213> ORGANISM: Homo Sapiens
<220> FEATURE:

<400> SEQUENCE: 162

| | |
|---|---|
| uaacugcagc caacuauuu | 19 |

```
<210> SEQ ID NO 163
<211> LENGTH: 19
<212> TYPE: RNA
<213> ORGANISM: Homo Sapiens
<220> FEATURE:

<400> SEQUENCE: 163
auguuuacua ccaaaugga                                                   19

<210> SEQ ID NO 164
<211> LENGTH: 19
<212> TYPE: RNA
<213> ORGANISM: Homo Sapiens
<220> FEATURE:

<400> SEQUENCE: 164
uccaggaguu ugucaauaa                                                   19

<210> SEQ ID NO 165
<211> LENGTH: 19
<212> TYPE: RNA
<213> ORGANISM: Homo Sapiens
<220> FEATURE:

<400> SEQUENCE: 165
gcagauacuu gagccauug                                                   19

<210> SEQ ID NO 166
<211> LENGTH: 19
<212> TYPE: RNA
<213> ORGANISM: Homo Sapiens
<220> FEATURE:

<400> SEQUENCE: 166
gaaacuaccu acagucucu                                                   19

<210> SEQ ID NO 167
<211> LENGTH: 19
<212> TYPE: RNA
<213> ORGANISM: Homo Sapiens
<220> FEATURE:

<400> SEQUENCE: 167
ccggaaauuu gaagaguau                                                   19

<210> SEQ ID NO 168
<211> LENGTH: 19
<212> TYPE: RNA
<213> ORGANISM: Homo Sapiens
<220> FEATURE:

<400> SEQUENCE: 168
gaacaccgag ugccaagaa                                                   19

<210> SEQ ID NO 169
<211> LENGTH: 19
<212> TYPE: RNA
<213> ORGANISM: Homo Sapiens
<220> FEATURE:

<400> SEQUENCE: 169
ggacauuugu guacucacu                                                   19

<210> SEQ ID NO 170
```

```
<211> LENGTH: 19
<212> TYPE: RNA
<213> ORGANISM: Homo Sapiens
<220> FEATURE:

<400> SEQUENCE: 170
gcacauggau ggagguucu                                               19

<210> SEQ ID NO 171
<211> LENGTH: 19
<212> TYPE: RNA
<213> ORGANISM: Homo Sapiens
<220> FEATURE:

<400> SEQUENCE: 171
gcagagagag cagauuuga                                               19

<210> SEQ ID NO 172
<211> LENGTH: 19
<212> TYPE: RNA
<213> ORGANISM: Homo Sapiens
<220> FEATURE:

<400> SEQUENCE: 172
gagguucucu ggaucaagu                                               19

<210> SEQ ID NO 173
<211> LENGTH: 19
<212> TYPE: RNA
<213> ORGANISM: Homo Sapiens
<220> FEATURE:

<400> SEQUENCE: 173
gagcagauuu gaagcaacu                                               19

<210> SEQ ID NO 174
<211> LENGTH: 19
<212> TYPE: RNA
<213> ORGANISM: Homo Sapiens
<220> FEATURE:

<400> SEQUENCE: 174
caaagacgau gacuucgaa                                               19

<210> SEQ ID NO 175
<211> LENGTH: 19
<212> TYPE: RNA
<213> ORGANISM: Homo Sapiens
<220> FEATURE:

<400> SEQUENCE: 175
gaucagcauu ugcauggaa                                               19

<210> SEQ ID NO 176
<211> LENGTH: 19
<212> TYPE: RNA
<213> ORGANISM: Homo Sapiens
<220> FEATURE:

<400> SEQUENCE: 176
uccaggaguu ugucaauaa                                               19

<210> SEQ ID NO 177
<211> LENGTH: 19
<212> TYPE: RNA
```

-continued

```
<213> ORGANISM: Homo Sapiens
<220> FEATURE:

<400> SEQUENCE: 177
ggaagcugau ccaccuuga                                              19

<210> SEQ ID NO 178
<211> LENGTH: 19
<212> TYPE: RNA
<213> ORGANISM: Homo Sapiens
<220> FEATURE:

<400> SEQUENCE: 178
uccaggaguu ugucaauaa                                              19

<210> SEQ ID NO 179
<211> LENGTH: 19
<212> TYPE: RNA
<213> ORGANISM: Homo Sapiens
<220> FEATURE:

<400> SEQUENCE: 179
gcagauacuu gagccauug                                              19

<210> SEQ ID NO 180
<211> LENGTH: 19
<212> TYPE: RNA
<213> ORGANISM: Homo Sapiens
<220> FEATURE:

<400> SEQUENCE: 180
ccggaaauuu gaagaguau                                              19

<210> SEQ ID NO 181
<211> LENGTH: 19
<212> TYPE: RNA
<213> ORGANISM: Homo Sapiens
<220> FEATURE:

<400> SEQUENCE: 181
ggacauuugu guacucacu                                              19

<210> SEQ ID NO 182
<211> LENGTH: 19
<212> TYPE: RNA
<213> ORGANISM: Homo Sapiens
<220> FEATURE:

<400> SEQUENCE: 182
gaaacgagau uccuucauc                                              19

<210> SEQ ID NO 183
<211> LENGTH: 19
<212> TYPE: RNA
<213> ORGANISM: Homo Sapiens
<220> FEATURE:

<400> SEQUENCE: 183
caagaucggu uuuggcaua                                              19

<210> SEQ ID NO 184
<211> LENGTH: 19
<212> TYPE: RNA
<213> ORGANISM: Homo Sapiens
<220> FEATURE:
```

-continued

```
<400> SEQUENCE: 184
caaacaaucu gugacuauu                                               19

<210> SEQ ID NO 185
<211> LENGTH: 19
<212> TYPE: RNA
<213> ORGANISM: Homo Sapiens
<220> FEATURE:

<400> SEQUENCE: 185
caacuuguuu gacgacgaa                                               19

<210> SEQ ID NO 186
<211> LENGTH: 19
<212> TYPE: RNA
<213> ORGANISM: Homo Sapiens
<220> FEATURE:

<400> SEQUENCE: 186
gaaaggauuu ggcuacaaa                                               19

<210> SEQ ID NO 187
<211> LENGTH: 19
<212> TYPE: RNA
<213> ORGANISM: Homo Sapiens
<220> FEATURE:

<400> SEQUENCE: 187
gagcauguuu acaacguuu                                               19

<210> SEQ ID NO 188
<211> LENGTH: 19
<212> TYPE: RNA
<213> ORGANISM: Homo Sapiens
<220> FEATURE:

<400> SEQUENCE: 188
ggaaagacug uuccaaaaa                                               19

<210> SEQ ID NO 189
<211> LENGTH: 19
<212> TYPE: RNA
<213> ORGANISM: Homo Sapiens
<220> FEATURE:

<400> SEQUENCE: 189
acauuuacau ucucuugga                                               19

<210> SEQ ID NO 190
<211> LENGTH: 19
<212> TYPE: RNA
<213> ORGANISM: Homo Sapiens
<220> FEATURE:

<400> SEQUENCE: 190
gaaagagcau cuacgguga                                               19

<210> SEQ ID NO 191
<211> LENGTH: 19
<212> TYPE: RNA
<213> ORGANISM: Homo Sapiens
<220> FEATURE:

<400> SEQUENCE: 191
```

-continued acaaggagau uuauaccua                                                   19

<210> SEQ ID NO 192
<211> LENGTH: 19
<212> TYPE: RNA
<213> ORGANISM: Homo Sapiens
<220> FEATURE:

<400> SEQUENCE: 192
aggaacauuu ggagaguua                                                   19

<210> SEQ ID NO 193
<211> LENGTH: 19
<212> TYPE: RNA
<213> ORGANISM: Homo Sapiens
<220> FEATURE:

<400> SEQUENCE: 193
caucguuuau agagacuua                                                   19

<210> SEQ ID NO 194
<211> LENGTH: 19
<212> TYPE: RNA
<213> ORGANISM: Homo Sapiens
<220> FEATURE:

<400> SEQUENCE: 194
gaaaguaagc agaaucuau                                                   19

<210> SEQ ID NO 195
<211> LENGTH: 19
<212> TYPE: RNA
<213> ORGANISM: Coronaviridae Sars coronavirus
<220> FEATURE:

<400> SEQUENCE: 195
aaccaacggu uuacgucua 19

<210> SEQ ID NO 196
<211> LENGTH: 19
<212> TYPE: RNA
<213> ORGANISM: Homo Sapiens
<220> FEATURE:

<400> SEQUENCE: 196
gaaagacaag agaccaaua 19

<210> SEQ ID NO 197
<211> LENGTH: 19
<212> TYPE: RNA
<213> ORGANISM: Homo Sapiens
<220> FEATURE:

<400> SEQUENCE: 197
caacagcgau uuuaggaua 19

<210> SEQ ID NO 198
<211> LENGTH: 19
<212> TYPE: RNA
<213> ORGANISM: Homo Sapiens
<220> FEATURE:

<400> SEQUENCE: 198
ggaaacagcu gcucauuca 19

<210> SEQ ID NO 199
<211> LENGTH: 19
<212> TYPE: RNA
<213> ORGANISM: Homo Sapiens
<220> FEATURE:

<400> SEQUENCE: 199
acauuuggcu gugauggua                                                    19

<210> SEQ ID NO 200
<211> LENGTH: 19
<212> TYPE: RNA
<213> ORGANISM: Homo Sapiens
<220> FEATURE:

<400> SEQUENCE: 200
gaaacuacaa cuuacauga                                                    19

<210> SEQ ID NO 201
<211> LENGTH: 19
<212> TYPE: RNA
<213> ORGANISM: Homo Sapiens
<220> FEATURE:

<400> SEQUENCE: 201
gaugauguuu uccuacuuu                                                    19

<210> SEQ ID NO 202
<211> LENGTH: 19
<212> TYPE: RNA
<213> ORGANISM: Homo Sapiens
<220> FEATURE:

<400> SEQUENCE: 202
agaauuugcg auguacuua                                                    19

<210> SEQ ID NO 203
<211> LENGTH: 19
<212> TYPE: RNA
<213> ORGANISM: Homo Sapiens
<220> FEATURE:

<400> SEQUENCE: 203
agguuugcuu gauguuaca                                                    19

<210> SEQ ID NO 204
<211> LENGTH: 19
<212> TYPE: RNA
<213> ORGANISM: Cytomegalovirus Human herpesvirdae
<220> FEATURE:

<400> SEQUENCE: 204
cgaaaggucu uaccggaaa                                                    19

<210> SEQ ID NO 205
<211> LENGTH: 19
<212> TYPE: RNA
<213> ORGANISM: Homo Sapiens
<220> FEATURE:

<400> SEQUENCE: 205
caaagaguau gucgaauca                                                    19

```
<210> SEQ ID NO 206
<211> LENGTH: 19
<212> TYPE: RNA
<213> ORGANISM: Homo Sapiens
<220> FEATURE:

<400> SEQUENCE: 206
aaggaaagcu gacugauaa                                                    19

<210> SEQ ID NO 207
<211> LENGTH: 19
<212> TYPE: RNA
<213> ORGANISM: Homo Sapiens
<220> FEATURE:

<400> SEQUENCE: 207
caucaaagcu gccauggaa                                                    19

<210> SEQ ID NO 208
<211> LENGTH: 19
<212> TYPE: RNA
<213> ORGANISM: Homo Sapiens
<220> FEATURE:

<400> SEQUENCE: 208
cagcauuuaa cgucauaug                                                    19

<210> SEQ ID NO 209
<211> LENGTH: 19
<212> TYPE: RNA
<213> ORGANISM: Homo Sapiens
<220> FEATURE:

<400> SEQUENCE: 209
auugcguuua cacuuacag                                                    19

<210> SEQ ID NO 210
<211> LENGTH: 19
<212> TYPE: RNA
<213> ORGANISM: Homo Sapiens
<220> FEATURE:

<400> SEQUENCE: 210
gaucaaaggu uuucacuaa                                                    19

<210> SEQ ID NO 211
<211> LENGTH: 19
<212> TYPE: RNA
<213> ORGANISM: Homo Sapiens
<220> FEATURE:

<400> SEQUENCE: 211
caaaccagcg cgcuaauga                                                    19

<210> SEQ ID NO 212
<211> LENGTH: 19
<212> TYPE: RNA
<213> ORGANISM: Homo Sapiens
<220> FEATURE:

<400> SEQUENCE: 212
caaacagcgu cuccuggaa                                                    19

<210> SEQ ID NO 213
<211> LENGTH: 19
```

-continued

```
<212> TYPE: RNA
<213> ORGANISM: Homo Sapiens
<220> FEATURE:

<400> SEQUENCE: 213
gaaagcauau acagcaauu                                                    19

<210> SEQ ID NO 214
<211> LENGTH: 19
<212> TYPE: RNA
<213> ORGANISM: Homo Sapiens
<220> FEATURE:

<400> SEQUENCE: 214
caaagaagau aaccaaugu                                                    19

<210> SEQ ID NO 215
<211> LENGTH: 19
<212> TYPE: RNA
<213> ORGANISM: Homo Sapiens
<220> FEATURE:

<400> SEQUENCE: 215
gaaacauccu ccggcugaa                                                    19

<210> SEQ ID NO 216
<211> LENGTH: 19
<212> TYPE: RNA
<213> ORGANISM: Homo Sapiens
<220> FEATURE:

<400> SEQUENCE: 216
gagcagauuu uaagaguaa                                                    19

<210> SEQ ID NO 217
<211> LENGTH: 19
<212> TYPE: RNA
<213> ORGANISM: Homo Sapiens
<220> FEATURE:

<400> SEQUENCE: 217
ggacaauuuu gcagcaaca                                                    19

<210> SEQ ID NO 218
<211> LENGTH: 19
<212> TYPE: RNA
<213> ORGANISM: Homo Sapiens
<220> FEATURE:

<400> SEQUENCE: 218
caaaggugcu gcugaugua                                                    19

<210> SEQ ID NO 219
<211> LENGTH: 19
<212> TYPE: RNA
<213> ORGANISM: Homo Sapiens
<220> FEATURE:

<400> SEQUENCE: 219
acaucauuua cggcaugua                                                    19

<210> SEQ ID NO 220
<211> LENGTH: 19
<212> TYPE: RNA
<213> ORGANISM: Homo Sapiens
```

```
<220> FEATURE:

<400> SEQUENCE: 220
ccacaccgcu ggccaagaa                                                19

<210> SEQ ID NO 221
<211> LENGTH: 19
<212> TYPE: RNA
<213> ORGANISM: Homo Sapiens
<220> FEATURE:

<400> SEQUENCE: 221
uaucaagccu gccauaug                                                 19

<210> SEQ ID NO 222
<211> LENGTH: 19
<212> TYPE: RNA
<213> ORGANISM: Homo Sapiens
<220> FEATURE:

<400> SEQUENCE: 222
ucaauaagcc aucuucuaa                                                19

<210> SEQ ID NO 223
<211> LENGTH: 19
<212> TYPE: RNA
<213> ORGANISM: Homo Sapiens
<220> FEATURE:

<400> SEQUENCE: 223
gagcuaaucu gccacauug                                                19

<210> SEQ ID NO 224
<211> LENGTH: 19
<212> TYPE: RNA
<213> ORGANISM: Homo Sapiens
<220> FEATURE:

<400> SEQUENCE: 224
cgaaggcggu ggccaauca                                                19

<210> SEQ ID NO 225
<211> LENGTH: 19
<212> TYPE: RNA
<213> ORGANISM: Homo Sapiens
<220> FEATURE:

<400> SEQUENCE: 225
gcacauccgu uggccauca                                                19

<210> SEQ ID NO 226
<211> LENGTH: 19
<212> TYPE: RNA
<213> ORGANISM: Homo Sapiens
<220> FEATURE:

<400> SEQUENCE: 226
gccaggcaau gaacaggaa                                                19

<210> SEQ ID NO 227
<211> LENGTH: 19
<212> TYPE: RNA
<213> ORGANISM: Homo Sapiens
<220> FEATURE:
```

```
<400> SEQUENCE: 227
ggaagccagc gcucaauug                                                    19

<210> SEQ ID NO 228
<211> LENGTH: 19
<212> TYPE: RNA
<213> ORGANISM: Homo Sapiens
<220> FEATURE:

<400> SEQUENCE: 228
gcgagccacu ggugcugaa                                                    19

<210> SEQ ID NO 229
<211> LENGTH: 19
<212> TYPE: RNA
<213> ORGANISM: Homo Sapiens
<220> FEATURE:

<400> SEQUENCE: 229
ccaccuccgu ugccauaug                                                    19

<210> SEQ ID NO 230
<211> LENGTH: 19
<212> TYPE: RNA
<213> ORGANISM: Homo Sapiens
<220> FEATURE:

<400> SEQUENCE: 230
gaaggacucu agccaguua                                                    19

<210> SEQ ID NO 231
<211> LENGTH: 19
<212> TYPE: RNA
<213> ORGANISM: Homo Sapiens
<220> FEATURE:

<400> SEQUENCE: 231
gaccacaccu ugccaucaa                                                    19

<210> SEQ ID NO 232
<211> LENGTH: 19
<212> TYPE: RNA
<213> ORGANISM: Homo Sapiens
<220> FEATURE:

<400> SEQUENCE: 232
gcaguuacca gugccaaua                                                    19

<210> SEQ ID NO 233
<211> LENGTH: 19
<212> TYPE: RNA
<213> ORGANISM: Homo Sapiens
<220> FEATURE:

<400> SEQUENCE: 233
ggacgccaau gaccuagaa                                                    19

<210> SEQ ID NO 234
<211> LENGTH: 19
<212> TYPE: RNA
<213> ORGANISM: Homo Sapiens
<220> FEATURE:

<400> SEQUENCE: 234
```

```
gaacuaugcu gccaugaag                                                    19

<210> SEQ ID NO 235
<211> LENGTH: 19
<212> TYPE: RNA
<213> ORGANISM: Homo Sapiens
<220> FEATURE:

<400> SEQUENCE: 235
caucaaagcu gccauggaa                                                    19

<210> SEQ ID NO 236
<211> LENGTH: 19
<212> TYPE: RNA
<213> ORGANISM: Homo Sapiens
<220> FEATURE:

<400> SEQUENCE: 236
agacauugcu gccacagua                                                    19

<210> SEQ ID NO 237
<211> LENGTH: 19
<212> TYPE: RNA
<213> ORGANISM: Homo Sapiens
<220> FEATURE:

<400> SEQUENCE: 237
ggccaguucu acgucauga                                                    19

<210> SEQ ID NO 238
<211> LENGTH: 19
<212> TYPE: RNA
<213> ORGANISM: Homo Sapiens
<220> FEATURE:

<400> SEQUENCE: 238
gccaggagcu gaacauuaa                                                    19

<210> SEQ ID NO 239
<211> LENGTH: 19
<212> TYPE: RNA
<213> ORGANISM: Homo Sapiens
<220> FEATURE:

<400> SEQUENCE: 239
cacguccgcu caagagugu                                                    19

<210> SEQ ID NO 240
<211> LENGTH: 19
<212> TYPE: RNA
<213> ORGANISM: Homo Sapiens
<220> FEATURE:

<400> SEQUENCE: 240
uaacaaugcu gggaauuca                                                    19

<210> SEQ ID NO 241
<211> LENGTH: 19
<212> TYPE: RNA
<213> ORGANISM: Homo Sapiens
<220> FEATURE:

<400> SEQUENCE: 241
agacagagcu ugagaauaa                                                    19
```

```
<210> SEQ ID NO 242
<211> LENGTH: 19
<212> TYPE: RNA
<213> ORGANISM: Homo Sapiens
<220> FEATURE:

<400> SEQUENCE: 242
uguugcagcu uccuacuuc                                                    19

<210> SEQ ID NO 243
<211> LENGTH: 19
<212> TYPE: RNA
<213> ORGANISM: Homo Sapiens
<220> FEATURE:

<400> SEQUENCE: 243
gaccaaggcu uacugaaua                                                    19

<210> SEQ ID NO 244
<211> LENGTH: 19
<212> TYPE: RNA
<213> ORGANISM: Homo Sapiens
<220> FEATURE:

<400> SEQUENCE: 244
cauaguuggu gaagacaua                                                    19

<210> SEQ ID NO 245
<211> LENGTH: 19
<212> TYPE: RNA
<213> ORGANISM: Homo Sapiens
<220> FEATURE:

<400> SEQUENCE: 245
gagcuccacu ucaaugaga                                                    19

<210> SEQ ID NO 246
<211> LENGTH: 19
<212> TYPE: RNA
<213> ORGANISM: Homo Sapiens
<220> FEATURE:

<400> SEQUENCE: 246
gaacagaagu uacguuguc                                                    19

<210> SEQ ID NO 247
<211> LENGTH: 19
<212> TYPE: RNA
<213> ORGANISM: Homo Sapiens
<220> FEATURE:

<400> SEQUENCE: 247
caccuggacu ccuaugaga                                                    19

<210> SEQ ID NO 248
<211> LENGTH: 19
<212> TYPE: RNA
<213> ORGANISM: Homo Sapiens
<220> FEATURE:

<400> SEQUENCE: 248
cuacaacugu ccuaaccca                                                    19

<210> SEQ ID NO 249
```

```
<211> LENGTH: 19
<212> TYPE: RNA
<213> ORGANISM: Homo Sapiens
<220> FEATURE:

<400> SEQUENCE: 249
cuacacaauu gucacauua                                            19

<210> SEQ ID NO 250
<211> LENGTH: 19
<212> TYPE: RNA
<213> ORGANISM: Homo Sapiens
<220> FEATURE:

<400> SEQUENCE: 250
ugaggaggcu gaguaauuc                                            19

<210> SEQ ID NO 251
<211> LENGTH: 19
<212> TYPE: RNA
<213> ORGANISM: Homo Sapiens
<220> FEATURE:

<400> SEQUENCE: 251
ccacagaacu caugaacau                                            19

<210> SEQ ID NO 252
<211> LENGTH: 19
<212> TYPE: RNA
<213> ORGANISM: Homo Sapiens
<220> FEATURE:

<400> SEQUENCE: 252
ucaacuucau cacugagua                                            19

<210> SEQ ID NO 253
<211> LENGTH: 19
<212> TYPE: RNA
<213> ORGANISM: Homo Sapiens
<220> FEATURE:

<400> SEQUENCE: 253
cgucagagcu ucuccguaa                                            19

<210> SEQ ID NO 254
<211> LENGTH: 19
<212> TYPE: RNA
<213> ORGANISM: Homo Sapiens
<220> FEATURE:

<400> SEQUENCE: 254
cguagccgcu gccuaugua                                            19

<210> SEQ ID NO 255
<211> LENGTH: 19
<212> TYPE: RNA
<213> ORGANISM: Homo Sapiens
<220> FEATURE:

<400> SEQUENCE: 255
acagcgacgu guucucuga                                            19

<210> SEQ ID NO 256
<211> LENGTH: 19
<212> TYPE: RNA
```

```
<213> ORGANISM: Homo Sapiens
<220> FEATURE:

<400> SEQUENCE: 256
cagaaggccu cgaaucuca                                                      19

<210> SEQ ID NO 257
<211> LENGTH: 19
<212> TYPE: RNA
<213> ORGANISM: Homo Sapiens
<220> FEATURE:

<400> SEQUENCE: 257
gcucaaggcu ggugaugug                                                      19

<210> SEQ ID NO 258
<211> LENGTH: 19
<212> TYPE: RNA
<213> ORGANISM: Homo Sapiens
<220> FEATURE:

<400> SEQUENCE: 258
gaugacauac agccuauca                                                      19

<210> SEQ ID NO 259
<211> LENGTH: 19
<212> TYPE: RNA
<213> ORGANISM: Homo Sapiens
<220> FEATURE:

<400> SEQUENCE: 259
uuuauucgau uccucguua                                                      19

<210> SEQ ID NO 260
<211> LENGTH: 19
<212> TYPE: RNA
<213> ORGANISM: Homo Sapiens
<220> FEATURE:

<400> SEQUENCE: 260 ucgagugggau gauguaaua                                                     19

<210> SEQ ID NO 261
<211> LENGTH: 19
<212> TYPE: RNA
<213> ORGANISM: Homo Sapiens
<220> FEATURE:

<400> SEQUENCE: 261
aggaucugca uagagucuu                                                      19

<210> SEQ ID NO 262
<211> LENGTH: 19
<212> TYPE: RNA
<213> ORGANISM: Homo Sapiens
<220> FEATURE:

<400> SEQUENCE: 262
caaccuggau ggugacaug                                                      19

<210> SEQ ID NO 263
<211> LENGTH: 19
<212> TYPE: RNA
<213> ORGANISM: Homo Sapiens
<220> FEATURE:
```

```
<400> SEQUENCE: 263
ugaagaacgg uaccagaug                                              19

<210> SEQ ID NO 264
<211> LENGTH: 19
<212> TYPE: RNA
<213> ORGANISM: Homo Sapiens
<220> FEATURE:

<400> SEQUENCE: 264
gugagacagu gacggauua                                              19

<210> SEQ ID NO 265
<211> LENGTH: 19
<212> TYPE: RNA
<213> ORGANISM: Homo Sapiens
<220> FEATURE:

<400> SEQUENCE: 265
acgaacaggu gaugcacua                                              19

<210> SEQ ID NO 266
<211> LENGTH: 19
<212> TYPE: RNA
<213> ORGANISM: Homo Sapiens
<220> FEATURE:

<400> SEQUENCE: 266
aauaaugaau ggacgacuu                                              19

<210> SEQ ID NO 267
<211> LENGTH: 19
<212> TYPE: RNA
<213> ORGANISM: Homo Sapiens
<220> FEATURE:

<400> SEQUENCE: 267
gaugaccugu ccauagaug                                              19

<210> SEQ ID NO 268
<211> LENGTH: 19
<212> TYPE: RNA
<213> ORGANISM: Homo Sapiens
<220> FEATURE:

<400> SEQUENCE: 268
ucuaugaccu guccaagga                                              19

<210> SEQ ID NO 269
<211> LENGTH: 19
<212> TYPE: RNA
<213> ORGANISM: Homo Sapiens
<220> FEATURE:

<400> SEQUENCE: 269
auacagaucu ggucgaguu                                              19

<210> SEQ ID NO 270
<211> LENGTH: 19
<212> TYPE: RNA
<213> ORGANISM: Homo Sapiens
<220> FEATURE:

<400> SEQUENCE: 270
```

-continued cauauugacu uccuguauu                                                19

<210> SEQ ID NO 271
<211> LENGTH: 19
<212> TYPE: RNA
<213> ORGANISM: Aequorea Victoria
<220> FEATURE:

<400> SEQUENCE: 271
gcaaagaccc caacgagaa                                                19

<210> SEQ ID NO 272
<211> LENGTH: 19
<212> TYPE: RNA
<213> ORGANISM: Homo Sapiens
<220> FEATURE:

<400> SEQUENCE: 272
gcacggaagu ccaucugaa                                                19

<210> SEQ ID NO 273
<211> LENGTH: 19
<212> TYPE: RNA
<213> ORGANISM: Homo Sapiens
<220> FEATURE:

<400> SEQUENCE: 273
gcaggacaaa gauguauua                                                19

<210> SEQ ID NO 274
<211> LENGTH: 19
<212> TYPE: RNA
<213> ORGANISM: Homo Sapiens
<220> FEATURE:

<400> SEQUENCE: 274
gggucugugg ugauaaaua                                                19

<210> SEQ ID NO 275
<211> LENGTH: 19
<212> TYPE: RNA
<213> ORGANISM: Homo Sapiens
<220> FEATURE:

<400> SEQUENCE: 275
guaugagaac ccaauguca                                                19

<210> SEQ ID NO 276
<211> LENGTH: 19
<212> TYPE: RNA
<213> ORGANISM: Homo Sapiens
<220> FEATURE:

<400> SEQUENCE: 276
gcacggaagu ccaucugaa                                                19

<210> SEQ ID NO 277
<211> LENGTH: 19
<212> TYPE: RNA
<213> ORGANISM: Homo Sapiens
<220> FEATURE:

<400> SEQUENCE: 277
gcaggacaaa gauguauua                                                19

<210> SEQ ID NO 278
<211> LENGTH: 19
<212> TYPE: RNA
<213> ORGANISM: Homo Sapiens
<220> FEATURE:

<400> SEQUENCE: 278
gggucugugg ugauaaaua                                              19

<210> SEQ ID NO 279
<211> LENGTH: 19
<212> TYPE: RNA
<213> ORGANISM: Homo Sapiens
<220> FEATURE:

<400> SEQUENCE: 279
guaugagaac ccaauguca                                              19

<210> SEQ ID NO 280
<211> LENGTH: 19
<212> TYPE: RNA
<213> ORGANISM: Homo Sapiens
<220> FEATURE:

<400> SEQUENCE: 280
auguuuacua ccaaaugga                                              19

<210> SEQ ID NO 281
<211> LENGTH: 19
<212> TYPE: RNA
<213> ORGANISM: Homo Sapiens
<220> FEATURE:

<400> SEQUENCE: 281
uaacugcagc caacuauuu                                              19

<210> SEQ ID NO 282
<211> LENGTH: 19
<212> TYPE: RNA
<213> ORGANISM: Homo Sapiens
<220> FEATURE:

<400> SEQUENCE: 282
uccaggaguu ugucaauaa                                              19

<210> SEQ ID NO 283
<211> LENGTH: 19
<212> TYPE: RNA
<213> ORGANISM: Homo Sapiens
<220> FEATURE:

<400> SEQUENCE: 283
gcagauacuu gagccauug                                              19

<210> SEQ ID NO 284
<211> LENGTH: 19
<212> TYPE: RNA
<213> ORGANISM: Homo Sapiens
<220> FEATURE:

<400> SEQUENCE: 284
ccggaaauuu gaagaguau                                              19

```
<210> SEQ ID NO 285
<211> LENGTH: 19
<212> TYPE: RNA
<213> ORGANISM: Homo Sapiens
<220> FEATURE:

<400> SEQUENCE: 285
auguuuacua ccaaaugga                                                    19

<210> SEQ ID NO 286
<211> LENGTH: 19
<212> TYPE: RNA
<213> ORGANISM: Homo Sapiens
<220> FEATURE:

<400> SEQUENCE: 286
uaacugcagc caacuauuu                                                    19

<210> SEQ ID NO 287
<211> LENGTH: 19
<212> TYPE: RNA
<213> ORGANISM: Homo Sapiens
<220> FEATURE:

<400> SEQUENCE: 287
uccaggaguu ugucaauaa                                                    19

<210> SEQ ID NO 288
<211> LENGTH: 19
<212> TYPE: RNA
<213> ORGANISM: Homo Sapiens
<220> FEATURE:

<400> SEQUENCE: 288
gcagauacuu gagccauug                                                    19

<210> SEQ ID NO 289
<211> LENGTH: 19
<212> TYPE: RNA
<213> ORGANISM: Homo Sapiens
<220> FEATURE:

<400> SEQUENCE: 289
ccggaaauuu gaagaguau                                                    19

<210> SEQ ID NO 290
<211> LENGTH: 19
<212> TYPE: RNA
<213> ORGANISM: Homo Sapiens
<220> FEATURE:

<400> SEQUENCE: 290
ggacauuugu guacucacu                                                    19

<210> SEQ ID NO 291
<211> LENGTH: 19
<212> TYPE: RNA
<213> ORGANISM: Photinus Pyralis
<220> FEATURE:

<400> SEQUENCE: 291
uguuugugga cgaaguacc                                                    19

<210> SEQ ID NO 292
<211> LENGTH: 19
```

-continued

```
<212> TYPE: RNA
<213> ORGANISM: Homo Sapiens
<220> FEATURE:

<400> SEQUENCE: 292
ccuggccaag gucauccau                                              19

<210> SEQ ID NO 293
<211> LENGTH: 19
<212> TYPE: RNA
<213> ORGANISM: Homo Sapiens
<220> FEATURE:

<400> SEQUENCE: 293
gagaaaggau uuggcuaca                                              19

<210> SEQ ID NO 294
<211> LENGTH: 19
<212> TYPE: RNA
<213> ORGANISM: Homo Sapiens
<220> FEATURE:

<400> SEQUENCE: 294
uaacugcagc caacuauuu                                              19

<210> SEQ ID NO 295
<211> LENGTH: 19
<212> TYPE: RNA
<213> ORGANISM: Homo Sapiens
<220> FEATURE:

<400> SEQUENCE: 295
uccaggaguu ugucaauaa                                              19

<210> SEQ ID NO 296
<211> LENGTH: 19
<212> TYPE: RNA
<213> ORGANISM: Homo Sapiens
<220> FEATURE:

<400> SEQUENCE: 296
gcagauacuu gagccauug                                              19

<210> SEQ ID NO 297
<211> LENGTH: 19
<212> TYPE: RNA
<213> ORGANISM: Homo Sapiens
<220> FEATURE:

<400> SEQUENCE: 297
ccggaaauuu gaagaguau                                              19

<210> SEQ ID NO 298
<211> LENGTH: 19
<212> TYPE: RNA
<213> ORGANISM: Homo Sapiens
<220> FEATURE:

<400> SEQUENCE: 298
ggacauuugu guacucacu                                              19

<210> SEQ ID NO 299
<211> LENGTH: 19
<212> TYPE: RNA
<213> ORGANISM: Homo Sapiens
```

```
<220> FEATURE:

<400> SEQUENCE: 299
caaaggugcu gcugaugua                                                    19

<210> SEQ ID NO 300
<211> LENGTH: 19
<212> TYPE: RNA
<213> ORGANISM: Homo Sapiens
<220> FEATURE:

<400> SEQUENCE: 300
caaagaagau aaccaaugu                                                    19

<210> SEQ ID NO 301
<211> LENGTH: 19
<212> TYPE: RNA
<213> ORGANISM: Homo Sapiens
<220> FEATURE:

<400> SEQUENCE: 301
gaaacauccu ccggcugaa                                                    19
```

US 7,834,171 B2

MODIFIED POLYNUCLEOTIDES FOR REDUCING OFF-TARGET EFFECTS IN RNA INTERFERENCE

CROSS-REFERENCE TO RELATED APPLICATIONS

This patent application is a continuation of U.S. patent application Ser. No. 11/019,831, filed on Dec. 22, 2004, which is a continuation-in-part of PCT Patent Application No. PCT/US2004/010343, filed on Apr. 1, 2004, and which also claims benefit of U.S. Provisional Application Ser. No. 60/630,228, filed on Nov. 22, 2004. This patent application is also a continuation-in-part of U.S. patent application Ser. No. 10/551,350, filed on May 30, 2005, which is a nationalization of PCT Patent Application PCT/US2004/010343, filed on Apr. 1, 2004, which claims benefit of U.S. Provisional Patent Application Ser. No. 60/543,640, filed Feb. 10, 2004, and which also claims benefit of both U.S. patent application Ser. No. 10/613,077, filed on Jul. 1, 2003, and U.S. patent application Ser. No. 10/406,908, filed on Apr. 2, 2003, and also claims benefit of U.S. Provisional Application Ser. Nos. 60/543,640 and 60/543,661, which were filed on Feb. 10, 2004, and claims benefit of U.S. Provisional Application Ser. Nos. 60/542,646, and 60/542,668, which were filed Feb. 6, 2004. Each of the foregoing patent applications is incorporated herein in their entirety by specific reference.

BACKGROUND OF THE INVENTION

1. The Field of the Invention

The present invention relates to the field of modified polynucleotides.

2. The Relevant Technology

Gene knockdown by RNA-induced gene silencing is presently believed to implicate a minimum of three different levels of control: (i) transcription inactivation (siRNA-guided DNA and histone methylation); (ii) small interfering RNA (siRNA)-induced mRNA degradation; and (iii) siRNA-induced transcriptional attenuation. The RNA interference (RNAi) generated by siRNA can be long lasting and effective over multiple cell divisions. Therefore, RNAi represents a potentially valuable tool that can be useful in gene function analysis, drug target validation, pathway analysis, and disease therapeutics.

Recent studies into the mechanism of RNAi-mediated transcript degradation pathway have revealed a number of key components in this pathway. A Type III RNase called Dicer processes long ds RNA into siRNA (19-23 bp duplexes) that subsequently partner with the RNA Interfering Silencing Complex (RISC) to mediate the degradation of target transcripts in a sequence specific manner. This phenomenon has been observed in a diverse group of organisms. Unfortunately, initial attempts to use long dsRNA to induce RNAi in mammalian cells met with only limited success due to induction of the interferon response, which results in a general, as opposed to targeted, inhibition of protein synthesis.

More recently, it has been shown that when short synthetic siRNAs are introduced into mammalian cells in culture, sequence-specific degradation of target mRNA can be achieved without inducing an interferon response. These short duplexes, can act catalytically at sub-molar concentrations to cleave greater than 95% of the target mRNA in a cell. A description of the mechanisms for siRNA activity, as well as some of its applications is provided in Provost et al., Ribonuclease Activity and RNA Binding of Recombinant Human Dicer, E.M.B.O.J, 2002 Nov., 1, 21(21): 5864-5874; Tabara et al., The dsRNA Binding Protein RDE-4 Interacts with RDE-1, DCR-1 and a DexH-box Helicase to Direct RNAi in C. elegans, Cell 2002, Jun. 28, 109(7):861-71; Ketting et al., Dicer Functions in RNA Interference and in Synthesis of Small RNA Involved in Developmental Timing in C. elegans, Genes and Development, 2001, 15(20):2654-9; and Martinez et al., Single-Stranded Antisense siRNAs Guide Target RNA Cleavage in RNAi, Cell 2002, Sep. 6, 110(5):563.

Despite the promise of RNAi, four main issues including functionality, specificity, delivery methods, and stability, must be addressed when working with siRNA. Specificity refers to the ability of a particular siRNA to silence a desired target without altering the expression of other genes, and recent studies have shown that "off-targeting" (i.e., the knockdown of targets other than the intended target) is much more extensive in RNAi than originally predicted (see Jackson, A. L. et al. (2003) "Expression profiling reveals off-target gene regulation by RNAi" Nature Biotechnology 21:635-7).

As off-target effects can induce undesirable phenotypes, new methods and compositions that minimize, alter, or eliminate off-target effects are considered indispensable for siRNA to become an efficacious research and therapeutic tool. The present invention addresses the issue of specificity by providing modifications to siRNA that can either increase or alter siRNA specificity.

BRIEF SUMMARY OF THE INVENTION

The present invention is directed to compositions and methods for performing RNA interference. In general the siRNA chemical modifications described herein affect a critical property of the molecules: specificity. Modifications that affect specificity are particularly advantageous in research and therapeutic applications where specificity is critical. A distinct combination of modifications (and derivatives of that modification pattern) that substantially improve RNAi applications is disclosed and is applicable in the design of optimum silencing reagents.

According to a first embodiment, the present invention is directed to a double stranded ribonucleotide comprising:

a. a sense strand, wherein said sense strand comprises i. a first 5' sense nucleotide, wherein said first 5' sense nucleotide comprises a first 2'-O-alkyl modification, and ii. a second 5' sense nucleotide, wherein said second 5' sense nucleotide comprises a second 2'-O-alkyl modification; and b. an antisense strand, wherein said antisense strand comprises i. a first 5' antisense nucleotide, wherein said first 5' antisense nucleotide is phosphorylated on the 5' carbon of the sugar moiety, and ii. a second 5' antisense nucleotide, wherein said second 5' antisense nucleotide comprises a third 2'-O-alkyl modification, wherein said sense strand and said antisense strand are capable of forming a duplex of 18-24 base pairs of nucleotides that has at least 80% complementarity over the range of the duplex, and within said duplex said first 5' sense nucleotide is the 5' most nucleotide of the sense strand, said second 5' sense nucleotide is immediately adjacent to and downstream of the first 5' sense nucleotide, said first 5' antisense nucleotide is the 5' most nucleotide of the antisense strand and said second 5' antisense nucleotide is immediately adjacent to and downstream of the first 5' antisense nucleotide.

According to a second embodiment, the present invention is directed to a unimolecular siRNA capable of forming a hairpin siRNA, said unimolecular siRNA comprising:

a. a sense strand comprising a sense region, wherein said sense region comprises i. a first 5' sense nucleotide, wherein said first 5' sense nucleotide comprises a first 2'-O-alkyl modification, and ii. a second 5' sense nucleotide, wherein said second 5' sense nucleotide comprises a second 2'-O-alkyl modification; and b. an antisense strand comprising an antisense region, wherein said antisense region comprises i. a first 5' antisense nucleotide, wherein said first 5' antisense nucleotide is phosphorylated on the 5' carbon, and ii. a second 5' antisense nucleotide, wherein said second 5' antisense nucleotide comprises a third 2'-O-alkyl modification, c. a loop region, wherein said loop region is located between said sense region and said antisense region.

wherein said sense strand and said antisense strand are capable of forming a duplex of 18-24 base pairs of nucleotides that has at least 80% complementarity over the range of the duplex, and within said duplex said first 5' sense nucleotide is the 5' most nucleotide of the duplex region, said second 5' sense nucleotide is immediately adjacent to and downstream of the first 5' sense nucleotide, said first 5' antisense nucleotide is the 5' most nucleotide of the antisense strand of the duplex region and said second 5' antisense nucleotide is immediately adjacent to and downstream of the first 5' antisense nucleotide.

According to a third embodiment, the present invention is directed to a method for minimizing off-target effects, said method comprising exposing an siRNA to a target nucleic acid or to a cell that is expressing or is capable of expressing said target nucleic acid, wherein said siRNA comprises:

a. a sense strand, wherein said sense strand comprises i. a first 5' sense nucleotide, wherein said first 5' sense nucleotide comprises a first 2'-O-alkyl modification, and ii. a second 5' sense nucleotide, wherein said second 5' sense nucleotide comprises a second 2'-O-alkyl modification; and b. an antisense strand, wherein said antisense strand comprises i. a first 5' antisense nucleotide, wherein said first 5' antisense nucleotide is phosphorylated, and ii. a second 5' antisense nucleotide, wherein said second 5' antisense nucleotide comprises a third 2'-O-alkyl modification, wherein said sense strand and said antisense strand are capable of forming a duplex of 18-24 base pairs of nucleotides that has at least 80% complementarity over the range of the duplex, and within said duplex said first 5' sense nucleotide is the 5' most nucleotide of the sense strand, said second 5' sense nucleotide is immediately adjacent to and downstream of the first 5' sense nucleotide, said first 5' antisense nucleotide is the 5' most nucleotide of the antisense strand and said second 5' antisense nucleotide is immediately adjacent to and downstream of the first 5' antisense nucleotide.

According to a fourth embodiment, the present invention is directed to a method for minimizing off-target effects, said method comprising exposing a unimolecular siRNA (that is capable of forming a hairpin) to a target nucleic acid or to a cell that is expressing or is capable of expressing said target nucleic acid, wherein said unimolecular siRNA comprises:

a. a sense strand comprising a sense region, wherein said sense region comprises i. a first 5' sense nucleotide, wherein said first 5' sense nucleotide comprises a first 2'-O-alkyl modification, and ii. a second 5' sense nucleotide, wherein said second 5' sense nucleotide comprises a second 2'-O-alkyl modification; and b. an antisense strand comprising an antisense region, wherein said antisense region comprises i. a first 5' antisense nucleotide, wherein said first 5' antisense nucleotide is phosphorylated, and ii. a second 5' antisense nucleotide, wherein said second 5' antisense nucleotide comprises a third 2'-O-alkyl modification, and c. a loop region, wherein said loop region is located between said sense region and said antisense region, wherein said sense strand and said antisense strand are capable of forming a duplex of 18-24 base pairs of nucleotides that has at least 80% complementarity over the range of the duplex, and within said duplex said first 5' sense nucleotide is the 5' most nucleotide of the sense strand of the duplex region, and said second 5' sense nucleotide is immediately adjacent to and downstream of the first 5' sense nucleotide, said first 5' antisense nucleotide is the 5' most nucleotide of the antisense strand of the duplex region and said second 5' antisense nucleotide is immediately adjacent to and downstream of the first 5' antisense nucleotide.

For a better understanding of the present invention together with other and further advantages and embodiments, reference is made to the following description taken in conjunction with the examples, the scope of the which is set forth in the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

D: unmodified

Figure 1:
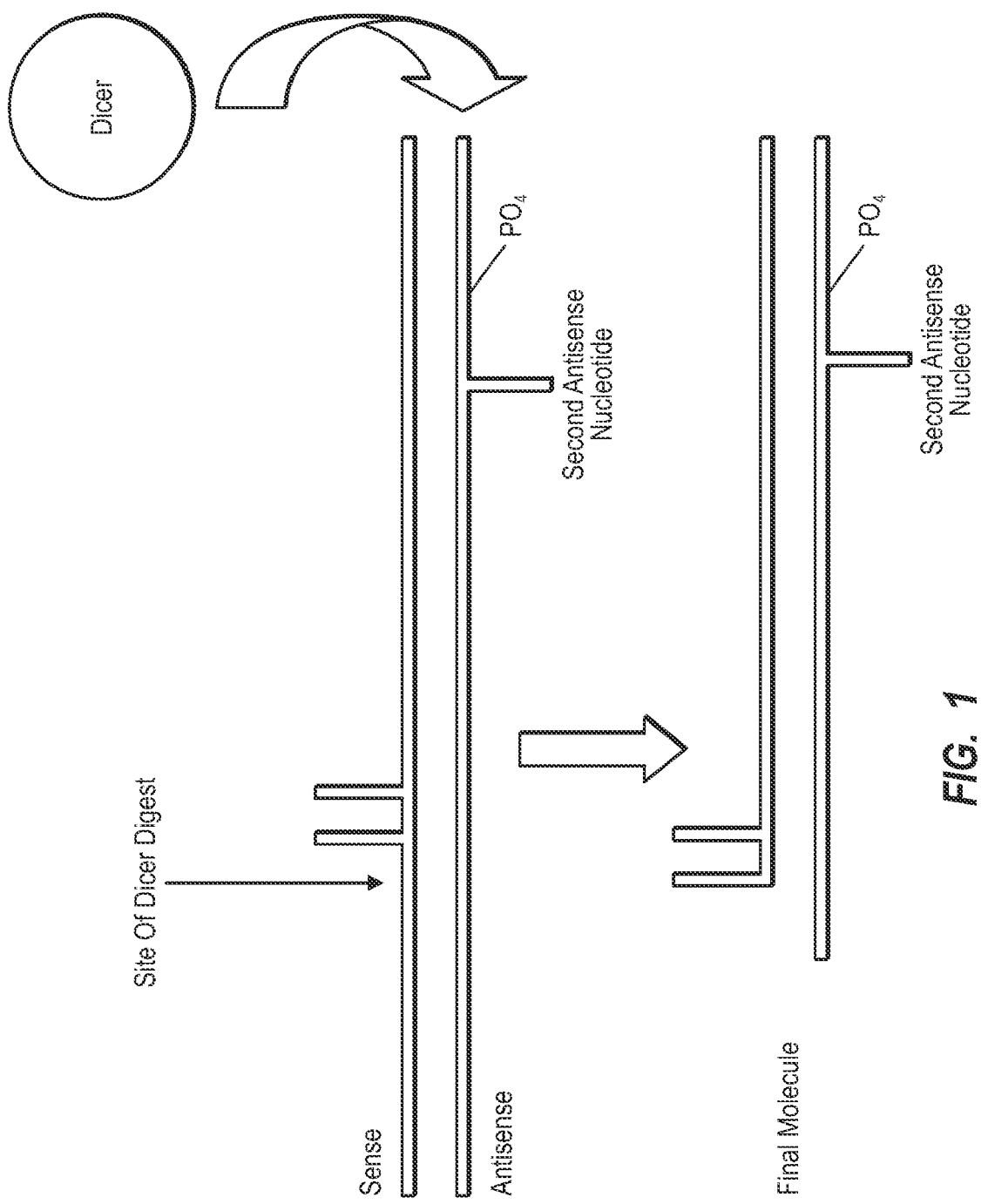
FIG. 1 depicts the relationship between positioning of one embodiment of the invention's modifications in duplexes that are longer than 25 bp. Optimal design for the molecules ensures that following Dicer digestion, the final functional duplex contains the depicted invention's modification pattern. Note, in the initial Dicer substrate, the sense and/or antisense strand can have 3' overhangs. Alternatively, both termini can be blunt ended.

E 2'O-methyl modification of positions 1 and 2 of the AS strand;

F: 2'O-methyl modification of positions 1 and 2 of the AS strand without modification of the sense strand;

G: 2'O-methyl modification of positions 2 and 3 of the AS strand;

H: 2'O-methyl modification of positions 3 and 4 of the AS strand;

I: 2'O-methyl modification of positions 4 and 5 of the AS strand;

J: 2'O-methyl modification of positions 5 and 6 of the AS strand;

K: 2'O-methyl modification of positions 6 and 7 of the AS strand;

L: 2'O-methyl modification of positions 7 and 8 of the AS strand;

M: 2'O-methyl modification of positions 8 and 9 of the AS strand;

N: 2'O-methyl modification of positions 9 and 10 of the AS strand;

O: 2'O-methyl modification of positions 10 and 11 of the AS strand;

P: 2'O-methyl modification of position 1 of the AS strand;

Q: 2'O-methyl modification of position 2 of the AS strand; and

R: 2'O-methyl modification of positions 1, 2, 11, and 12 of the AS strand

Figure 10A:
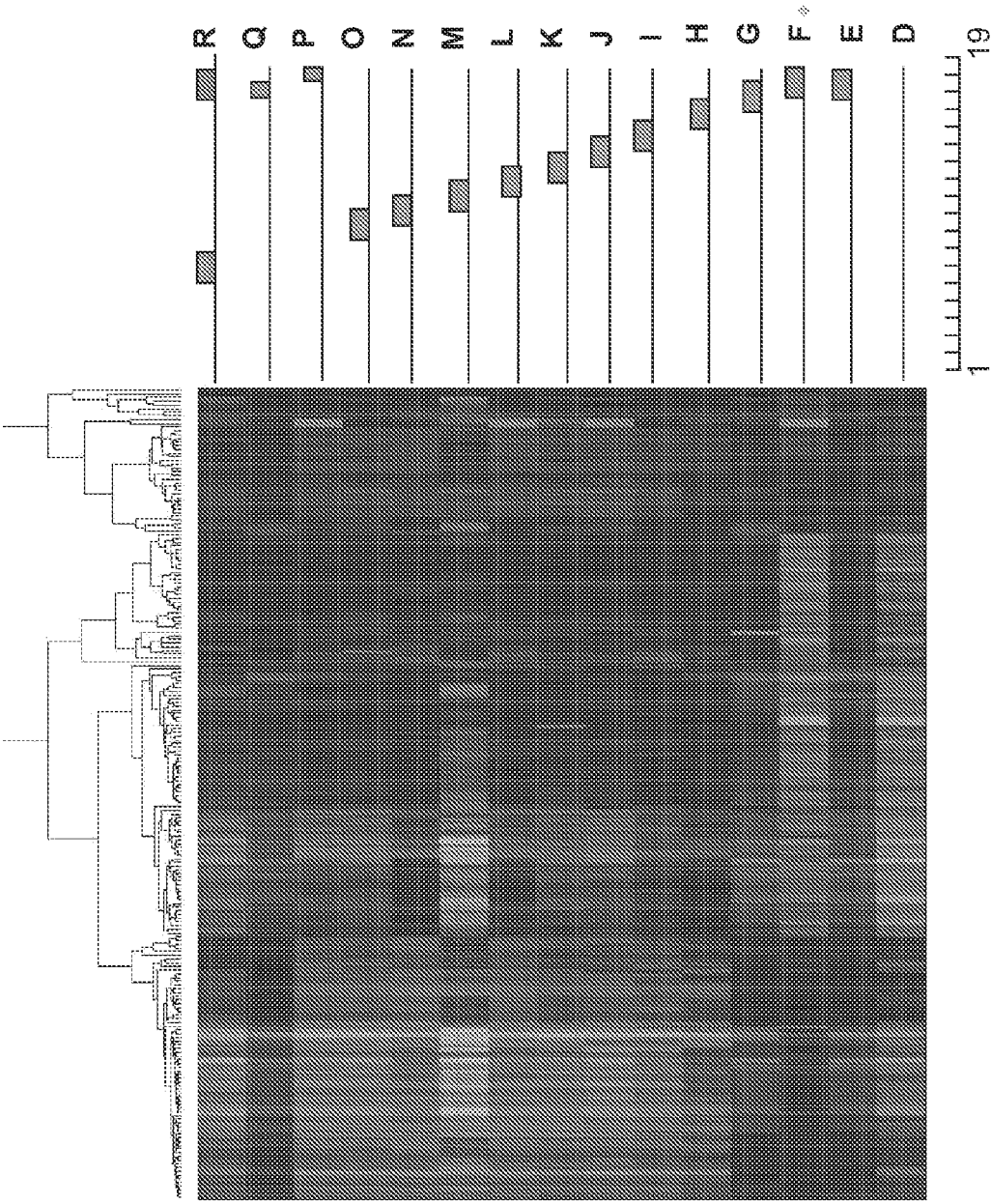
FIG. 10A depicts a heatmap showing the results of a chemical modification walk across the MAPK14-153 siRNA. Duplexes carry single modifications or paired 2'-O-methyl modifications of various positions of the siRNA antisense strand in combination with 2'-O-methyl modifications on positions 1 and 2 of the sense strand and a phosphate group on the 5' carbon of the ribose ring of the first antisense (terminal) nucleotide. Mapk14-153: 5' GUCAUCAGCUUUGUGC-CAC-3' (SEQ. ID NO. 13), sense strand. The letters D-R describe the following molecules.
Figure 10B:
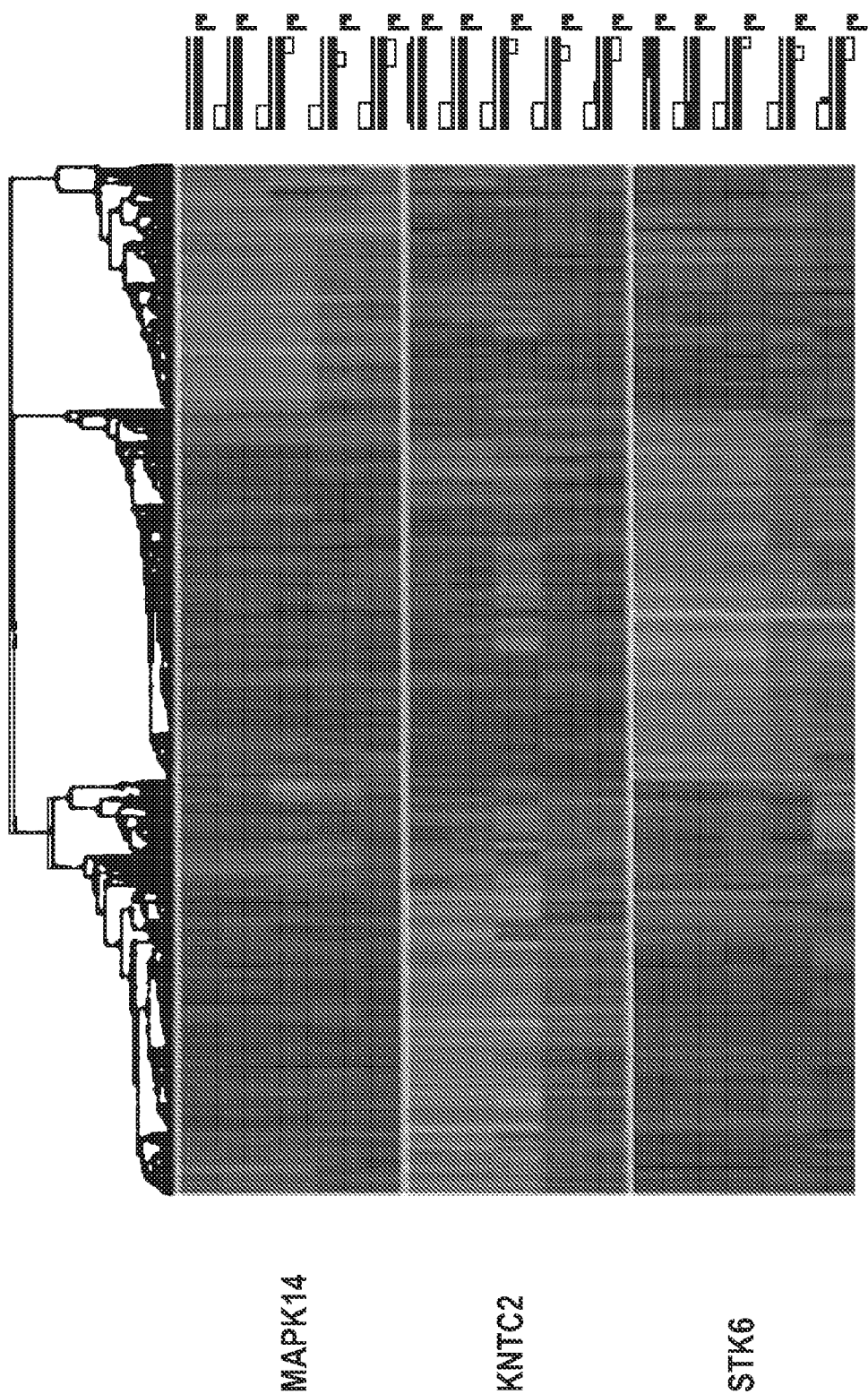

FIG. 10B depicts a heatmap demonstrating how position 2 is a critical nucleotide in determining off-target gene modulation. A) siRNA targeting three different genes (MAPK14, KNTC2, and STK6) were examined for off-target effects by microarray analysis when the duplex was unmodified (top of each set of heat maps), modified with 2'-O-methyl groups on positions 1 and 2 of the sense strand (second from top in each set of heat maps), modified with 2'-O-methyl groups on positions 1 and 2 of the sense strand plus 2'-O-methyl modifications on position 1 of the antisense strand (third from top of each set of heatmaps), modified with 2'-O-methyl groups on positions 1 and 2 of the sense strand plus 2'-O-methyl modifications on position 2 of the antisense strand (fourth from top of each set of heatmaps), and modified with 2'-O-methyl groups on positions 1 and 2 of the sense strand plus 2'-O-methyl modifications on positions 1 and 2 of the antisense strand (fifth from top of each set of heatmaps). All duplexes in this study contained a phosphate group on the 5' carbon of the ribose ring of the first antisense (terminal) nucleotide. Sense strand sequences used in this figure include:

```
KNTC2:     5' GGCUUCCUUACAAGGAGAU-3',  (SEQ. ID NO. 14)

Mapk14-    5' CCUACAGAGAACUGCGGUU-3',  (SEQ. ID NO. 15)
193:

STK6:      CGGGUCUUGUGUCCTUCAA-3'.     (SEQ. ID NO. 16)
```

Figure 11:
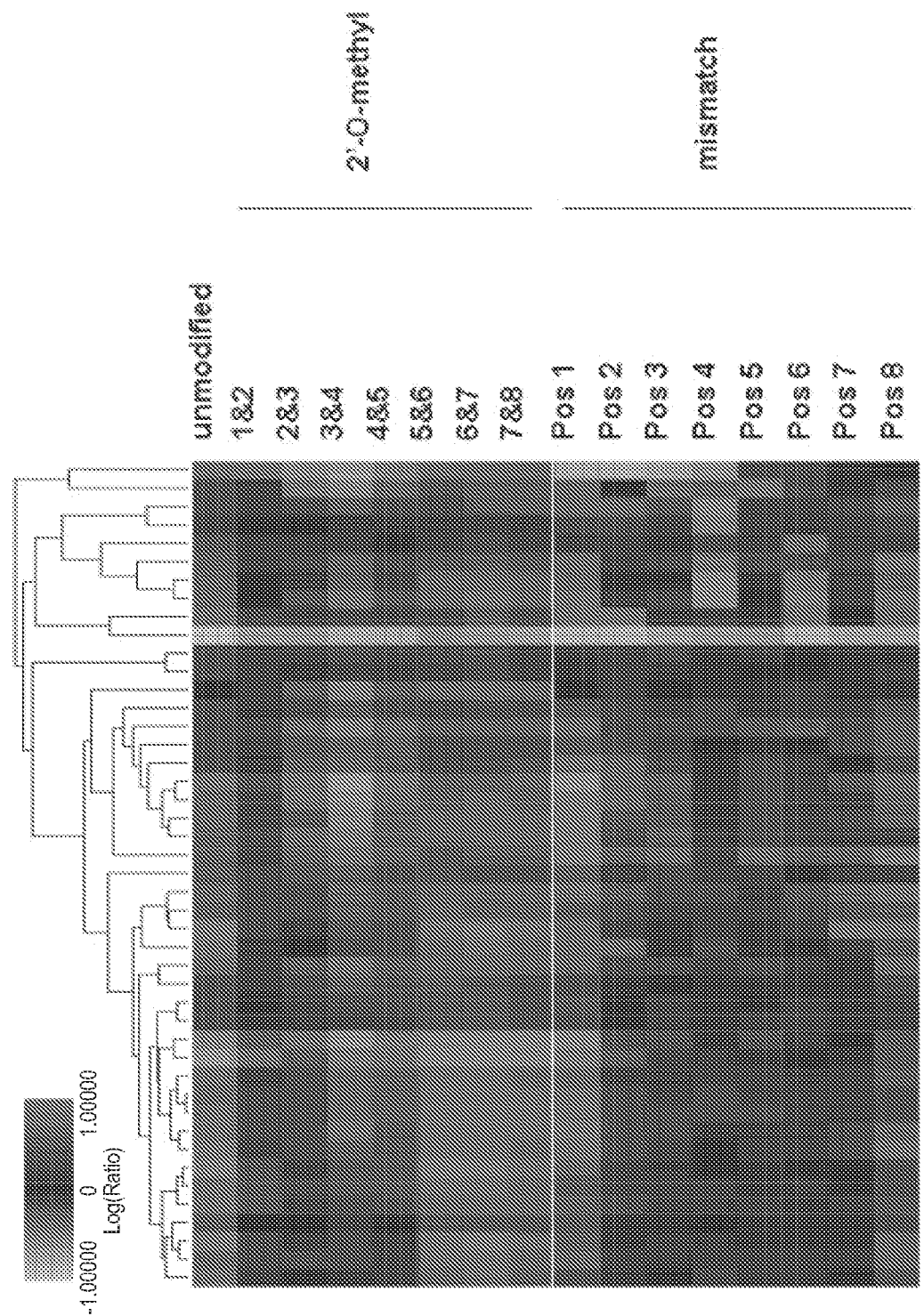

FIG. 11 compares the effects of chemical modification with selective basepair mismatches on siRNA (MAPK14-153) induced off-target effects (Mapk14-153: 5' GUCAU-CAGCUUUGUGCCAC-3' (SEQ. ID NO. 17), sense) The top eight heat maps represent duplexes that are: unmodified (top), or contain 2'-O-methyl modifications at positions 1 and 2, 2 and 3, 3 and 4, 4 and 5, 5 and 6, 6 and 7, or 7 and 8 of the antisense strand. All of the duplexes contain a phosphate group on the 5' carbon of the ribose ring of the first antisense (terminal) nucleotide. The lower half of the heatmap represents siRNA that have basepair mismatches (between the antisense strand of the siRNA and the target molecule) incorporated into the siRNA duplexes. All of the duplexes contain-a phosphate group on the 5' carbon of the ribose ring of the first antisense (terminal) nucleotide.

FIGS. 12A-D demonstrate target independent, sequence specific siRNA toxicity. 12a: HeLa cells were transfected with one of 90 different siRNA targeting DBI (NM$_{13}$ 020548, position 202-291). Data are displayed according to siRNA position in walk. Dotted (horizontal) line represents the 75% viability threshold. Boxed areas indicate toxic siRNA with sequence similarity. Toxicity data (gray bars) are superimposed on DBI mRNA expression data (black bars) for the same siRNA set. 12b: HeLa cells were transfected with one of 48 functional (>70% silencing) siRNA targeting 12 different genes. Data is sorted based on the level of siRNA-induced toxicity. Non-toxic siRNA (gray bars), toxic siRNA (black bars). 12c: HeLa cells transfected with a subset of the toxic and non-toxic siRNA from (b) targeting either MAPK1 (MEK1) or MAPK2 (MEK2). Toxicity data (gray bars) are presented alongside mRNA expression data (black bars). Data show that there is no correlation between the level of silencing and toxicity. 12d: Dilution studies showing the effects of toxic siRNA (MAP2K2-3, SRD5A1-1, SRD5A1-3 and SRD5A2-3) in HeLa cells at varying concentrations. Values for toxicity represent the average of three independent experiments (each performed in triplicate). Error bars depict standard deviation from the mean. For experimental protocols: 72 h hours after transfection, 25 microliters of Alamar Blue dye were added to wells containing cells in 100 microliters of media. Cells were then incubated (0.5 hrs) at 37 degree C. in a humidified atmosphere with 5% CO$_2$. The fluorescence was subsequently measured on a Perkin Elmer WallacVector2 1420 multi-label counter with excitation at 540 nm and emission at 590 nm. The results presented in FIG. 12 are an average of nine data points coming from three independent experiments performed on different days. For the purpose of this study, siRNAs were defined as toxic when the results from nine different experiments (taking into account standard deviations) showed cell viability was below 75%. For comparative gene expression levels, mRNA was quantitated using Quantigene® Kits (Genospectra, Fremont, Calif.) for branched DNA (bDNA) assay according to manufacturer instructions. Level of mRNA of GAPDH (a housekeeping gene) was used as a reference.

Figure 13A:
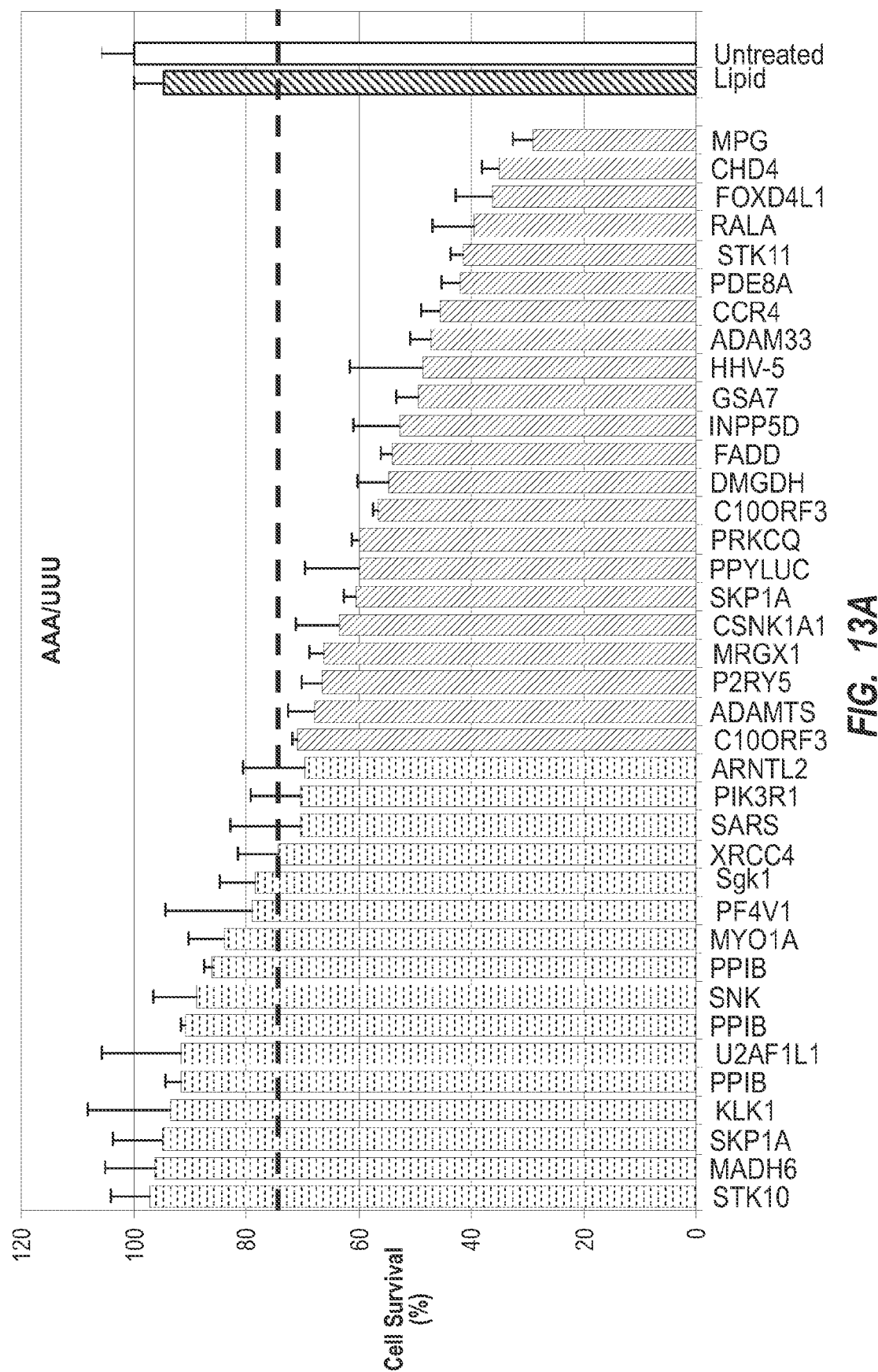
Figure 13B:
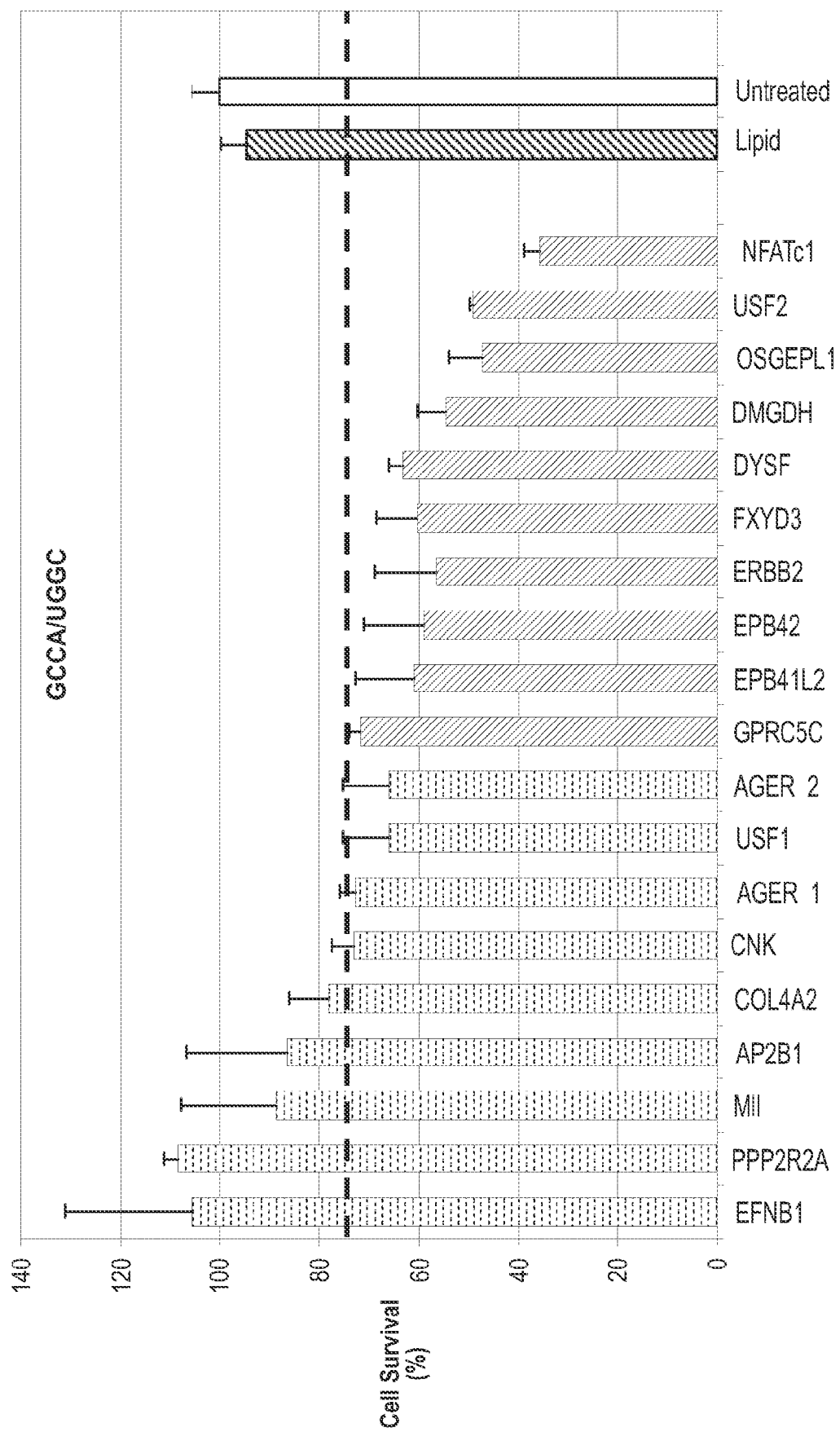
Figure 13C:
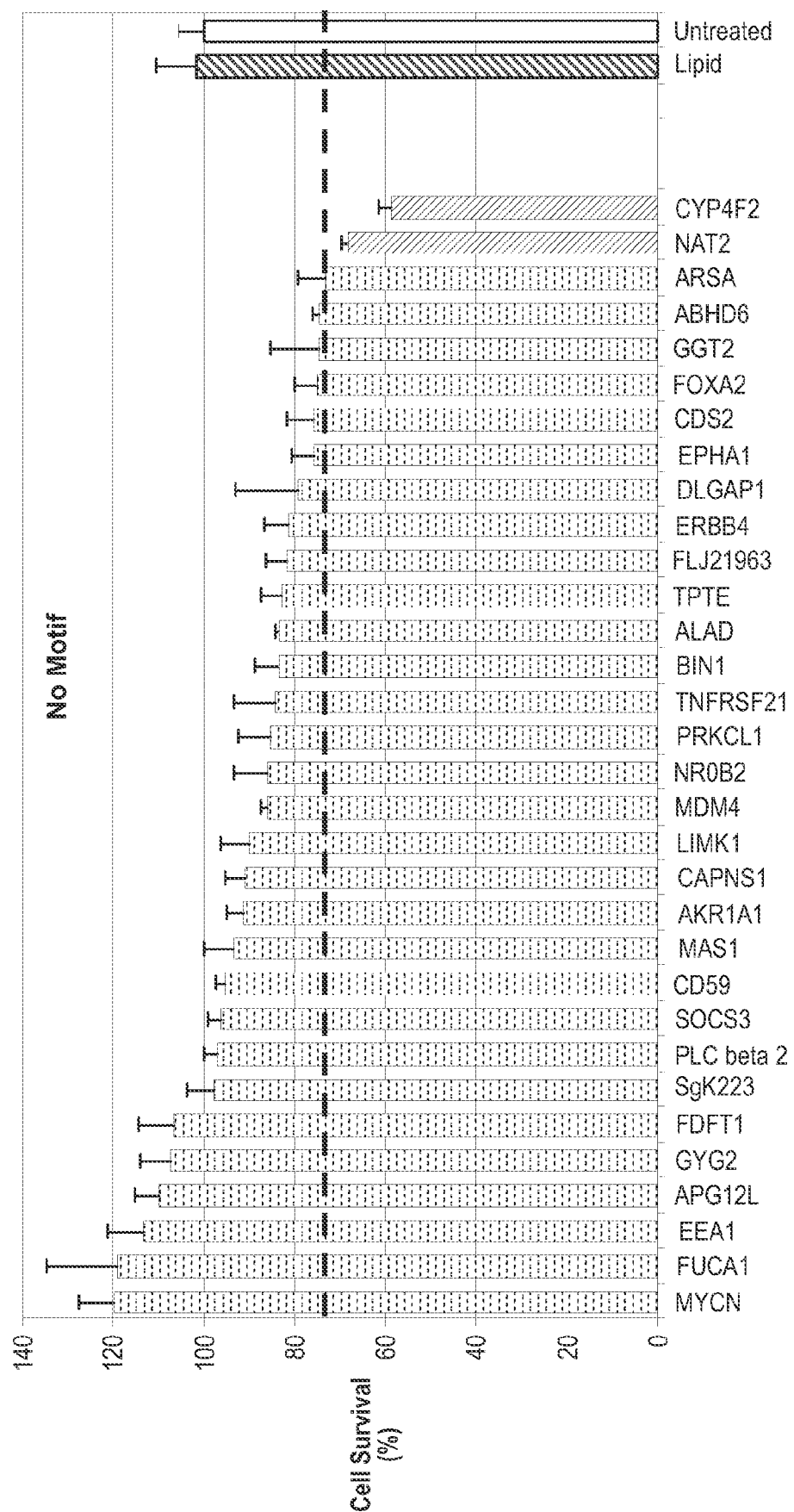

FIGS. 13A-C. Sequence dependence of siRNA toxicity. HeLa cells were transfected with functional siRNA containing 13a: AAA/UUU, 13b: GCCA/UGGC, or 13c: no toxic motifs. Motif-containing siRNA exhibit heightened incidence of toxicity. Values for toxicity represent the mean of three independent experiments (each performed in triplicate). Error bars depict standard deviation from the mean.

FIGS. 14A-L illustrate siRNA-induced toxicity mediated through the RNAi pathway. 14a: Diagram of experimental procedures used in eIF2C2/Ago2 knockdown experiments. "T1" and "T2" represent "transfection 1" and "transfection 2", respectively. Control and test siRNA were transfected in at 10 nM in each transfection, 14b-14i: Control experiments demonstrating that knockdown of the eIF2C2 gene product disables the RNAi pathway (b, d, f, and h—depicts EGFP expression levels; c, e, g, and i—show comparative Hoechst 33342 staining). Study shows that if one disables the RNAi pathway with eIF2C2 siRNA, then subsequent addition of targeting siRNA fail silence their target. 14j: Graph showing the effects of eIF2C2 knockdown on siRNA toxicity; 14k: Graph showing the effect of truncating toxic siRNA by 2 nucleotides (19 mer->17 mer) on siRNA toxicity. 14l: Graph showing the effects that chemical modifications of toxic siRNA have on siRNA toxicity. Values for toxicity represent the average of three independent experiments (each performed in triplicate). Error bars depict standard deviation from the mean. Regular and fluorescent microscopy was used to obtain data on cellular and nuclei morphology. Live cells were stained with cell-permeable nuclear fluorescent dye Hoechst 33342 (2 microg/ml, 15 minutes at 37 degree C., Molecular Probes). Pictures were taken using Leica DML fluorescent microscope InSight CCD camera and SPOT 3.5 software.

Figure 15:
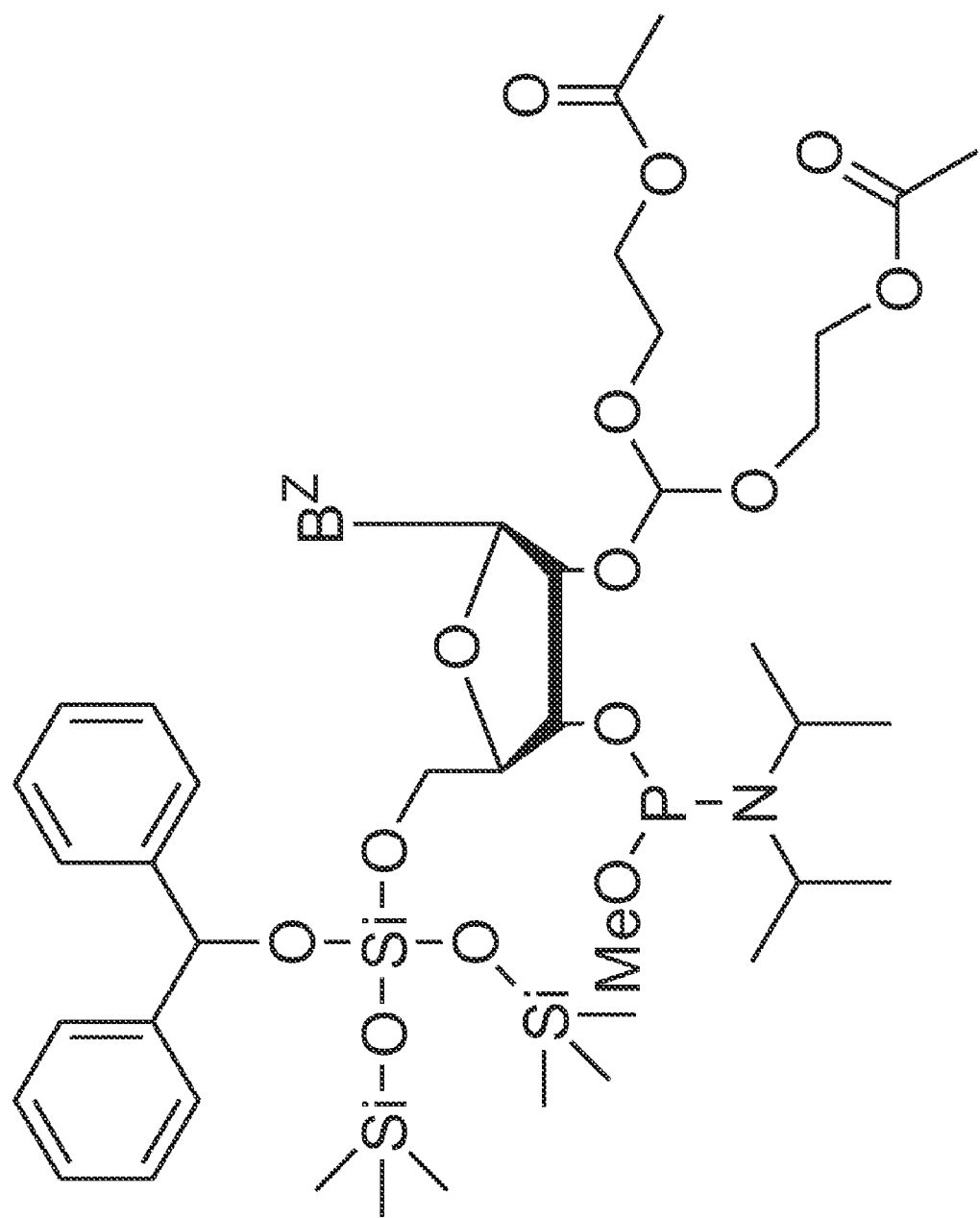

FIG. 15 illustrates a 5'-O-benzhydroxy-bis(trimethylsilyloxy)silyl-2'-O-bis(2-acetoxyethyl)orthoformyl-3'-O—(N, N-diisopropyl)methyl phosphoramidite. B is a nucleoside base such as, for example, adenosine, guanosine, cytidine, or uracil; Z is a protecting group for the exocyclic amine (isobutyryl for A and G. acetyl for C.

Figure 16:
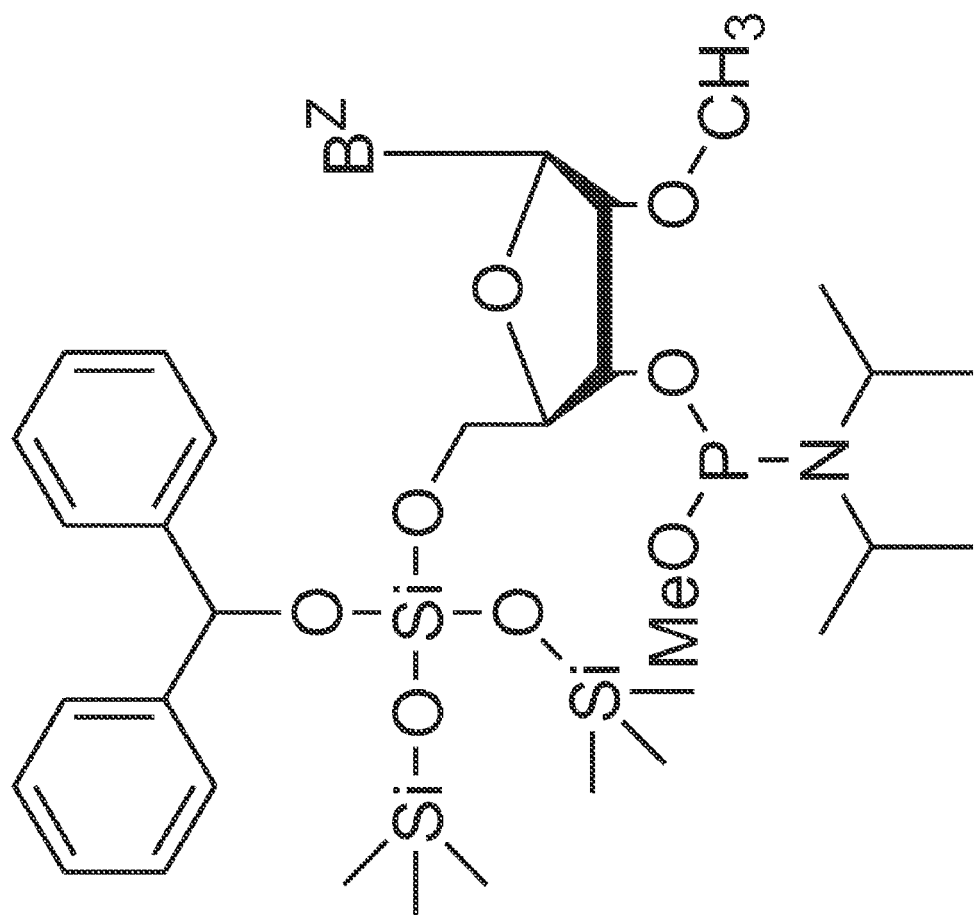

FIG. 16 illustrates a 5'-O-benzhydroxy-bis(trimethylsilyloxy)-silyl-1-2'-O-methyl-3'-O—(N,N-diisopropyl)methyl phosphoramidite. B is a nucleoside base such as, for example, adenosine, guanosine, cytidine, or uracil; Z is a protecting group for the exocyclic amine (isobutyryl for A and G. acetyl for C).

Figure 17:
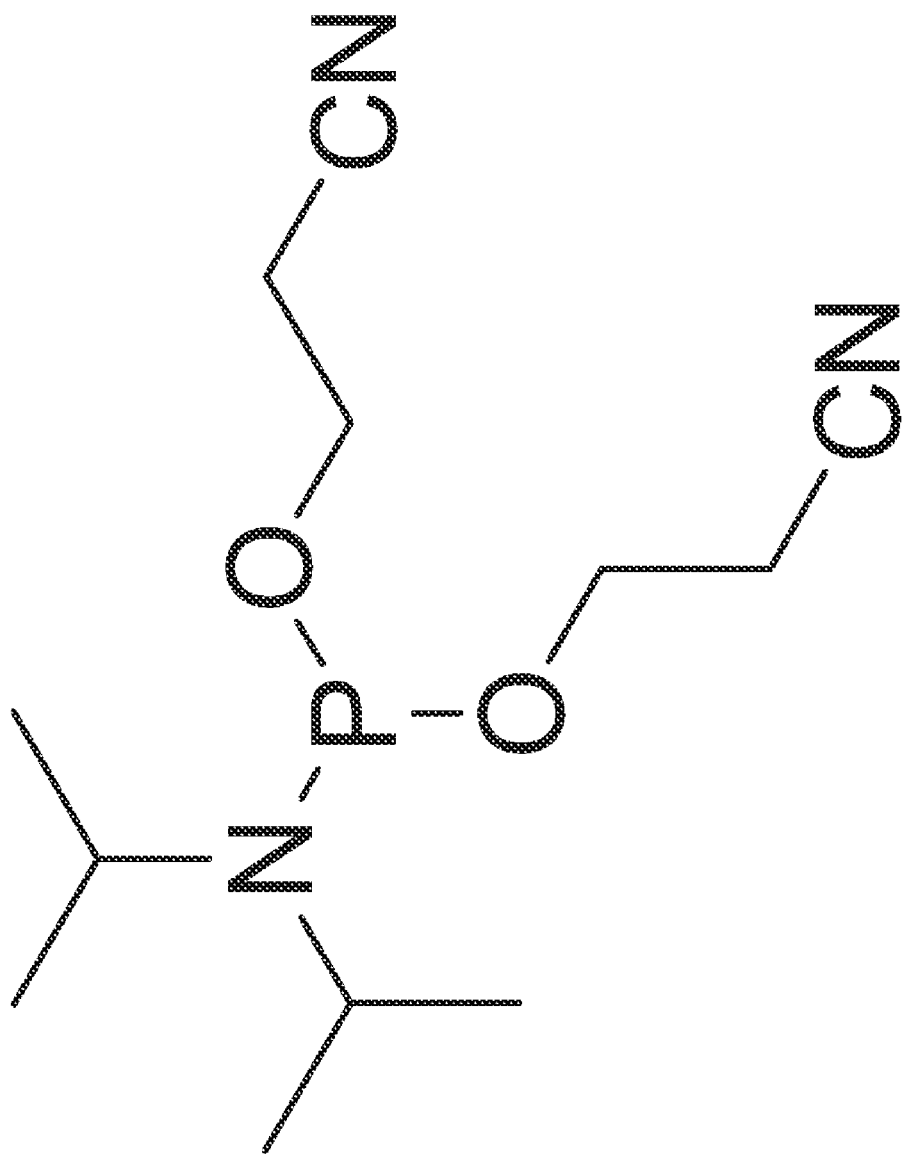

FIG. 17 illustrates an N,N-diisopropylamino-bis(2-cyanoethyl) phosphoramidite.

DETAILED DESCRIPTION OF THE PREFERRED EMBODIMENTS

The present invention will now be described in connection with preferred embodiments. These embodiments are presented to aid in an understanding of the present invention and are not intended, and should not be construed, to limit the invention in any way. All alternatives, modifications and equivalents that may become apparent to those of ordinary skill upon reading this disclosure are included within the spirit and scope of the present invention.

This disclosure is not a primer on compositions and methods for performing RNA interference. Basic concepts known to those skilled in the art have not been set forth in detail.

The present invention is directed to compositions and methods for performing RNA interference, including siRNA-induced gene silencing. Through the use of the present invention, modified polynucleotides, and derivatives thereof, one may improve the efficiency of RNA interference applications.

Unless explicitly stated otherwise, or implicit from content, the following terms and phrases include the meanings provided below:

Alkyl

The term "alkyl" refers to a hydrocarbyl moiety that can be saturated or unsaturated. It may comprise moieties that are linear, branched and/or cyclic.

Exemplary alkyl groups include but are not limited to moieties such as, for example, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl and alkyl groups of higher number of carbons, as well as 2-methylpropyl, 2-methyl-4-ethylbutyl, 2,4-diethylpropyl, 3-propylbutyl, 2,8-dibutyldecyl, 6,6-dimethyloctyl, 6-propyl-6-butyloctyl, 2-methylbutyl, 2-methylpentyl, 3-methylpentyl, 2-ethylhexyl, isopropyl, isobutyl, isopentyl, etc. The term alkyl also encompasses alkenyl groups, such as vinyl, allyl, aralkyl and alkynyl groups. Unless otherwise specified, alkyl groups are not substituted.

The preferred alkyl group for a 2' modification is a methyl group with an O-linkage to the 2' carbon of a ribosyl moiety, i.e., a 2'-O-alkyl that comprises a 2'-O-methyl group. A preferred 2'-O-methyl group is unsubstituted: —O—$CH_3$.

2'-O-Alkyl Modified Nucleotide

The phrase "2'—O-alkyl modified nucleotide" refers to a nucleotide unit having a sugar moiety, for example a deoxyribosyl moiety that is modified at the 2' position such that an oxygen atom is attached both to the carbon atom located at the 2' position of the sugar and to an alkyl group. In various embodiments, the alkyl moiety consists essentially of carbons and hydrogens. A particularly preferred embodiment is one wherein the alkyl moiety is a methyl moiety.

Antisense Strand

The phrase "antisense strand" as used herein, refers to a polynucleotide or region of a polynucleotide that is substantially (i.e., 80% or more) or 100% complementary to a target nucleic acid of interest. An antisense strand may be comprised of a polynucleotide region that is RNA, DNA or chimeric RNA/DNA. For example, an antisense strand may be complementary, in whole or in part, to a molecule of messenger RNA, an RNA sequence that is not mRNA (e.g., tRNA, rRNA and hnRNA) or a sequence of DNA that is either coding or non-coding. The phrase "antisense strand" includes the antisense region of polynucleotides that are formed from two separate strands, as well as unimolecular siRNAs that are capable of forming hairpin structures. The phrases "antisense strand" and "antisense region" are intended to be equivalent and are used interchangeably. The antisense strand can be modified with a diverse group of small molecules and/or conjugates.

2'Carbon Modification

The phrase "2' carbon modification" refers to a nucleotide unit having a sugar moiety, for example a moiety that is modified at the 2' position of the sugar subunit. A "2'—O-alkyl modified nucleotide" is modified at this position such that an oxygen atom is attached both to the carbon atom located at the 2' position of the sugar and to an alkyl group, e.g., 2'-O-methyl, 2'-O-ethyl, 2'-O-propyl, 2'-O-isopropyl, 2'-O-butyl, 2-O-isobutyl, 2'-O-ethyl-O-methyl (—$OCH_2CH_2OCH_3$), and 2'-O-ethyl-OH (—$OCH_2CH_2OH$). A "2' carbon sense modification" refers to a modification at the 2' carbon position of a nucleotide on the sense strand or within a sense region of polynucleotide. A "2' carbon antisense modification" refers to a modification at the 2'-carbon position of a nucleotide on the antisense strand or within an antisense region of polynucleotide.

Complementary

The term "complementary" refers to the ability of polynucleotides to form base pairs with one another. Base pairs are typically formed by hydrogen bonds between nucleotide units in antiparallel polynucleotide strands or regions. Complementary polynucleotide strands or regions can base pair in the Watson-Crick manner (e.g., A to T, A to U, C to G), or in any other manner that allows for the formation of stable duplexes. Complementarity is typically measured with respect to a duplex region and thus excludes, for example, overhangs. A duplex region comprises a region of complementarity between two strands or between two regions of a single strand, for example, a unimolecular siRNA. Typically, the region of complementarity results from Watson-Crick base pairing.

Perfect complementarity or 100% complementarity refers to the situation in which each nucleotide unit of one polynucleotide strand or region can hydrogen bond with each nucleotide unit of a second polynucleotide strand or region. Less than perfect complementarity refers to the situation in which some, but not all, nucleotide units of two strands or two regions can hydrogen bond with each other. For example, for two 20-mers, if only two base pairs on each strand can hydrogen bond with each other, the polynucleotide strands or regions exhibit 10% complementarity. In the same example, if 18 base pairs on each strand or each region can hydrogen bond with each other, the polynucleotide strands exhibit 90% complementarity. Substantial complementarity refers to polynucleotide strands or regions exhibiting 80% or greater complementarity.

Deoxynucleotide

The term "deoxynucleotide" refers to a nucleotide or polynucleotide lacking an OH group at the 2' or 3' position of a sugar moiety, and/or a 2',3' terminal dideoxy, but instead having a hydrogen at the 2' and/or 3' carbon.

Deoxyribonucleotide

The terms "deoxyribonucleotide" and "DNA" refer to a nucleotide or polynucleotide comprising at least one ribosyl moiety that has an H at the 2' position of a ribosyl moiety. Preferably a deoxyribonucleotide is a nucleotide having an H at its 2' position.

Downstream

A first region or nucleotide of a strand of nucleotides is considered to be downstream of a second region, if the 5' most portion of the first region is the closest portion of that region to the 3' end of the second region (or nucleotide).

First 5' Terminal Antisense Nucleotide

The phrase "first 5' terminal antisense nucleotide" refers to the nucleotide of the antisense strand or region that is located at the 5' most position of that strand with respect to the bases of the antisense strand or region that have corresponding complementary bases on the sense strand or region. Thus, in an siRNA that is made of two separate strands (i.e., not a unimolecular or hairpin siRNA), it refers to the 5' most base other than bases that are part of any 5' overhang on the antisense strand, which may or may not be present. When the first 5' terminal antisense nucleotide is part of a hairpin molecule, the term "terminal" refers to the 5' most relative position within the antisense region and thus is the 5' most nucleotide of the antisense region.

First 5' Terminal Sense Nucleotide

The phrase "first 5' terminal sense nucleotide" is defined in reference to the antisense nucleotide. In molecules that are comprised of two separate strands (i.e., not a unimolecular or hairpin siRNA), it refers to the nucleotide of the sense strand that is located at the 5' most position of that strand with respect to the bases of the sense strand that have corresponding complementary bases on the antisense strand. Thus, in an siRNA that is made of two separate strands (i.e., not a unimolecular or hairpin siRNA), it is the 5' most base other than bases that are part of any 5' overhang on the sense strand or region, which may or may not be present. When the first 5' terminal sense nucleotide is part of a unimolecular siRNA that is capable of forming a hairpin molecule, the term "terminal" refers to the relative position within the sense strand or region as measured by the distance from the base complementary to the first 5' terminal antisense nucleotide.

Functional siRNA may be divided into five (5) groups (non-functional, semi-functional, functional, highly functional, and hyper-functional) based on the level or degree of silencing that they induce in cultured cell lines. As used herein, these definitions are based on a set of conditions where the siRNA is transfected into said cell line at a concentration of 100 nM and the level of silencing is tested at a time of roughly 24 hours after transfection, and not exceeding 72 hours after transfection. In this context, "non-functional siRNA" are defined as those siRNA that induce less than 50% (<50%) target silencing. "Semi-functional siRNA" induce 50-79% target silencing. "Functional siRNA" are molecules that induce 80-95% gene silencing. "Highly-functional siRNA" are molecules that induce greater than 95% gene silencing. "Hyperfunctional siRNA" are a special class of molecules. For purposes of this document, hyperfunctional siRNA are defined as those molecules that: (1) induce greater than 95% silencing of a specific target when they are transfected at subnanomolar concentrations (i.e., less than one nanomolar); and/or (2) induce functional (or better) levels of silencing for greater than 96 hours. These relative functionalities (though not intended to be absolutes) may be used to compare siRNAs to a particular target for applications such as functional genomics, target identification and therapeutics.

Functional Dose

A "functional dose" refers to a dose of siRNA that will be effective at causing a greater than or equal to 95% reduction in mRNA at levels of 100 nM at 24, 48, 72, and 96 hours following administration, while a "marginally functional dose" of siRNA will be effective at causing a greater than or equal to 50% reduction of mRNA at 100 nM at 24 hours following administration and a "non-functional dose" of RNA will cause a less than 50% reduction in mRNA levels at 100 nM at 24 hours following administration.

Mismatch

The term "mismatch" includes a situation in which Watson-Crick base pairing does not take place between a nucleotide of a sense strand and a nucleotide of an antisense strand, where the nucleotides are flanked by a duplex comprising base pairs in the 5' direction of the mismatch beginning directly after (in the 5' direction) the mismatched position and in the 3' direction of the mismatch beginning directly after (in the 3' direction) the mismatched position. An example of a mismatch would be an A across from a G. a C across from an A, a U across from a C, an A across from an A, a G across from a G. a C across from a C, and so on. Mismatches are also meant to include an abasic residue across from a nucleotide or modified nucleotide, an acyclic residue across from a nucleotide or modified nucleotide, a gap, or an unpaired loop. In its broadest sense, a mismatch as used herein includes any alteration at a given position that decreases the thermodynamic stability at or in the vicinity of the position where the alteration appears, such that the thermodynamic stability of the duplex at the particular position is less than the thermodynamic stability of a Watson-Crick base pair at that position. Preferred mismatches include a G across from an A, and an A across from a C. A particularly preferred mismatch comprises an A across from an A, G across from a G. C across from a C, and U across from a U.

Nucleotide

The term "nucleotide" refers to a ribonucleotide or a deoxyribonucleotide or modified form thereof, as well as an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs. Preferably, a "nucleotide" comprises a cytosine, uracil, thymine, adenine, or guanine moiety. Preferred nucleotides, unless otherwise specified (such as, for example, when specifying a 2' modification, 5' modification, 3' modification, nucleobase modification, or modified internucleotide linkage), include unmodified cytosine, uracil, thymine, adenine, and guanine.

Nucleotide analogs include nucleotides having modifications in the chemical structure of the base, sugar and/or phosphate, including, but not limited to, 5-position pyrimidine modifications, 8-position purine modifications, modifications at cytosme exocyclic amines, and substitution of 5-bromo-uracil; and 2'-position sugar modifications, including but not limited to, sugar-modified ribonucleotides in which the 2'-OH is replaced by a group such as an H, OR, R, halo, SH, SR, $NH_2$, NHR, $NR_2$, or CN, wherein R is an alkyl moiety as defined herein. Nucleotide analogs are also meant to include nucleotides with bases such as inosine, queuosine, xanthine, sugars such as 2'-methyl ribose, non-natural phosphodiester linkages such as methylphosphonates, phosphorothioates and peptides.

Modified bases refer to nucleotide bases such as, for example, adenine, guanine, cytosine, thymine, and uracil, xanthine, inosine, and queuosine that have been modified by the replacement or addition of one or more atoms or groups. Some examples of types of modifications that can comprise nucleotides that are modified with respect to the base moieties, include but are not limited to, alkylated, halogenated, thiolated, aminated, amidated, or acetylated bases, in various combinations. More specific modified bases include, for example, 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles. The term nucleotide is also meant to include what are known in the art as universal bases. By way of example, universal bases include but are not limited to 3-nitropyrrole, 5-nitroindole, or nebularine.

Further, the term nucleotide also includes those species that have a detectable label, such as for example a radioactive or fluorescent moiety, or mass label attached to the nucleotide.

Nucleotide Unit

The phrase "nucleotide unit" refers to a single nucleotide residue and is comprised of a modified or unmodified nitrogenous base, a modified or unmodified sugar, and a modified or unmodified moiety that allows for linking of two nucleotides together or a conjugate that precludes further linkage.

Off-Target

The term "off-target" and the phrase "off-target effects" refer to any instance in which an siRNA or shRNA directed against a given target causes an unintended effect by interacting either directly or indirectly with another mRNA sequence, a DNA sequence or a cellular protein or other moiety. For example, an "off-target effect" may occur when there is a simultaneous degradation of other transcripts due to partial homology or complementarity between that other transcript and the sense and/or antisense strand of the siRNA or shRNA.

Overhang

The term "overhang" refers to terminal non-base pairing nucleotide(s) resulting from one strand or region extending beyond the terminus of the complementary strand to which the first strand or region forms a duplex. One or both of two polynucleotides or polynucleotide regions that are capable of forming a duplex through hydrogen bonding of base pairs may have a 5' and/or 3' end that extends beyond the 3' and/or 5' end of complementarity shared by the two polynucleotides or regions. The single-stranded region extending beyond the 3' and/or 5' end of the duplex is referred to as an overhang.

Pharmaceutically Acceptable Carrier

The phrase "pharmaceutically acceptable carrier" includes, but is not limited to, compositions that facilitate the introduction of dsRNA, dsDNA, or dsRNA/DNA hybrids into a cell and includes but is not limited to solvents or dispersants, coatings, anti-infective agents, isotonic agents, and agents that mediate absorption time or release of the inventive polynucleotides and siRNAs.

Polynucleotide

The term "polynucleotide" refers to polymers of nucleotides, and includes but is not limited to DNA, RNA, DNA/RNA hybrids including polynucleotide chains of regularly and irregularly alternating deoxyribosyl moieties and ribosyl moieties (i.e., wherein alternate nucleotide units have an —OH, then an —H, then an —OH, then an —H, and so on at the 2' position of a sugar moiety), and modifications of these kinds of polynucleotides wherein the attachment of various entities or moieties to the nucleotide units at any position are included. Unless otherwise specified, or clear from context, the term "polynucleotide" includes both unimolecular siRNAs and siRNAs comprised of two separate strands.

Polyribonucleotide

The term "polyribonucleotide" refers to a polynucleotide comprising two or more modified or unmodified ribonucleotides and/or their analogs.

Ribonucleotide and Ribonucleic Acid

The term "ribonucleotide" and the phrase "ribonucleic acid" (RNA), refer to a modified or unmodified nucleotide or polynucleotide comprising at least one ribonucleotide unit. A ribonucleotide unit comprises an oxygen attached to the 2' position of a ribosyl moiety having a nitrogenous base attached in N-glycosidic linkage at the 1' position of a ribosyl moiety, and a moiety that either allows for linkage to another nucleotide or precludes linkage.

RNA Interference and RNAi

The phrase "RNA interference" and the term "RNAi" are synonymous and refer to the process by which a polynucleotide or siRNA comprising at least one ribonucleotide unit exerts an effect on a biological process. The process includes, but is not limited to, gene silencing by degrading mRNA, attenuating translation, interactions with tRNA, rRNA, hnRNA, cDNA and genomic DNA, as well as methylation of DNA with ancillary proteins.

Second Nucleotide

The term "second nucleotide" or "nucleotide number 2" refer to the second nucleotide within a duplex region on either the sense or antisense strand, counting from the 5' end of each respective strand. The nucleotide may be paired or, for example in the case of a mismatch, unpaired.

Second 5' Terminal Antisense Nucleotide

The phrase "second 5' terminal antisense nucleotide" refers to the nucleotide that is immediately adjacent to the first 5' terminal antisense nucleotide and attached to the 3' position of the first 5' terminal antisense nucleotide. Thus, it is the second most 5' nucleotide of the antisense strand or region within the set of nucleotides for which there are complementary sense nucleotides.

Second 5' Terminal Sense Nucleotide

The phrase "second 5' terminal sense nucleotide" refers to the nucleotide that is immediately adjacent to the first 5' terminal sense nucleotide and attached to the 3' position of the first 5' terminal sense nucleotide. Thus, it is the second most 5' nucleotide of the sense strand or region within the set of nucleotides for which there are corresponding antisense nucleotides.

Sense Strand

The phrase "sense strand" refers to a polynucleotide or region that has the same nucleotide sequence, in whole or in part, as a target nucleic acid such as a messenger RNA or a sequence of DNA. The phrase "sense strand" includes the sense region of both polynucleotides that are formed from two separate strands, as well as unimolecular siRNAs that are capable of forming hairpin structures. When a sequence is provided, by convention, unless otherwise indicated, it is the sense strand (or region), and the presence of the complementary antisense strand (or region) is implicit. The phrases "sense strand" and "sense region" are intended to be equivalent and are used interchangeably.

siRNA or Short Interfering RNA

The term "siRNA" and the phrase "short interfering RNA" refer to unimolecular nucleic acids and to nucleic acids comprised of two separate strands that are capable of performing RNAi and that have a duplex region that is between 18 and base pairs in length. Additionally, the term siRNA and the phrase "short interfering RNA" include nucleic acids that also contain moieties other than ribonucleotide moieties, including, but not limited to, modified nucleotides, modified internucleotide linkages, non-nucleotides, deoxynucleotides and analogs of the aforementioned nucleotides.

siRNAs can be duplexes and can also comprise unimolecular polynucleotides. Such unimolecular molecules comprise regions of self-complementarity (a stem) whereby nucleotides from one region of the polynucleotide pair with another region of the polynucleotide (thus forming a duplex), and are separated by a loop. Such unimolecular molecules can vary in size and design and are referred to by a variety of names including but not limited to hairpins, short hairpin RNAs (shRNAs), microRNAs (mRNAs) and short temporal RNAs (stRNAs). The length of the stem region in these molecules can vary between 18 and 45 nucleotides in length. Similarly, the size of the loop can vary between 4 and 23 nucleotides and can comprise nucleotide, non-nucleotide, and nucleotide-non-nucleotide compositions.

When the siRNAs are hairpins, the sense strand and antisense strand are part of one longer molecule.

Substantial Complementarity

Substantial complementarity refers to polynucleotide strands exhibiting 80% or greater complementarity.

Preferred Embodiments

The present invention will now be described in connection with preferred embodiments. These embodiments are presented in order to aid in an understanding of the present invention and are not intended and should not be construed to limit the invention in any way. All alternatives, modifications and equivalents that may become apparent to those of ordinary skill upon reading this disclosure are included within the spirit and scope of the present invention.

According to a first embodiment, the present invention is directed to a double stranded ribonucleotide comprising:

a. a sense strand, wherein said sense strand comprises
   i. a first 5' sense nucleotide, wherein said first 5' sense nucleotide comprises a first 2'-O-alkyl modification, and
   ii. a second 5' sense nucleotide, wherein said second 5' sense nucleotide comprises a second 2'-O-alkyl modification; and
b. an antisense strand, wherein said antisense strand comprises
   i. a first 5' antisense nucleotide, wherein said first 5' antisense nucleotide is phosphorylated on the 5' carbon, and
   ii. a second 5' antisense nucleotide, wherein said second 5' antisense nucleotide comprises a third 2'-O-alkyl modification, wherein said sense strand and said antisense strand are capable of forming a duplex of 18-24 base pairs of nucleotides that has at least 80% complementarity over the range of the duplex, and within said duplex said first 5' sense nucleotide is the 5' most nucleotide of the sense strand, said second 5' sense nucleotide is immediately adjacent to and downstream of the first 5' sense nucleotide, said first 5' antisense nucleotide is the 5' most nucleotide of the antisense strand and said second 5' antisense nucleotide is immediately adjacent to and downstream of the first 5' antisense nucleotide.

In one embodiment, the first 5' antisense nucleotide comprises an —OH at its 2' position. In this embodiment, the first 2'-O-alkyl modification preferably comprises 2'-O-methyl, the second 2'-O-alkyl modification preferably comprises 2'-O-methyl, and the third 2'-O-alkyl modification preferably comprises 2'-O-methyl. In a preferred embodiment, the double stranded ribonucleotide of this embodiment comprises a 2'-OH on all nucleotides other than the first 5' sense nucleotide, the second 5' sense nucleotide, and the second 5' antisense nucleotide.

In another embodiment, the first 5' antisense nucleotide comprises a fourth 2'-O-alkyl modification. In this embodiment, the first 2'-O-alkyl modification comprises 2'-O-methyl, the second 2'-O-alkyl modification comprises 2'-O-methyl, the third 2'-O-alkyl modification comprises 2'-O-methyl, and the fourth 2'-O-alkyl modification comprises 2'-O-methyl. In a preferred embodiment, this embodiment further comprises a 2'-OH on all nucleotides other than on the first 5' sense nucleotide, the second 5' sense nucleotide, the first 5' antisense nucleotide, the said second 5' antisense nucleotide.

The authors recognize that the second position of the antisense (and sense) strand of siRNAs that are between 18-24 bp in length, is (unlike any other base or basepair in the siRNA) a key position in mediating the silencing of targets other than the intended target (i.e., off-targets) and that modifications/alterations of this position can be used to eliminate off-target effects generated by any siRNA. As shown in Example 8 of this document, chemical modification of position 2 effectively eliminates off-target effects generated by that strand as measured by microarray analysis. Similarly, Example 9 demonstrates how addition of basepair mismatches at position 2 (and other positions) can dramatically alter the pattern of off-target effects. The ability to shift or alter off-target effects is particularly valuable in instances where down regulation of one or more off-target genes induces an undesirable phenotype. Evidence that such off-target induced phenotypes exist and can be eliminated by alterations at position 2 of the AS strand is provided in Example 10.

Knowledge of the importance of position 2 (on either the sense and/or antisense strand) enables one to effectively eliminate off-target effects by a variety of strategies. For instance, addition of 2' modification (such as a 2'-O-alkyl modification) at this position on e.g. the antisense strand, can eliminate the off-target effects attributable to this strand. Similarly, one can substitute a base at position 2 of, e.g., the antisense strand, such that a mismatch now exists between the intended target mRNA and the antisense strand of the siRNA. While a single basepair mismatch (or a modification) at this position will not dramatically alter the ability of this siRNA to silence the intended target, it will alter the ability of the siRNA to silence off-targets. It should be noted that basepair mismatches at positions other than position 2 of e.g. the antisense strand (e.g. at positions 3, 4, 5, 6, 7, or 8 in the antisense strand of an siRNA duplex where numbering references a location with respect to the 5 terminus of the antisense strand, with position 2 being the nucleotide that is adjacent to the 5'-most nucleotide on the antisense strand) can also reduce, eliminate, or alter specific off-target effects. Suitable mismatches include, but are not limited to A-G pairings, A-A pairings, G-G pairings, C-C pairings, and U-U pairings. Moreover, the position of the mismatch is preferably at position 3, 4, 5, 6, 7, or 8 of the antisense or sense strand. Most preferably, the position of the mismatch is at position 2 of the antisense or sense strand. It should be noted that while use of basepair substitutions such as this can eliminate the original set of off-targets, new off-targets (resulting from complementarity to a new set of genes) can result. For this reason, it is more preferable that the chemical modifications described in this invention are added to the siRNA that eliminate or minimize all off-target effects. Thus modifications including but not limited to: 1) chemical modifications of the base, sugar, or internucleotide linkage of nucleotide number two of the sense and/or antisense strand; (2) nucleotide or nucleotide pair alterations at position 2, 3, 4, 5, 6, 7, or 8 of the sense and/or antisense strand of an siRNA, including substitution of a base or base pair such that a mismatch is generated between a potential off-target mRNA and either the sense and/or antisense strand of the siRNA; (3) nucleotide or nucleotide pair alterations at position 2 of the sense and/or antisense strand of an siRNA, including deletion of a nucleotide or nucleotide pair at position 2, 3, 4, 5, 6, 7, or 8 such that a bulge is generated in the off-target transcript when it anneals with the sense and/or antisense strand of the siRNA; (4) nucleotide or nucleotide pair alterations at position 2, 3, 4, 5, 6, 7, or 8 of the sense and/or antisense strand of an siRNA, including insertions of a nucleotide or nucleotide pair at position 2, such that a bulge is generated in the sense or antisense strand of the siRNA when it anneals with the off-target mRNA message, or (5) nucleotide or nucleotide pair alterations at position 2, 3, 4, 5, 6, 7, or 8 of the sense and/or antisense strand of an siRNA, including the presence of a basic nucleotides, or nucleotides with modifications at position C3 of the sugar ring, can be used to eliminate, minimize, or alter off-target effects in critical instances. The above-described mismatches can be used in conjunction with any of the embodiments described herein to reduce off-target effects.

That said, preferably, the siRNA of the first embodiment comprises from 18-24 base pairs, exclusive of overhangs.

These molecules are not processed (or processed poorly) by the Type III RNase, Dicer, and for this reason, the pattern of modifications are preserved within the cell. Preferably, the sense strand and antisense strand are at least substantially complementary over the range of base pairs, and more preferably 100% complementary over this range. Preferably, the polynucleotide is RNA.

The siRNA of the first embodiment may also contain overhangs of 1-6 nucleotides at either the 5' or 3' end of either the sense strand and/or the antisense strand. However, preferably if there are any overhangs, they are on the 3' end of the sense strand and/or the antisense strand. Additionally, preferably any overhangs are six or fewer bases in length, more preferably two or fewer bases in length. Most preferably, there are either no overhangs, or overhangs of two bases on one or both of the sense strand and antisense strand at the 3' end. Because overhanging nucleotides are frequently removed by one or more intracellular enzymatic processes or events, thus leaving an unphosphorylated 5'-nucleotide, it is preferable not to have overhangs on the 5' end of the antisense strand. In addition, overhangs can contain one or more stabilizing modifications, such as halogen modification of the 2' position or internucleotide modifications such as phosphorothioate, phosphorodithioate, or methylphosphonate modifications.

In further reference to the first embodiment, the phosphorylation of the first 5' terminal antisense nucleotide refers to the presence of one or more phosphate groups attached to the 5' carbon of the sugar moiety of the nucleotide. Preferably there is only one phosphate group.

According to the present embodiment, the modification of the first and second 5' sense nucleotides and the second 5' antisense nucleotides are a 2'-O-alkyl group. Preferably the modification is selected from the group consisting of 2'-O-methyl, 2'-O-ethyl, 2'-O-propyl, 2'-O-isopropyl, 2'-O-butyl, 2-O-isobutyl, 2'-O-ethyl-O-methyl (—OCH$_2$CH$_2$OCH$_3$), and 2'-O-ethyl-OH (—OCH$_2$CH$_2$OH). Most preferably, the 2'-O-alkyl modification is a 2'-O-methyl moiety. Further, there is no requirement that the modification be the same on each of the first 5' sense nucleotide, the second 5' sense nucleotide, or the second antisense nucleotide. However, as a matter of practicality with respect to synthesizing the molecules of the present invention, it may be desirable to use the same modification throughout.

Alternatively, the molecule can have a sense strand where in the sense strand comprises a first 5' sense nucleotide, wherein said first 5' sense nucleotide comprises a first 2'-O-alkyl modification, and a second 5' sense nucleotide, wherein said second 5' sense nucleotide comprises a second 2'-O-alkyl modification; and all Cs and Us (other than any of the aforementioned positions) are modified with a 2'-O-alkyl modification; and an antisense strand, wherein said antisense strand comprises a first 5' antisense nucleotide, wherein said first 5' antisense nucleotide is phosphorylated, and a second 5' antisense nucleotide, wherein said second 5' antisense nucleotide comprises a third 2'-O-1-alkyl modification, and all Cs and Us (other than if present at the second 5' antisense nucleotide) are modified with a 2° F. Furthermore, these molecules can comprise a 2 nucleotide overhang on the 3' end of either or both strands and said overhang can further comprise a stabilized internucleotide linkage between: (1) the two nucleotides of the overhang; and (2) the penultimate nucleotide of the overhang and the final nucleotide of the duplexed region, comprises a phosphorothioate, a phosphorodithioate, or methylphosphonate linkage.

Alternatively, the molecule can contain a sense strand wherein the sense strand comprises a first 5' sense nucleotide, wherein said first 5' sense nucleotide comprises a 5' deoxy nucleotide; and an antisense strand, wherein said antisense strand comprises a first 5' antisense nucleotide, wherein said first 5' antisense nucleotide is phosphorylated at the 5' carbon, and a second 5' antisense nucleotide, wherein said second 5' antisense nucleotide comprises a 2'-O-alkyl modification. For a strand to participate in gene silencing by the RNAi pathway, the 5' end of that strand must be phosphorylated at the 5' carbon position. The presence of a 5' deoxynucleotide on the 5' end removes the functional group (—OH) from that strand, thus eliminating the ability of resident kinases to add a phosphate at this position. Without a phosphate group at the 5' terminus, the ability of this strand to be involved in RISC-mediated on- and off-target silencing is reduced.

While the invention identifies 2'-O-alkyl groups at the above-referenced positions, the inventors recognize that other chemical modification groups at similar or identical positions can also be used to minimize off-target effects. For example, the 2' modified nucleotide can be a 2' halogen modified nucleotide, a 2' amine modified nucleotide, and a 2' alkyl modified nucleotide if such modifications are included under conditions that minimize off-target effects. Where the modification is a halogen, the halogen is preferably fluorine. Where the 2' modified nucleotide is a 2' amine modified nucleotide, the amine is preferably —NH$_2$. Where the 2' modified nucleotide is a 2'-alkyl modification, preferably the modification is selected from the group consisting of methyl, ethyl, propyl, isopropyl, butyl, or isobutyl moiety. Most preferably, a 2' methyl modification, wherein the carbon of the methyl moiety is attached directly to the 2' carbon of the sugar moiety, is used.

As stated above, the modification pattern described in the first embodiment is applicable for molecules that are not processed by Dicer. Yet in some instances, longer duplexes (e.g., 25-30 basepairs) are preferred. These molecules are potential substrates for Dicer and for that reason, shifts in the pattern of modification and distinct patterns of overhang length and position must be incorporated into duplex design to insure that the entire complement of modifications described in the first embodiment are present in the final duplex, post-Dicer processing. In one non-limiting example, the structure of the duplex termini are engineered to guarantee the final product carries the necessary modifications in the appropriate positions. The side in which Dicer enters a duplex can be biased by the presence or absence of overhangs. Furthermore, the position of Dicer cleavage can be manipulated by varying the length of the 3' overhang. Thus, for example, one preferred design for molecules that are 26 basepairs or longer includes: (1) a 1, 2, or 3 nucleotide overhang on the 3' end of the sense strand, and no overhangs on the opposite end of the duplex; (2) a 2'-O-alkyl modification on the second antisense nucleotide (counting from the 5' end of the strand); (3) phosphorylation of the 5' carbon of the first antisense nucleotide; and (4) paired 2'-O-alkyl modifications on sense strand nucleotides 21 and 22, 22 and 23, or 23 and 24 (counting from the 3' end of the sense strand, overhang included). Addition of the 3' sense strand overhang biases the side in which Dicer enters the duplex (i.e., Dicer will preferably enter the side of the molecule that contains the overhang rather than the blunt end of the molecule). This ensures the preservation/retention of both antisense modifications (i.e., the 2'-O-alkyl modification on the second antisense nucleotide, and the 5' phosphate group on the first antisense nucleotide) in the final, post-Dicer processing, siRNA. In addition, the positions of the sense strand modifications ensure that following Dicer processing, these modifications will be present on the terminal sense nucleotides (sense nucleotides 1 and 2) of the final, processed siRNA (see FIG. 1).

According to a second embodiment, the present invention is directed to a unimolecular siRNA capable of forming a hairpin siRNA, said unimolecular siRNA comprising:

a. a sense strand, comprising a sense region that comprises i. a first 5' sense nucleotide, wherein said first 5' sense nucleotide comprises a first 2'-O-alkyl modification, and ii. a second 5' sense nucleotide, wherein said second 5' sense nucleotide comprises a second 2'-O-alkyl modification; and b. an antisense strand, comprising an antisense region that comprises i. a first 5' antisense nucleotide, wherein said first 5' antisense nucleotide is phosphorylated on the 5' carbon, and ii. a second 5' antisense nucleotide, wherein said second 5' antisense nucleotide comprises a third 2'-O-alkyl modification, and a loop region, wherein said loop region is located between said sense region and said antisense region and wherein said sense strand and said antisense strand are capable of forming a duplex of 18-24 base pairs of nucleotides that has at least 80% complementarity over the range of the duplex, and within said duplex said first 5' sense nucleotide is the 5' most nucleotide of the duplex region, and said second 5' sense nucleotide is immediately adjacent to and downstream of the first 5' sense nucleotide, said first 5' antisense nucleotide is the 5' most nucleotide of the antisense strand of the duplex region and said second 5' antisense nucleotide is immediately adjacent to and downstream of the first 5' antisense nucleotide.

According to this embodiment, the range of modifications is the same as those for the first embodiment. However, because the polynucleotide is unimolecular and is capable of forming a hairpin, and not two separate strands, there is one contiguous molecule that comprises both a sense region and an antisense region. Preferably, the sense region and the antisense region are at least substantially complementary, more preferably 100% complementary. Preferably the sense region and the antisense region comprise 19-35 base pairs, more preferably from 24-35 base pairs, and most preferably from 26-31 base pairs. Preferably, the entire length of the unimolecular siRNA contains fewer than 100 bases, more preferably fewer than 85 bases. Preferably the nucleotide is RNA.

Figure 2:
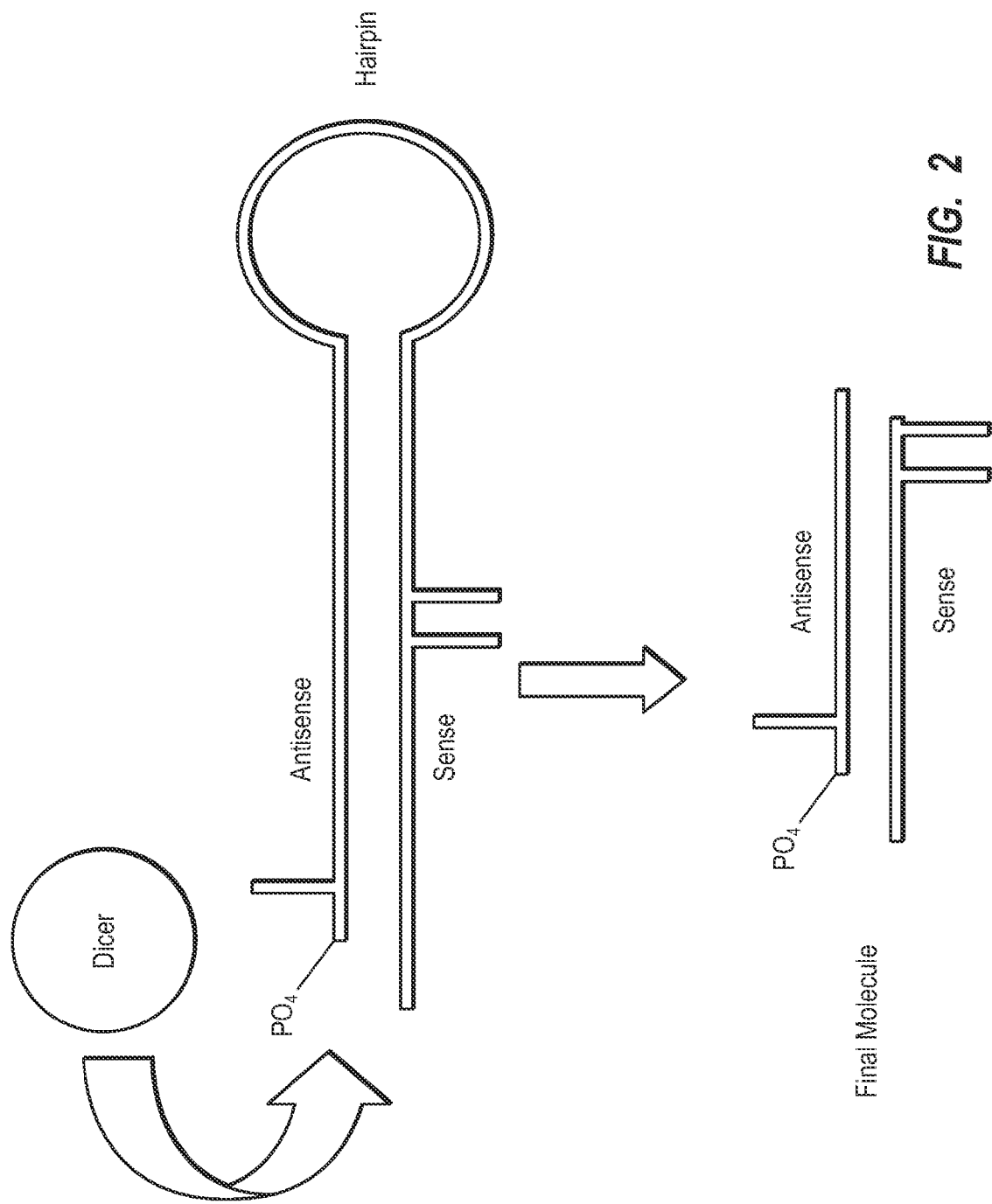
FIG. 2 depicts the relationship between positioning of one embodiment of the invention's modifications in hairpins. Optimal design for the molecules ensures that following Dicer digestion, the final functional duplex contains the depicted invention's modification pattern. Note, in the initial Dicer substrate, the free (open) end of the molecule can be blunt ended or contain a 3' overhang. Furthermore, the unimolecular molecule can be organized in either a 5' antisense-loop-sense or 5' sense-loop-antisense orientation.

Hairpins comprise two major components including a stem (which is a double stranded region pairing the antisense strand and the sense strand) and a loop. Optionally, an overhang sequence can be added to the 5', 3' or both ends of the molecule. Preferably, when an overhang is present, it is associated with the 3' end of the molecule. When designing a unimolecular siRNA, the hairpin can be designed as a left-handed hairpin (e.g., 5'-AS-Loop-S) or a right-handed hairpin (e.g., 5'-S-Loop-AS). Preferably, the hairpin is a left-handed hairpin. This construction is desirable because it is easier to phosphorylate the terminal antisense nucleotide. As was the case with double stranded siRNA, the length of the stem of the molecule determines whether or not it will be processed by Dicer. As hairpins containing longer stem structures are substrates for Dicer, the position of the chemical modifications must be adjusted to ensure that the final, post-Dicer processing product contains the modifications in the desired positions. Preferably, the post-Dicer processed molecule contains all of the modifications described in the first embodiment. In one non-limiting example, preferred hairpin designs for unimolecular molecules that have stems that are longer than 24 bases include the following properties: (1) a left-handed hairpin design, (2) a 1-3 nucleotide 3' overhang, (3) a phosphate group on the 5' carbon of the 5' most nucleotide, (4) a 2'-O-alkyl (preferably an O-methyl) modification of the second antisense nucleotide, and (5) paired 2'-O-alkyl modifications on sense strand nucleotides 21 and 22, 22 and 23, or 23 and 24 (counting from the 3' end of the sense strand, overhang included). Addition of the 3' sense strand overhang enhances the ability of Dicer to enter the hairpin on the 5' AS end of the molecule. In addition, the positions of the sense strand modifications ensure that following Dicer processing, these modifications will be present on the terminal sense nucleotides (sense nucleotides 1 and 2 that have complementary bases on the antisense strand) of the final, processed siRNA (see FIG. 2).

The hairpin may comprise a loop structure, which preferably comprises from four to ten bases. The bases of the loop can be modified. Alternatively, the loop can comprise non-nucleotide components such as those described in U.S. patent application Ser. No. 10/635,108, published on Mar. 25, 2004, as U.S. 2004/0058886 A1. Preferable sequences of the loop structure include, for example, 5'-UUCG-3' (SEQ. ID NO. 18), 5'-UUUGUGUAG-3' (SEQ. ID NO. 19), 5'-CUUCCU-GUCA-3' (SEQ. ID NO. 20), 5'-AUAUGUG-3' (SEQ. ID NO. 21), or any other loop identified in prior or pre-mRNA.

As described previously, the unimolecular siRNA of the present invention may ultimately be processed by cellular machinery such that they are converted into two separate strands. Further, these unimolecular siRNA may be introduced into the cell with less than all modifications, and modified in the cell itself through the use of natural processes or processing molecules that have been introduced (e.g., phosphorylation in the cell). However, preferably the siRNA is introduced with all modifications already present. (Similarly, the strands of the first embodiment are preferably introduced into the cell with all modifications, though the antisense strand could, e.g., be modified after introduction.) If a hairpin is processed by Dicer, the resulting hairpin should retain the modifications of the various embodiments described herein.

The above-described modifications should not be construed to suggest that no other moieties may be modified in addition to the nucleotides described, that also contribute to minimizing off-target effects or enhance other properties of the siRNA (such as improved stability or functionality). Other types of modifications are permissible so long as they do not unacceptably increase off-target effects. In certain embodiments, such additional modifications can be added to one, two, three, or more consecutive nucleotides or every-other nucleotide of the sense strand. Alternatively, additional modifications can be confined to specific positions that have been identified as being key to sense strand entrance and/or use by RISC. As mentioned previously, further, additional modifications, such as 2'-O-alkyl groups (or other 2' modifications) can be added to one or more, preferably all, pyrimidines (e.g., C and/or U nucleotides) of the sense strand and/or 2° F. modifications (or other halogen modifications) can be added to one or more, preferably all pyrimidines (e.g., C and/or U nucleotides) of the antisense strand other than to nucleotides that are otherwise modified as specified above. Modifications such as 2° F. or 2'-O-alkyl of some or all of the Cs and Us of the antisense and/or sense strand (respectively) and other of the nucleotides specified above can greatly enhance the stability of the siRNA/shRNA molecules carrying the modifications described in embodiments 1 and 2, without appreciably altering target specific silencing.

Further, if a label is used in conjunction with the invention, these agents can be useful as tracking agents, which would assist in detection of transfection, as well as detection of where in the cell the molecule is present. Examples of commonly used labels include, but are not limited to, a fluorescent label, a radioactive label or a mass label.

Additionally, stabilization modifications that are addressed to the phosphate backbone may also be included in the siRNAs for some applications of the present invention. For example, at least one phosphorothioate and/or methylphosphonate may be substituted for the phosphate group at some or all 3' positions of any or all pyrimidines in the sense and/or antisense strands of the oligonucleotide backbone, as well as in any overhangs, loop structures or stem structures that may be present. Phosphorothioate (and methylphosphonate) analogues arise from modification of the phosphate groups in the oligonucleotide backbone. In the phosphorothioate, the phosphate 0 is replaced by a sulfur atom. In methylphosphonates, the oxygen is replaced with a methyl group. Additionally, phosphorothioate 3' modifications may be used instead of and independent of 2' fluoro modifications to increase stability of an siRNA molecule. These modifications may be used in combination with the other modifications disclosed herein, or independent of those modifications in siRNA applications.

In other embodiments, there can still be additional modifications such as those described as follows: (1) an antisense strand containing a 2' modification (preferably a 2'-O-alkyl modification) on the second antisense nucleotide, plus a phosphate group on carbon 5 of the first antisense nucleotide; plus either (2) positions 1, 2, and 3 of the sense strand (or sense region in an shRNA), counting from the 5' end of that strand are modified with 2' modifying groups (preferably a 2'-O-alkyl modification), or (3) the first sense nucleotide counting from the 5' end of that strand is a 5' deoxynucleotide. Either combination of modifications may be beneficial in substantially reducing both sense and antisense strand induced off-target effects.

In another embodiment, the molecule comprises the following modifications: (1) the second terminal antisense nucleotide contains a 2'-O-alkyl modification; and (2) the first terminal antisense nucleotide contains a phosphate group on the 5' carbon; and (3) the 5' carbon of the first terminal nucleotide of the sense strand comprises any group known in the art that is suitable for blocking the hydroxyl group from accepting or being converted to a phosphate group. Preferably, the 5' terminal nucleotide blocking group comprises a 5'-O-alkyl, a 5' amine blocking group, or 5' azide blocking group.

In other embodiments, any of the compositions of the present invention can further comprise a 3' cap. The 3' cap can be, for example, an inverted deoxythymidine.

In other embodiments of the present invention, any of the compositions can comprise a conjugate. The conjugate can be selected from the group consisting of amino acids, peptides, polypeptides, proteins, sugars, carbohydrates, lipids, polymers, nucleotides, polynucleotides, and combinations thereof. The conjugate can be, for example, cholesterol or PEG. The conjugate can further comprise a label, such as, for example, a fluorescent label. The fluorescent label can be selected from the group consisting of TAMRA, BODIPY, Cy3, Cy5, fluoroscein, and Dabsyl. Alternatively, the fluorescent label can be any fluorescent label known in the art.

In other embodiments, the compositions of the present invention can comprise at least one 2'-orthoester modification, wherein the 2'-orthoester modification is preferably a 2'-bis(hydroxy ethyl) orthoester modification.

The duplex or duplex region can comprise one or more mismatches. For example, a duplex region can have one or more mismatches at any one or combination of positions 2 to 8 of, for example, the antisense strand. Nevertheless, the duplex region is considered in this case to include one or more mismatches where one or more mismatches can be counted among the 18-24 nucleotide basepairs that are at least 80% complementary. That the duplex region can comprise at least one mismatch can be included in any of the embodiments described herein.

The above described modifications of the present invention may be combined with siRNA that contains sequences that were selected at random, or according to any rational design selection procedure, for example, the rational design algorithm described in U.S. patent application Ser. No. 10/714,333, filed on Nov. 14, 2003, entitled "Functional and Hyperfunctional siRNA"; in international patent application number PCT/US2003/036787, published on Jun. 3, 2004 as WO 2004/045543 A2, entitled "Functional and Hyperfunctional siRNA"; and in U.S. patent application Ser. No. 10/940,892, filed on Sep. 14, 2004, entitled "Methods and Compositions for Selecting siRNA of Improved Functionality." Additionally, it may be desirable to select sequences in whole or in part based on internal thermal stability, which may facilitate processing by cellular machinery.

It should be noted that the modifications of the first and second embodiment of the present invention may have different effects depending on the functionality of the siRNA that are employed. Thus, in highly functional siRNA, the modifications of the present invention may cause a molecule to lose a certain amount of functionality, but would nonetheless be desirable because off-target effects are reduced. By contrast when moderately or poorly functional siRNA are used, there is very little functionality decrease and in some cases, functionality can increase.

A variety of approaches can be used to identify both the type of molecule and the key position needed to eliminate sense and/or antisense strand off-targeting effects. In one non-limiting example, a modification-function walk is performed. In this procedure, a single type of modification is added to one or more nucleotides across the sense and/or antisense strand. Subsequently, modified and unmodified molecules are tested for: (1) functionality; and (2) off-targeting effects, by one of several methods. Thus, for example, 2'-O-Me groups can be added to positions 1 and 2, 3 and 4, 5 and 6, 7 and 8, 9 and 10, 11 and 12, 13 and 14, 15 and 16, 17 and 18, or 18 and 19 of either the sense and/or antisense strand and tested for functionality (e.g., by measuring the ability of these molecules to silence specific targets) and off-target effects. If key positions are identified that eliminate some or all off-targeting, but result in a loss of duplex functionality, then a second round of modification walks, whereby additional chemical groups (e.g., 5' phosphate on the 5' end of the antisense strand), mismatches, or bulges that are suspected to increase duplex functionality, can be added to molecules that already contain the modification that eliminates off-targeting.

In order to determine what modifications are permissible, several non-limiting assays can be performed to identify modifications that limit off-target effects. In one non-limiting example, the sense or antisense strand (carrying the modification being tested) can be labeled with one of many labeled nucleotides. Subsequently, a binding assay can be performed whereby the affinity of RISC for, e.g., the modified sense strand can be compared with that of the unmodified form. Alternatively, siRNA containing various modifications can be transfected into cells by a variety of methodologies and cultures can subsequently be assessed by microarray analysis to determine whether the modifications alter the number and pattern of off-targeted genes.

According to a third embodiment, the present invention is directed to a method for minimizing off-target effects, said method comprising exposing a modified siRNA containing the modifications described in embodiment 1, to a target nucleic acid, or a cell or organism that is either expressing the target nucleic acid or capable of expressing the target nucleic acid.

According to a fourth embodiment, the present invention is directed to a method for minimizing off-target effects, said method comprising exposing a unimolecular siRNA containing the modifications described in second embodiment to a target nucleic acid, or a cell or organism that is either expressing the target nucleic acid or capable of expressing the target nucleic acid.

In various embodiments, a 3' overhang of 1 to 6 bases on at least one of the sense strand and the antisense strand can be present. The overhang can be present with any of the embodiments described herein, unless otherwise specified or implicit from the context.

Because the ability of the dsRNA of the present invention to retain functionality and exhibit improved specificity is not dependent on the sequence of the bases, the cell type, or the species into which it is introduced, the present invention is applicable across a broad range of organisms, including but not to limited plants, animals, protozoa, bacteria, viruses and fungi. The present invention is particularly advantageous for use in mammals such as cattle, horse, goats, pigs, sheep, canines, rodents such as hamsters, mice, and rats, and primates such as, gorillas, chimpanzees, and humans.

The present invention may be used advantageously with diverse cell types, including but not limited to primary cells, germ cell lines and somatic cells. The cells may be, for example, stem cells or differentiated cells. For example, the cell types may be embryonic cells, oocytes, sperm cells, adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes and cells of the endocrine or exocrine glands.

The present invention is applicable for use for employing RNA interference (and/or using as a control) directed against a broad range of genes, including but not limited to the 45,000 genes of a human genome, such as those implicated in diseases such as diabetes, Alzheimer's and cancer, as well as all genes in the genomes of the humans, mice, hamsters, chimpanzees, goats, sheep, horses, camels, pigs, dogs, cats, nematodes (e.g., *C. elegans*), flies (e.g., *D. melanogaster*), and other vertebrates and invertebrates.

The siRNAs of the present invention may be administered to a cell by any method that is now known or that comes to be known and that from reading this disclosure, one skilled in the art would conclude would be useful with the present invention. For example, the siRNAs may be passively delivered to cells. Passive uptake of modified siRNAs can be modulated, for example, by the presence of a conjugate such as a polyethylene glycol moiety or a cholesterol moiety at the 5' terminal of the sense strand and/or, in appropriate circumstances, a pharmaceutically acceptable carrier.

Other methods for delivery include, but are not limited to, transfection techniques employing DEAE-Dextran, calcium phosphate, cationic lipids/liposomes, microinjection, electroporation, immunoporation, and coupling of the siRNAs to specific conjugates or ligands such as antibodies, peptides, antigens, or receptors.

Preferably, the siRNAs comprise duplexes when they are administered.

Further, the method of assessing the level of gene silencing is not limited. Thus, the silencing ability of any given siRNA can be studied by one of any number of art tested procedures including but not limited to Northern analysis, Western Analysis, RT PCR, expression profiling, and others.

The polynucleotides of the present invention may be synthesized by any method that is now known or that comes to be known and that from reading this disclosure a person of ordinary skill in the art would appreciate would be useful to synthesize the molecules of the present invention. siRNA duplexes containing the specified modifications may be chemically synthesized using compositions of matter and methods described in Scaringe, S. A. (2000) "Advanced 5'-silyl-2'-orthoester approach to RNA oligonucleotide synthesis," Methods Enzymol. 317, 3-18; Scaringe, S. A. (2001) "RNA oligonucleotide synthesis via 5'-silyl-2'-orthoester chemistry," Methods 23, 206-217; Scaringe, S. and Caruthers, M. H. (1999) U.S. Pat. No. 5,889,136; Scaringe, S. and Caruthers, M. H. (1999) U.S. Pat. No. 6,008,400; Scaringe, S. (2000) U.S. Pat. No. 6,111,086; Scaringe, S. (2003) U.S. Pat. No. 6,590,093. The synthesis method utilizes nucleoside base-protected 5'-O-silyl-2'-O-orthoester-3'-O-phosph-oramidites to assemble the desired unmodified siRNA sequence on a solid support in the 3' to 5' direction. Briefly, synthesis of the required phosphoramidites begins from standard base-protected ribonucleosides (uridine, $N^4$-acetylcytidine, $N^2$-isobutyrylguanosine and N-isobutyryladenosine). Introduction of the 5'-O-silyl and 2'-O-orthoester protecting groups, as well as the reactive 3'-O-phosphoramidite moiety is then accomplished in five steps, including:

1. Simultaneous transient blocking of the 5'- and 3'-hydroxyl groups of the nucleoside sugar with Markiewicz reagent (1,3-dichloro-1,1,3,3,-tetraisopropyldisiloxane [TIPS-Cl$_2$]) in pyridine solution {Markiewicz, W. T. (1979) "Tetraisopropyldisiloxane-1,3- -diyl, a Group for Simultaneous Protection of 3'- and 5'-Hydroxy Functions of Nucleosides," J. Chem. Research(S), 24-25}, followed by chromatographic purification;

2. Regiospecific conversion of the 2'-hydroxyl of the TIPS-nucleoside sugar to the bis(acetoxyethyl)orthoester [ACE derivative] using tris(acetoxyethyl)orthoformate in dichloromethane with pyridinium p-toluenesulfonate as catalyst, followed by chromatographic purification;

3. Liberation of the 5'- and 3'-hydroxyl groups of the nucleoside sugar by specific removal of the TIPS-protecting group using hydrogen fluoride and N,N,N"N'-tetramethylethylene diamine in acetonitrile, followed chromatographic purification;

4. Protection of the 5'-hydroxyl as a 5'-O-silyl ether using benzhydroxy-bis(trimethylsilyloxy)silyl chloride [BzH—Cl] in dichloromethane, followed by chromatographic purification; and 5. Conversion to the 3'-O-phosphoramidite derivative using bis(N,N-diisopropylamino)methoxyphosphine and 5-ethylthio-1H-tetrazole in dichloromethane/acetonitrile, followed by chromatographic purification.

The phosphoramidite derivatives are typically thick, colorless to pale yellow syrups. For compatibility with automated RNA synthesis instrumentation, each of the products is dissolved in a pre-determined volume of anhydrous acetonitrile, and this solution is aliquoted into the appropriate number of serum vials to yield a 1.0-mmole quantity of phosphoramidite in each vial. The vials are then placed in a suitable vacuum desiccator and the solvent removed under high vacuum overnight. The atmosphere is then replaced with dry argon, the vials are capped with rubber septa, and the packaged phosphoramidites are stored at −20 degrees C. until needed. Each phosphoramidite is dissolved in sufficient anhydrous acetonitrile to give the desired concentration prior to installation on the synthesis instrument.

The synthesis of the desired oligoribonucleotide is carried out using automated synthesis instrumentation. It begins with the 3'-terminal nucleoside covalently bound via its 3'-hydroxyl to a solid beaded polystyrene support through a cleavable linkage. The appropriate quantity of support for the desired synthesis scale is measured into a reaction cartridge, which is then affixed to synthesis instrument. The bound nucleoside is protected with a 5'-O-dimethoxytrityl moiety, which is removed with anhydrous acid (3% [v/v] dichloroacetic acid in dichloromethane) in order to free the 5'-hydroxyl for chain assembly.

Subsequent nucleosides in the sequence to be assembled are sequentially added to the growing chain on the solid support using a four-step cycle, consisting of the following general reactions:

1. Coupling: the appropriate phosphoramidite is activated with 5-ethylthio-1H-tetrazole and allowed to react with the free 5'-hydroxyl of the support bound nucleoside or oligonucleotide. Optimization of the concentrations and molar excesses of these two reagents, as well as of the reaction time, results in coupling yields generally in excess of 98% per cycle.

2. Oxidation: the internucleotide linkage formed in the coupling step leaves the phosphorous atom in its P(III) [phosphite] oxidation state. The biologically-relevant oxidation state is P(V) [phosphate]. The phosphorous is therefore oxidized from P(III) to P(V) using a solution of tert-butylhydroperoxide in toluene.

3. Capping: the small quantity of residual un-reacted 5'-hydroxyl groups must be blocked from participation in subsequent coupling cycles in order to prevent the formation of deletion-containing sequences. This is accomplished by treating the support with a large excess of acetic anhydride and 1-methylimidazole in acetonitrile, which efficiently blocks residual 5'-hydroxyl groups as acetate esters.

4. De-silylation: the silyl-protected 5'-hydroxyl must be deprotected prior to the next coupling reaction. This is accomplished through treatment with triethylamine trihydrogen fluoride in N,N-dimethylformamide, which rapidly and specifically liberates the 5'-hydroxyl without concomitant removal of other protecting groups (2'-O-ACE, N-acyl base-protecting groups, or phosphate methyl).

It should be noted that in between the above four reaction steps are several washes with acetonitrile, which are employed to remove the excess of reagents and solvents prior to the next reaction step. The above cycle is repeated the necessary number of times until the unmodified portion of the oligoribonucleotide has been assembled. The above synthesis method is only exemplary and should not be construed as limited the means by which the molecules may be made. Any method that is now known or that comes to be known for synthesizing siRNA and that from reading this disclosure one skilled in the art would conclude would be useful in connection with the present invention may be employed.

The siRNA duplexes of certain embodiments include two modified nucleosides (e.g., 2'-O-methyl derivatives) at the 5'-end of each strand. The 5'-O-silyl-2'-O-methyl-3'-O-phosphoramidite derivatives required for the introduction of these modified nucleosides are prepared using procedures similar to those described previously (steps 4 and 5 above), starting from base-protected 2'-O-methyl nucleosides (2'-O-methyl-uridine, 2'-O-methyl-$N^4$-acetylcytidine, 2'-O-methyl-$N^2$-isobutyrylguanosine and 2'-O-methyl-$N^6$-isobutyry-ladenosine). The absence of the 2'-hydroxyl in these modified nucleosides eliminates the need for ACE protection of these compounds. As such, introduction of the 5'-O-silyl and the reactive 3'-O-phosphoramidite moiety is accomplished in two steps, including:

1. Protection of the 5'-hydroxyl as a 5'-O-silyl ether using benzhydroxy-bis(trimethylsilyloxy)silyl chloride (BzH—Cl) in N,N-dimethylformamide, followed by chromatographic purification; and 2. Conversion to the 3'-O-phosphoramidite derivative using bis(N,N-diisopropylamino)methoxyphosphine and 5-ethylthio-1H-tetrazole in dichloromethane/acetonitrile, followed by chromatographic purification.

Post-purification packaging of the phosphoramidites is carried out using the procedures described previously for the standard nucleoside phosphoramidites. Similarly, the incorporation of the two 5'-O-silyl-2'-O-methyl nucleosides via their phosphoramidite derivatives is accomplished by twice applying the same four-step cycle described previously for the standard nucleoside phosphoramidites.

The siRNA duplexes of certain embodiments of this invention include a phosphate moiety at the 5'-end of the antisense strand. This phosphate is introduced chemically as the final coupling to the antisense sequence. The required phosphoramidite derivative (bis(cyanoethyl)-N,N-diisopropyla-mino phosphoramidite) is synthesized as follows in brief: phosphorous trichloride is treated one equivalent of N,N-diisopropylamine in anhydrous tetrahydrofuran in the presence of excess triethylamine. Then, two equivalents of 3-hydroxypropionitrile are added and allowed to react completely. Finally, the product is purified by chromatography. Post-purification packaging of the phosphoramidite is carried out using the procedures described previously for the standard nucleoside phosphoramidites. Similarly, the incorporation of the phosphoramidite at the 5'-end of the antisense strand is accomplished by applying the same four-step cycle described previously for the standard nucleoside phosphoramidites.

The modified, protected oligoribonucleotide remains linked to the solid support at the finish of chain assembly. A two-step rapid cleavage/deprotection procedure is used to remove the phosphate methyl protecting groups, cleave the oligoribonucleotide from the solid support, and remove the N-acyl base-protecting groups. It should be noted that this procedure also removes the cyanoethyl protecting groups from the 5'-phosphate on the antisense strand. Additionally, the procedure removes the acetyl functionalities from the ACE orthoester, converting the 2'-O-ACE protecting group into the bis(2-hydroxyethyl)orthoester. This new orthoester is significantly more labile to mild acid as well as more hydrophilic than the parent ACE group. The two-step procedure is briefly as follows:

1. The support-bound oligoribonucleotide is treated with a solution of disodium 2-carbamoyl-2-cyanoethylene-1,1-dithiolate trihydrate in N,N-dimethylformamide. This reagent rapidly and efficiently removes the methyl protecting groups from the internucleotide phosphate linkages without cleaving the oligoribonucleotide from the solid support. The support is then washed with water to remove excess dithiolate.

2. The oligoribonucleotide is cleaved from the solid support with 40% (w/v) aqueous methylamine at room temperature. The methylamine solution containing the crude oligoribonucleotide is then heated to 55 degrees C. to remove the protecting groups from the nucleoside bases. The crude orthoester-protected oligoribonucleotide is obtained following solvent removal in vacuo.

Removal of the 2'-orthoesters is the final step in the synthesis process. This is accomplished by treating the crude oligoribonucleotide with an aqueous solution of acetic acid and N,N,N',N'-tetramethyl ethylene diamine, pH 3.8, at 55 degrees C. for 35 minutes. The completely deprotected oligoribonucleotide is then desalted by ethanol precipitation and isolated by centrifugation.

In addition, incorporation of fluorescent labels at the 5'-terminus of a polynucleotide is a common and well-understood manipulation for those skilled in the art. In general, there are two methods that are employed to accomplish this incorporation, and the necessary materials are available from several commercial sources (e.g., Glen Research Inc., Sterling, Va., USA; Molecular Probes Inc., Eugene, Oreg., USA; TriLink BioTechnologies Inc., San Diego, Calif., USA; and others). The first method utilizes a fluorescent molecule that has been derivatized with a phosphoramidite moiety similar to the phosphoramidite derivatives of the nucleosides described previously. In such case, the fluorescent dye is appended to the support-bound polynucleotide in the final cycle of chain assembly. The fluorophore-modified polynucleotide is then cleaved from the solid support and deprotected using the standard procedures described above. This method has been termed "direct labeling."Alternatively, the second method utilizes a linker molecule derivatized with a phosphoramidite moiety that contains a protected reactive functional group (e.g., amino, sulfhydryl, carbonyl, carboxyl, and others). This linker molecule is appended to the support-bound polynucleotide in the final cycle of chain assembly. The linker-modified polynucleotide is then cleaved from the solid support and deprotected using the standard procedures described above. The functional group on the linker is deprotected either during the standard deprotection procedure, or by utilizing a subsequent group-specific treatment. The crude linker-modified polynucleotide is then reacted with an appropriate fluorophore derivative that will result in formation of a covalent bond between a site on the fluorophore and the functional group of the linker. This method has been termed "indirect labeling."

Once synthesized, the polynucleotides of the present invention may immediately be used or be stored for future use. Preferably, the polynucleotides of the invention are stored as duplexes in a suitable buffer. Many buffers are known in the art suitable for storing siRNAs. For example, the buffer may be comprised of 100 mM KCl, 30 mM HEPES-pH 7.5, and 1 mM $MgCl_2$. Preferably, the siRNAs of the present invention retain 30% to 100% of their activity when stored in such a buffer at 4 degrees C. for one year. More preferably, they retain 80% to 100% of their biological activity when stored in such a buffer at 4 degrees C. for one year. Alternatively, the compositions can be stored at −20 degrees C. in such a buffer for at least a year or more. Preferably, storage for a year or more at −20 degrees C. results in less than a 50% decrease in biological activity. More preferably, storage for a year or more at −20 degrees C. results in less than a 20% decrease in biological activity after a year or more. Most preferably, storage for a year or more at −20 degrees C. results in less than a 10% decrease in biological activity.

In order to ensure stability of the siRNA pools prior to usage, they may be retained in dried-down form at −20 degrees C. until they are ready for use. Prior to usage, they should be resuspended; however, once resuspended, for example, in the aforementioned buffer, they should be kept at −20 degrees C. until used. The aforementioned buffer, prior to use, may be stored at approximately 4 degrees C. or room temperature. Effective temperatures at which to conduct transfection are well known to persons skilled in the art, and include for example, room temperature.

In order to form the duplex siRNA from the component complementary strands, equal quantities of the sense strand and antisense strand are mixed. Since the oligonucleotides retain the 2'-orthoester protection at this point, they are treated with mild acid at 55 degrees C., which treatment removes these protecting groups. The deprotected strands are annealed to form the duplex by allowing the deprotection solution to cool slowly to room temperature. Finally, the duplex is desalted by precipitating it with ethanol, and the purified duplex is dissolved in RNAse-free water and quantified by ultraviolet spectroscopy. The quality of the duplexing process is assessed by native gel electrophoresis.

Applications for this new and novel technology are broad. For instance, it is possible that an individual may identify one or more siRNA directed against, e.g., a therapeutically important target. Said molecule might provide excellent silencing of the target of interest, but simultaneously silence additional genes (off-targets) that have partial complementarity with the sense and/or antisense strand of the siRNA. Silencing of these secondary targets (off-targets) can induce undesirable effects (e.g., cell death, cell proliferation, differentiation) and for this reason, it is advantageous to eliminate the off-target effects associated with the siRNA of interest.

Further, the siRNA of the present invention may be used in a diverse set of applications, including but not limited to basic research, drug discovery and development, diagnostics, and therapeutics. In research settings, the application can involve introduction of modified molecules into cells using either a reverse transfection or forward transfection protocol. For example, the present invention may be used to validate whether a gene product is a target for drug discovery or development. In this application, the mRNA that corresponds to a target nucleic acid sequence of interest is identified for targeted degradation. Inventive siRNAs that are specific for targeting the particular gene are introduced into a cell or organism, preferably in duplex form. The cell or organism is maintained under conditions allowing for the degradation of the targeted mRNA, resulting in decreased activity or expression of the gene. The extent of any decreased expression or activity of the gene is then measured, along with the effect of such decreased expression or activity, and a determination is made that if expression or activity is decreased, then the nucleic acid sequence of interest is an agent for drug discovery or development. In this manner, phenotypically desirable effects can be associated with RNA interference of particular target nucleic acids of interest, and in appropriate cases toxicity and pharmacokinetic studies can be undertaken and therapeutic preparations developed.

The invention can be implemented for a wide range of applications associated with transfection of the modified molecules. In one non-limiting example, modifications of the invention are used to eliminate off-target effects resulting from transfection of siRNA in a reverse transfection format. For example, the modified siRNA are dried on a solid surface (e.g., the bottom of a well in a 96, 384, or 1536 well plate), solubilized by the addition of a carrier (e.g., a lipid transfection reagent), followed by the addition of the cell type(s) of choice for transfection.

In another application of the invention, siRNA that are modified with the modifications of the invention, or unmodified, are separately transfected into cells and run side-by-side to identify or distinguish between gene-knockdown induced phenotypic outcomes that are generated by target specific silencing and off-target silencing.

In another application of using the modified siRNA of the invention, cells are transfected with pools of modified siRNA or modified individual siRNA that constitute the pools. In this way, a user is able to identify the most functional siRNA or combination of siRNAs against an individual target.

In yet another application, siRNA carrying the modifications of the invention are directed against a particular family of genes (e.g., kinases), genes associated with a particular pathway(s) (e.g., cell cycle regulation), or entire genomes (e.g., the human, rat, mouse, *C. elegans*, or *Drosophila* genome). Knockdown of each gene of the collection with siRNA carrying the modifications of the invention would enable researchers to assess quickly the contribution of each member of a family of genes, or each member of a pathway, or each gene in a genome, to a particular biological function or event without the risk that the phenotype is the result of an off-target effect. As one example of this sort of application, individuals who are interested in identifying one or more host (human) genes that contribute to the ability of, e.g., the HIV virus to infect human cells, can plate siRNA directed against the entire human genome in a RTF format. Following lipoplex formation, cells that are susceptible to HIV infection (e.g., JC53 cells) are added to each well for transfection. After culturing the cells for a period of 24-48 hours, the cells in each well could be subjected to a lethal titer of the HIV virus. Following an appropriate incubation period necessary for infection, plates could be examined to identify which wells contain living cells. Wells that contain living cells (or a substantially larger number of living cells than controls) identify a host gene that is necessary for viral infection, replication, and/or release. In this way, one is able to identify host genes that play a role in pathogen infection with the risk that the observed phenotype is the result of off-target effects.

In yet another application, cells transfected with siRNA carrying the modifications of the invention are used to assess a particular gene's (target's) contribution to exclusion of a drug from cells. In one non-limiting example, cells are reverse transfected on RTF plates that contain siRNA(s) directed against all known members of the human genome, siRNA directed against a particular family of genes (e.g., kinases), siRNA directed against genes of a particular pathway (e.g., the ADME-tox pathways). Subsequently, cells are treated with a particular compound (e.g., a potential therapeutic compound) and the ability of cells to, e.g., retain, excrete, metabolize, or adsorb that compound can be measured and compared with untreated cells. In this way, a researcher can identify one or more host genes that play a role in the pharmacokinetics of the compound with limited risk that the observed phenotype is the result of down-regulation of an off-target gene.

In yet another application, cells transfected with siRNA carrying the modifications of the invention are used to validate the target of one or more biologically relevant agents (e.g., a drug). For instance, if a particular drug is believed to target a particular protein and induce a particular phenotype, the action of the drug can be validated by targeting its target protein with a gene-specific siRNA carrying the modifications of the invention. If the siRNA induces the same phenotype as the drug, then the target is validated. If the modified siRNA fails to induce the same phenotype, then these experiments would question the validity of the proposed protein as the drug target.

In yet another application, two or more siRNAs carrying the modifications of the invention and targeting two or more distinct targets can be used to identify and study synthetic lethal pairs.

In yet another application, siRNA carrying the modifications of the invention can be used to target transcripts containing single nucleotide polymorphisms (SNPs) to facilitate and assess the contribution of a particular SNP to a phenotype, a biological function, a disease state, or event.

In yet another application, siRNA carrying the modifications of the invention can be used to target a gene(s) whose knockdown is known to induce a particular disease state. In this way, it is possible to facilitate study of that particular disease without the risk of knocking down the expression of additional genes.

In all of the applications described above, the applications can be employed in such a way as to knock down one or multiple genes in a single well.

The present invention may also be used in RNA interference applications that induce transient or permanent states of disease or disorder in an organism by, for example, attenuating the activity of a target nucleic acid of interest believed to be a cause or factor in the disease or disorder of interest. Increased activity of the target nucleic acid of interest may render the disease or disorder worse, or tend to ameliorate or to cure the disease or disorder of interest, as the case may be. Likewise, decreased activity of the target nucleic acid of interest may cause the disease or disorder, render it worse, or tend to ameliorate or cure it, as the case may be. Target nucleic acids of interest can comprise genomic or chromosomal nucleic acids or extrachromosomal nucleic acids, such as viral nucleic acids.

Still further, the present invention may be used in RNA interference applications, such as diagnostics, prophylactics, and therapeutics including use of the compositions in the manufacture of a medicament in animals, preferably mammals, more preferably humans in the treatment of diseases, or over or under expression of a target. Preferably, the disease or disorder is one that arises from the malfunction of one or more proteins, the disease or disorder of which is related to the expression of the gene product of the one or more proteins. For example, it is widely recognized that certain cancers of the human breast are related to the malfunction of a protein expressed from a gene commonly known as the "bcl-2" gene. A medicament can be manufactured in accordance with the compositions and teachings of the present invention, employing one or more siRNAs directed against the bcl-2 gene, and optionally combined with a pharmaceutically acceptable carrier, diluent and/or adjuvant, which medicament can be used for the treatment of breast cancer. Applicants have established the utility of the methods and compositions in cellular models. Methods of delivery of polynucleotides, such as siRNAs, to cells within animals, including humans, are well known in the art. Any delivery vehicle now known in the art, or that comes to be known, and has utility for introducing polynucleotides, such as siRNAs, to animals, including humans, is expected to be useful in the manufacture of a medicament in accordance with the present invention, so long as the delivery vehicle is not incompatible with any modifications that may be present within a composition made according to the present invention. A delivery vehicle that is not compatible with a composition made according to the present invention is one that reduces the efficacy of the composition by greater than 95% as measured against efficacy in cell culture.

Animal models exist for many, many disorders, including, for example, cancers, diseases of the vascular system, inborn errors or metabolism, and the like. It is within ordinary skill in the art to administer nucleic acids to animals in dosing regimens to arrive at an optimal dosing regimen for particular disease or disorder in an animal such as a mammal, for example, a mouse, rat or non-human primate. Once efficacy is established in the mammal by routine experimentation by one of ordinary skill, dosing regimens for the commencement of human trials can be arrived at based on data arrived at in such studies.

Dosages of medicaments manufactured in accordance with the present invention may vary from micrograms per kilogram to hundreds of milligrams per kilogram of a subject. As is known in the art, dosage will vary according to the mass of the mammal receiving the dose, the nature of the mammal receiving the dose, the severity of the disease or disorder, and the stability of the medicament in the serum of the subject, among other factors well known to persons of ordinary skill in the art.

For these applications, an organism suspected of having a disease or disorder that is amenable to modulation by manipulation of a particular target nucleic acid of interest is treated by administering siRNA. Results of the siRNA treatment may be ameliorative, palliative, prophylactic, and/or diagnostic of a particular disease or disorder. Preferably, the siRNA is administered in a pharmaceutically acceptable manner with a pharmaceutically acceptable carrier or diluent.

Therapeutic applications of the present invention can be performed with a variety of therapeutic compositions and methods of administration. Pharmaceutically acceptable carriers and diluents are known to persons skilled in the art. Methods of administration to cells and organisms are also known to persons skilled in the art. Dosing regimens, for example, are known to depend on the severity and degree of responsiveness of the disease or disorder to be treated, with a course of treatment spanning from days to months, or until the desired effect on the disorder or disease state is achieved. Chronic administration of siRNAs may be required for lasting desired effects with some diseases or disorders. Suitable dosing regimens can be determined by, for example, administering varying amounts of one or more siRNAs in a pharmaceutically acceptable carrier or diluent, by a pharmaceutically acceptable delivery route, and amount of drug accumulated in the body of the recipient organism can be determined at various times following administration. Similarly, the desired effect (for example, degree of suppression of expression of a gene product or gene activity) can be measured at various times following administration of the siRNA, and this data can be correlated with other pharmacokinetic data, such as body or organ accumulation. A person of ordinary skill in the art can determine optimum dosages, dosing regimens, and the like. A person of ordinary skill in the art may employ $EC_{50}$ data from in vivo and in vitro animal models as guides for human studies.

Still further, the present invention may be used in RNA interference applications, such as diagnostics, prophylactics, and therapeutics. For these applications, an organism suspected of having a disease or disorder that is amenable to modulation by manipulation of a particular target nucleic acid of interest is treated by administering siRNA. Results of the siRNA treatment may be ameliorative, palliative, prophylactic, and/or diagnostic of a particular disease or disorder. Preferably, the siRNA is administered in a pharmaceutically acceptable manner with a pharmaceutically acceptable carrier and/or diluent.

Further, the siRNAs can be administered in a cream or ointment topically, an oral preparation such as a capsule or tablet or suspension or solution, and the like. The route of administration may be intravenous, intramuscular, dermal, subdermal, cutaneous, subcutaneous, intranasal, oral, rectal, by eye drops, by tissue implantation of a device that releases the siRNA at an advantageous location, such as near an organ or tissue or cell type harboring a target nucleic acid of interest.

Having described the invention with a degree of particularity, examples will now be provided. These examples are not intended to and should not be construed to limit the scope of the claims in any way. Although the invention may be more readily understood through reference to the following examples, they are provided by way of illustration and are not intended to limit the present invention unless specified.

EXAMPLES

Example 1

Synthesizing siRNAs

Figure 3:
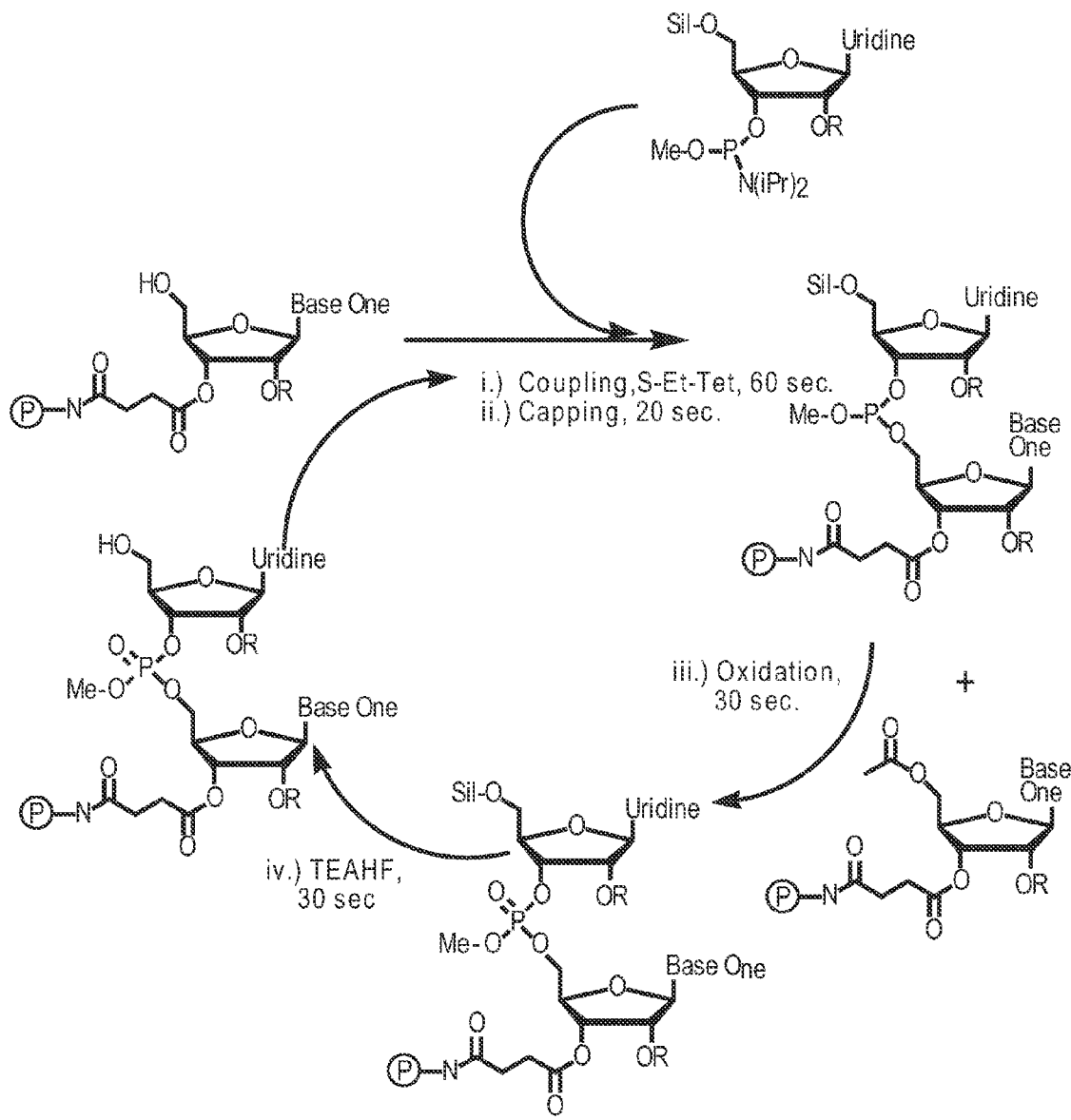
FIG. 3 illustrates an outline of the 2'-ACE RNA synthesis cycle.

RNA oligonucleotides were synthesized using 2'-ACE chemistry (see FIG. 3). The synthesis is preferably carried out as an automated process on an appropriate machine. Several such synthesizing machines are known to those of skill in the art. Each nucleotide is added sequentially (3'-to 5'-direction) to a solid support-bound oligonucleotide. Although polystyrene supports are preferred, any suitable support can be used. The first nucleoside at the 3'-end of the chain is covalently attached to a solid support. The nucleotide precursor, an activated ribonucleotide such as a phosphoramidite or H-phosphonate, and an activator such as a tetrazole, for example, S-ethyl-tetrazole (although any other suitable activator can be used) are added (step i in FIG. 3), coupling the second base onto the 5'-end of the first nucleoside. The support is washed and any unreacted 5'-hydroxyl groups are capped with an acetylating reagent such as, but not limited to, acetic anhydride or phenoxyacetic anhydride to yield unreactive 5'-acetyl moieties (step ii). The P(III) linkage is then oxidized to the more stable and ultimately desired P(V) linkage (step iii), using a suitable oxidizing agent such as, for example, t-butyl hydroperoxide or iodine and water. At the end of the nucleotide addition cycle, the 5'-silyl group is cleaved with fluoride ion (step iv), for example, using triethylammonium fluoride or t-butyl ammonium fluoride. The cycle is repeated for each subsequent nucleotide. It should be emphasized that although FIG. 3 illustrates a phosphoramidite having a methyl protecting group, any other suitable group may be used to protect or replace the oxygen of the phosphoramidite moiety. For example, alkyl groups, cyanoethyl groups, or thio derivatives can be employed at this position. Further, the incoming activated nucleoside in step (i) can be a different kind of activated nucleoside, for example, an H-phosphonate, methyl phosphonamidite or a thiophosphoramidite. It should be noted that the initial, or 3', nucleoside attached to the support can have a different 5' protecting group such as a dimethoxytrityl group, rather than a silyl group. Cleavage of the dimethoxytrityl group requires acid hydrolysis, as employed in standard DNA synthesis chemistry. Thus, an acid such as dichloroacetic acid (DCA) or trichloroacetic acid (TCA) is employed for this step alone. Apart from the DCA cleavage step, the cycle is repeated as many times as necessary to synthesize the polynucleotide desired.

Following synthesis, the protecting groups on the phosphates, which are depicted as methyl groups in FIG. 3, but need not be limited to methyl groups, are cleaved in 30 minutes utilizing 1 M disodium-2-carbamoyl-2-cyanoethylene-1,1-dithiolate trihydrate (dithiolate) in DMF (dimethylformamide). The deprotection solution is washed from the solid support bound oligonucleotide using water. The support is then treated with 40% methylamine for 20 minutes at 55 degree C. This releases the RNA oligonucleotides into solution, deprotects the exocyclic amines and removes the acetyl protection on the 2'-ACE groups. The oligonucleotides can be analyzed by anion exchange HPLC at this stage.

Figure 4:
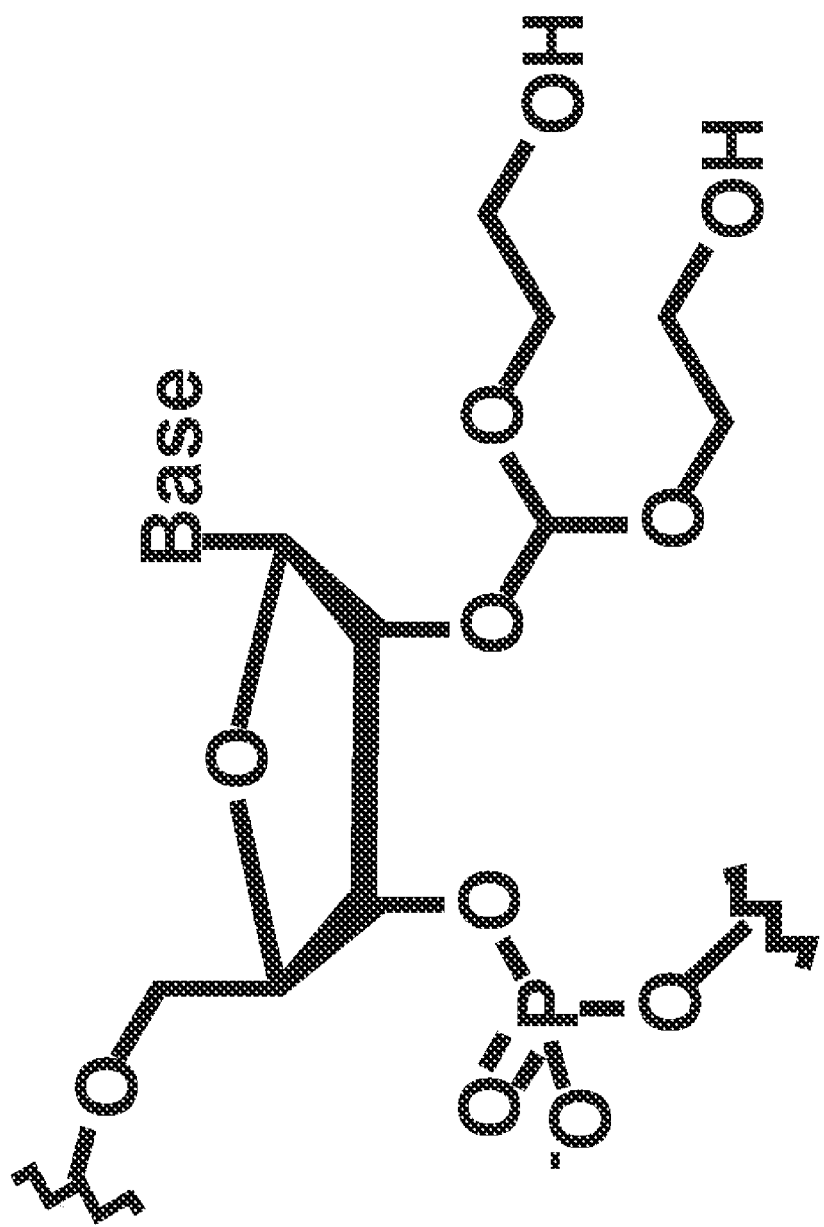
FIG. 4 illustrates the structure of a preferred 2'-ACE protected RNA immediately prior to 2'-deprotection.

The 2'-orthoester groups are the last protecting groups to be removed, if removal is desired. The structure of the 2'-ACE protected RNA immediately prior to 2'-deprotection is as represented in FIG. 4.

For automated procedures, solid supports having the initial nucleoside are installed in the synthesizing instrument. The instrument will contain all the necessary ancillary reagents and monomers needed for synthesis. Reagents are maintained under argon, since some monomers, if not maintained under an inert gas, can hydrolyze. The instrument is primed so as to fill all lines with reagent. A synthesis cycle is designed that defines the delivery of the reagents in the proper order according to the synthesis cycle, delivering reagents in a specified order. Once a cycle is defined, the amount of each reagent to be added is defined, the time between steps is defined, and washing steps are defined, synthesis is ready to proceed once the solid support having the initial nucleoside is added.

For the RNA analogs described herein, modification is achieved through three different general methods. The first, which is implemented for carbohydrate and base modifications, as well as for introduction of certain linkers and conjugates, employs modified phosphoramidites in which the modification is pre-existing. An example of such a modification would be the carbohydrate 2'-modified species (2'-F, 2'-NH$_2$, 2'-O-alkyl, etc.) wherein the 2' orthoester is replaced with the desired modification 3' or 5' terminal modifications could also be introduced such as fluoroscein derivatives, Dabsyl, cholesterol, cyanine derivatives or polyethylene glycol. Certain inter-nucleotide bond modifications would also be introduced via the incoming reactive nucleoside intermediate. Examples of the resultant internucleotide bond modification include but are not limited to methylphosphonates, phosphoramidates, phosphorothioates or phoshorodithioates.

Many modifiers can be employed using the same or similar cycles. Examples in this class would include, for example, 2-aminopurine, 5-methyl cytidine, 5-aminoallyl uridine, diaminopurine, 2-O-alkyl, multi-atom spacers, single monomer spacers, 2'-aminonucleosides, 2'-fluoro nucleosides, 5-iodouridine, 4-thiouridine, acridines, 5-bromouridine, 5-fluorocytidine, 5-fluorouridine, 5-iodouridine, 5-iodocytidine, 5-biotin-thymidine, 5-fluoroscein-thymidine, inosine, pseudouridine, abasic monomer, nebularane, deazanucleoside, pyrene nucleoside, azanucleoside, etc. Often the rest of the steps in the synthesis would remain the same with the exception of modifications that introduce substituents that are labile to standard deprotection conditions. Here modified conditions would be employed that do not affect the substituent. Second, certain internucleotide bond modifications require an alteration of the oxidation step to allow for their introduction. Examples in this class include phosphorothioates and phosphorodithioates wherein oxidation with elemental sulfur or another suitable sulfur transfer agent is required. Third, certain conjugates and modifications are introduced by "post-synthesis" process, wherein the desired molecule is added to the biopolymer after solid phase synthesis is complete. An example of this would be the addition of polyethylene glycol to a pre-synthesized oligonucleotide that contains a primary amine attached to a hydrocarbon linker. Attachment in this case can be achieved by using a N-hydroxy-succinimidyl ester of polyethylene glycol in a solution phase reaction.

While this outlines the most preferred method for synthesis of synthetic RNA and its analogs, any nucleic acid synthesis method that is capable of assembling these molecules could be employed in their assembly. Examples of alternative methods include 5'-DMT-2'-TBDMS and 5'-DMT-2'-TOM synthesis approaches. Some 2'-O-methyl, 2'-F and backbone modifications can be introduced in transcription reactions using modified and wild type T7 and SP6 polymerases, for example.

Synthesizing Modified RNA

The following guidelines are provided for synthesis of modified RNAs, and can readily be adapted to use on any of the automated synthesizers known in the art. A 3' Terminal Modifications There are several methods for incorporating 3' modifications. The 3' modification can be anchored or "loaded" onto a solid support of choice using methods known in the art. Alternatively, the 3' modification may be available as a phosphoramidite. The phosphoramidite is coupled to a universal support using standard synthesis methods where the universal support provides a hydroxyl at which the 3' terminal modification is created by introduction of the activated phosphoramidite of the desired terminal modification. According to another method, the 3' modification could be introduced post synthetically after the polynucleotide is removed from the solid support. The free polynucleotide initially has a 3' terminal hydroxyl, amino, thiol, or halogen that reacts with an appropriately activated form of the modification of choice. Examples include but are not limited to N-hydroxy succinimidyl ester, thioether, disulfide, maliemido, or haloalkyl reactions. This modification now becomes the 3' terminus of the polynucleotide. Examples of modifications that can be conjugated post synthetically can be but are not limited to fluorosceins, acridines, TAMRA, dabsyl, cholesterol, polyethylene glycols, multi-atom spacers, cyanines, lipids, carbohydrates, fatty acids, steroids, peptides, or polypeptides.

5' Terminal Modifications

There are a number of ways to introduce a 5' modification into a polynucleotide. For example, a nucleoside having the 5' modification can be purchased and subsequently activated to a phosphoramidite, or the phosphoramidite having the 5' modification may be commercially available. Then, the activated nucleoside having the 5' modification is employed in the cycle just as any other activated nucleoside may be used. However, not all 5' modifications are available as phosphoramidites. In such an event, the 5' modification can be introduced in an analogous way to that described for 3' modifications above.

Thioates

Polynucleotides having one or more thioate moieties, such as phosphorothioate linkages, were made in accordance with the synthesis cycle described above and illustrated in FIG. 3. However, in place of the t-butyl hydroperoxide oxidation step, elemental sulfur or another sulfurizing agent was used.

5'-Thio Modifications

Monomers having 5' thiols can be purchased as phosphoramidites from commercial suppliers such as Glen Research. These 5' thiol modified monomers generally bear trityl protecting groups. Following synthesis, the trityl group can be removed by any method known in the art.

Other Modifications

For certain modifications, the steps of the synthesis cycle will vary somewhat. For example, where the 3' end has an inverse dT (wherein the first base is attached to the solid support through the 5'-hydroxyl and the first coupling is a 3'-3' linkage) detritylation and coupling occurs more slowly, so extra detritylating reagent, such as dichloroacetic acid (DCA), should be used and coupling time should be increased to 300 seconds. Some 5' modifications may require extended coupling time. Examples include cholesterol, fluorophores such as Cy3 or Cy5 biotin, dabsyl, amino linkers, thio linkers, spacers, polyethylene glycol, phosphorylating reagent, BODIPY, or photocleavable linkers.

It should be noted that if a polynucleotide is to have only a single modification, that modification can be most efficiently carried out manually by removing the support having the partially built polynucleotide on it, manually coupling the monomer having the modification, and then replacing the support in the automated synthesizer and resuming automated synthesis.

Example 2

Deprotection and Cleavage of Synthesized Oligos from the Support

Cleaving can be done manually or in an automated process on a machine. Cleaving of the protecting moiety from the internucleotide linkage, for example a methyl group, can be achieved by using any suitable cleaving agent known in the art, for example, dithiolate or thiophenol. One molar dithiolate in DMF is added to the solid support at room temperature for 10 to 20 minutes. The support is then thoroughly washed with, for example, DMF, then water, then acetonitrile. Alternatively a water wash followed by a thorough acetonitrile will suffice to remove any residual dithioate.

Cleavage of the polynucleotide from the support and removal of exocyclic base protection can be done with 40% aqueous N-methylamine (NMA), followed by heating to 55 degrees Centigrade for twenty minutes. Once the polynucleotide is in solution, the NMA is carefully removed from the solid support. The solution containing the polynucleotide is then dried down to remove the NMA under vacuum. Further processing, including duplexing, desalting, gel purifying, quality control, and the like can be carried out by any method known in the art.

For some modifications, the NMA step may vary. For example, for a 3' amino modification, the treatment with NMA should be for forty minutes at 55 degrees Centigrade. Puromycin, 5' terminal amino linker modifications, and 2' amino nucleoside modifications are heated for 1 hour after addition of 40% NMA. Oligonucleotides modified with Cy5 are treated with ammonium hydroxide for 24 hours while protected from light.

Preparation of Cleave Reagents

HPLC grade water and synthesis grade acetonitrile are used. The dithiolate is pre-prepared as crystals. Add 4.5 grams of dithiolate crystals to 90 mL of DMF. Forty percent NMA can be purchased, ready to use, from a supplier such as Sigma Aldrich Corporation.

Annealing Single Stranded Polynucleotides

Single stranded polynucleotides can be annealed by any method known in the art, employing any suitable buffer. For example, equal amounts of each strand can be mixed in a suitable buffer, such as, for example, 50 mM HEPES pH 7.5, 100 mM potassium chloride, 1 mM magnesium chloride. The mixture is heated for one minute at 90 degrees Centigrade, and allowed to cool to room temperature. In another example, each polynucleotide is separately prepared such that each is at 50 micromolar concentration. Thirty microliters of each polynucleotide solution is then added to a tube with 15 microliters of 5× annealing buffer, wherein the annealing buffer final concentration is 100 mM potassium chloride, 30 mM HEPES-KOH pH 7.4 and 2 mM magnesium chloride. Final volume is 75 microliters. The solution is then incubated for one minute at 90 degrees Centigrade, spun in a centrifuge for 15 seconds, and allowed to incubate at 37 degrees Centigrade for one hour, then allowed to come to room temperature. This solution can then be stored frozen at minus 20 degrees Centigrade and freeze thawed up to five times. The final concentration of the duplex is 20 micromolar. An example of a buffer suitable for storage of the polynucleotides is 20 mM KCl, 6 mM HEPES pH 7.5, 0.2 mM MgCl$_2$. All buffers used should be RNase free.

Removal of the Orthoester Moiety

If desired, the orthoester moiety or moieties may be removed from the polynucleotide by any suitable method known in the art. One such method employs a volatile acetic acid-tetramethylenediamine (TEMED) pH 3.8 buffer system that can be removed by lyophilization following removal of the orthoester moiety or moieties. Deprotection at a pH higher than 3.0 helps minimize the potential for acid-catalyzed cleavage of the phosphodiester backbone. For example, deprotection can be achieved using 100 mM acetic acid adjusted to pH 3.8 with TEMED by suspending the orthoester protected polynucleotide and incubating it for 30 minutes at 60 degrees Centigrade. The solution is then lyophilized or subjected to a SpeedVac to dryness prior to use. If necessary, desalting following deprotection can be performed by any method known in the art, for example, ethanol precipitation or desalting on a reversed phase cartridge.

Example 3 siRNAs Synthesized for Use in RNA Interference

Nineteen-mer siRNAs having a di-dT overhang were synthesized using Dharmacon, Inc.'s proprietary ACE chemistry, and were designed and used in accordance with the invention described herein. "SEAP" refers to human secreted alkaline phosphatase; "human cyclo" refers to human cyclophilin B; an asterisk between nucleotide units refers to a modified internucleotide linkage that is a phosphorothioate linkage; the structure 2'-F—C or 2'-F—U refers to a nucleotide unit having a fluorine atom attached to the 2' carbon of a ribosyl moiety; the structure 2'-N—C or 2'-N—U refers to a nucleotide unit having an —NH$_2$ group attached to the 2' carbon of a ribosyl moiety; the structure 2'-OME-C or 2'-OME-U refers to a nucleotide unit having a 2'-O-methyl modification at the 2' carbon of a ribosyl moiety of either Cs or Us, respectively; dG, dU, dA, dC, and dT refer to a nucleotide unit that is deoxy with respect to the 2' position, and instead has a hydrogen attached to the 2' carbon of the ribosyl moiety. Unless otherwise indicated, all nucleotide units in the list below are ribosyl with an —OH at the 2' carbon.

Synthesis of siRNA Duplex of General Formula I

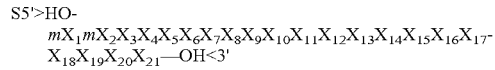

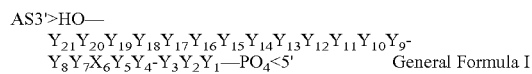

General Formula I where $X_q$ and $Y_q$ are ribonucleosides including rA, rC, rG, or rU;

$mX_q$ are 2'-O-methyl nucleosides including 2'-O-methyl-rA, 2'-O-methyl-rC, 2'-O-methyl-rG, and 2'-O-methyl-rU;

S is the sense strand of the siRNA duplex;

and AS is the antisense strand of the siRNA duplex.

Each strand (S and AS) of the duplex is separately chemically synthesized using the procedures described in U.S. Pat. Nos. 6,008,400; 6,111,086; 6,590,093; Scaringe (2000)*Methods in Enzymology* 317:3-18; Scaringe (2001) *Methods* 23(3):206-217. Briefly, the procedures utilize a solid polystyrene support to which the 3'-most nucleoside ($X_{21}$ or $Y_{21}$) has been covalently tethered. Nucleosides are then added sequentially in a sequence-specific manner (3' to 5') to the support-bound species using repetitive cycles. Thus, the first cycle adds $X_{20}$ to $X_{21}$ or $Y_{20}$ to $Y_{21}$; the second cycle adds $X_{19}$ to $X_{20}X_{21}$ or $Y_{19}$ to $Y_{20}Y_{21}$; and so on. Each cycle consists of four steps: deprotection of the 5'-hydroxyl group of the support-bound species; coupling of a reactive derivative of the incoming nucleoside to the 5'-hydroxyl group of support-bound species; capping of unreacted 5'-hydroxyl groups; and oxidation of the internucleotide linkage. For $X_q$ (q=3 to 20) or $Y_q$ (q=1 to 20)=a ribonucleoside, the reactive derivative is a 5'-silyl-2'-orthoester-3'-phosphoramidite, in particular, a 5'-O-benzhydroxy-bis(trimethylsilyloxy)silyl-2'-O-bis(2-acetoxyethyl)orthoformyl-3'-O—(N,N-diisopropyl)methyl phosphoramidite (FIG. 15).

Duplexes of General Formula I have 2'-O-methyl nucleosides in positions 1 and 2 (mXq, q=1 and 2) of the sense strand. These modified nucleosides are incorporated into S using the sequence-appropriate 5'-silyl-2'-O-methyl-3'-phosphoramidites, in particular, 5'-O-benzhydroxy-bis(trimethylsilyloxy)-silyl-2'-O-methyl-3'-O-(N,N-diisopropyl)methyl phosphoramidites (FIG. 16), and the same reaction cycle utilized for ribonucleoside incorporation described above.

Duplexes of General Formula I have a phosphate moiety on the 5'-terminus of the antisense strand. This phosphate group is introduced chemically using N,N-diisopropylamino-bis(2-cyanoethyl) phosphoramidite (FIG. 17) and the same reaction cycle utilized for ribonucleoside incorporation described above.

Following chain assembly, the fully protected oligonucleotide is treated with disodium-2-carbamoyl-2-cyanoethylene-1,1-dithiolate trihydrate to remove the methyl groups from the internucleotide phosphate linkages. The oligonucleotide is then cleaved from the support and the base protecting groups and the 2-cyanoethyl groups on the 5'-phosphate are removed by treatment with aqueous N-methylamine, first at room temperature and then at 55 degrees C., followed by drying under vacuum. At this point, the crude oligonucleotide is analyzed for quality by ion exchange HPLC and/or MALDI-TOF mass spectrometry, and gel purified if necessary. The oligonucleotide is then dissolved in RNAse-free water or buffer and quantified using ultraviolet spectroscopy.

In order to form the duplex siRNA from the component complementary strands, equal quantities of the sense strand and antisense strand are mixed. Since the oligonucleotides retain the 2'-orhtoester protection at this point, they are treated with mild acid at 55 degrees C., which treatment removes these protecting groups. The deprotected strands are annealed to form the duplex by allowing the deprotection solution to cool slowly to room temperature. Finally, the duplex is desalted by precipitating it with ethanol, and the purified duplex is dissolved in RNAse-free water and quantified by ultraviolet spectroscopy. The quality of the duplexing process is assessed by native gel electrophoresis.

Synthesis of siRNA Duplex of General Formula II

S5'>HO-
$mX_1mX_2X_3X_4X_5X_6X_7X_8X_9X_{10}X_{11}X_{12}X_{13}X_{14}X_{15}$-
$X_{16}X_{17}X_{18}X_{19}X_{20}X_{21}$—OH<3'

AS3'>HO—
$Y_{21}Y_{20}Y_{19}Y_{18}Y_{17}Y_{16}Y_{15}Y_{14}Y_{13}Y_{12}Y_{11}$-
$Y_{10}Y_9Y_8Y_7Y_6Y_5Y_4Y_3mY_2mY_1$—PO$_4$<5'    General Formula II where $X_q$ and $Y_q$ are ribonucleosides including rA, rC, rG, or rU;

mXq and mYq are 2'-O-methyl nucleosides including 2'-O-methyl-rA, 2'-O-methyl-rC, 2'-O-methyl-rG, and 2'-O-methyl-rU;

S is the sense strand of the siRNA duplex; and AS is the antisense strand of the siRNA duplex.

Each strand (S and AS) of the duplex is separately chemically synthesized using the procedures described in U.S. Pat. Nos. 6,008,400; 6,111,086; 6,590,093; Scaringe (2000) Methods in Enzymology 317:3-18; Scaringe (2001) Methods 23(3):206-217. Briefly, the procedures utilize a solid polystyrene support to which the 3'-most nucleoside (X21 or Y21) has been covalently tethered. Nucleosides are then added sequentially in a sequence-specific manner (3' to 5') to the support-bound species using repetitive cycles. Thus, the first cycle adds X20 to X21 or Y20 to Y21; the second cycle adds X19 to X20X21 or Y19 to Y20Y21; and so on. Each cycle consists of four steps: deprotection of the 5'-hydroxyl group of the support-bound species; coupling of a reactive derivative of the incoming nucleoside to the 5'-hydroxyl group of support-bound species; capping of unreacted 5'-hydroxyl groups; and oxidation of the internucleotide linkage. For Xq (q=3 to 20) or Yq (q=3 to 20)=a ribonucleoside, the reactive derivative is a 5'-silyl-2'-orthoester-3'-phosphoramidite, in particular, a 5'-O-benzhydroxy-bis(trimethylsilyloxy)silyl-2'-O-bis(2-acetoxyethyl)orth-oformyl-3'-O—(N,N-diisopropyl)methyl phosphoramidite (FIG. 15).

Duplexes of General Formula II have 2'-O-methyl nucleosides in positions 1 and 2 (mXq, q=1 and 2) of the sense strand and in positions 1 and 2 (mYq, q=1 and 2) of the antisense strand. These modified nucleosides are incorporated into S and AS using the sequence-appropriate 5'-silyl-2'-O-methyl-3'-phosphoramidites, in particular, 5'-O-benzhydroxy-bis(trimethylsilyloxy)-silyl-2'-O-methyl-3'-O- (N,N-diisopropyl)methyl phosphoramidites (FIG. 16), and the same reaction cycle utilized for ribonucleoside incorporation described above.

Duplexes of General Formula II have a phosphate moiety on the 5'-terminus of the antisense strand. This phosphate group is introduced chemically using N,N-diisopropylamino-bis(2-cyanoethyl) phosphoramidite (FIG. 17) and the same reaction cycle utilized for ribonucleoside incorporation described above.

Following chain assembly, the fully protected oligonucleotide is treated with disodium-2-carbamoyl-2-cyanoethylene-1,1-dithiolate trihydrate to remove the methyl groups from the internucleotide phosphate linkages. The oligonucleotide is then cleaved from the support and the base protecting groups and the 2-cyanoethyl groups on the 5'-phosphate are removed by treatment with aqueous N-methylamine, first at room temperature and then at 55 degree C., followed by drying under vacuum. At this point, the crude oligonucleotide is analyzed for quality by ion exchange HPLC and/or MALDI-TOF mass spectrometry, and gel purified if necessary. The oligonucleotide is then dissolved in RNAse-free water or buffer and quantified using ultraviolet spectroscopy.

In order to form the duplex siRNA from the component complementary strands, equal quantities of the sense strand and antisense strand are mixed. Since the oligonucleotides retain the 2'-orhtoester protection at this point, they are treated with mild acid at 55 degree C., which treatment removes these protecting groups. The deprotected strands are annealed to form the duplex by allowing the deprotection solution to cool slowly to room temperature. Finally, the duplex is desalted by precipitating it with ethanol, and the purified duplex is dissolved in RNAse-free water and quantified by ultraviolet spectroscopy. The quality of the duplexing process is assessed by native gel electrophoresis.

Synthesis of siRNA Duplex of General Formula III

S5'>HO-
$mX_1mX_2X_3X_4X_5X_6X_7X_8X_9X_{10}X_{11}X_{12}X_{13}X_{14}X_{15}X_{16}$-
$X_{17}X_{18}X_{19}X_{20}X_{21}$—OH<3'

AS3'>HO—
$Y_{21}Y_{20}Y_{19}Y_{18}Y_{17}Y_{16}Y_{15}Y_{14}Y_{13}Y_{12}Y_{11}Y_{10}$-
$Y_9Y_8Y_7Y_6Y_5Y_4Y_3mY_2mY_1$—PO$_4$<5'    General Formula III where Xq and Yq are ribonucleosides including rA, rC, rG or rU;

mXq and mYq are 2'-O-methyl nucleosides including 2'-O-methyl-rA, 2'-O-methyl-rc, 2'-O-methyl-rG, and 2'-O-methyl-rU;

S is the sense strand of the siRNA duplex;

and AS is the antisense strand of the siRNA duplex.

Each strand (S and AS) of the duplex is separately chemically synthesized using the procedures described in U.S. Pat. Nos. 6,008,400; 6,111,086; 6,590,093; Scaringe (2000) Methods in Enzymology 317:3-18; Scaringe (2001) Methods 23(3):206-217. Briefly, the procedures utilize a solid polystyrene support to which the 3'-most nucleoside (X21 or Y21) has been covalently tethered. Nucleosides are then added sequentially in a sequence-specific manner (3' to 5') to the support-bound species using repetitive cycles. Thus, the first cycle adds X20 to X21 or Y20 to Y21; the second cycle adds X19 to X20X21 or Y19 to Y20Y21; and so on. Each cycle consists of four steps: deprotection of the 5'-hydroxyl group of the support-bound species; coupling of a reactive derivative of the incoming nucleoside to the 5'-hydroxyl group of support-bound species; capping of unreacted 5'-hydroxyl groups; and oxidation of the internucleotide linkage. For Xq (q=3 to 20) or Yq (q=1 or 3 to 20)=a ribonucleoside, the reactive derivative is a 5'-silyl-2'-orthoester-3'-phosphoramidite, in particular, a 5'-O-benzhydroxy-bis(trimethylsilyloxy)silyl-2'-O-bis(2-acetoxyethyl)orth-oformyl-3'-O—(N,N-diisopropyl)methyl phosphoramidite (FIG. 15).

Duplexes of General Formula III have 2'-O-methyl nucleosides in positions 1 and 2 (mXq, q=1 and 2) of the sense strand and in position 2 (mYq, q=2) of the antisense strand. These modified nucleosides are incorporated into S and AS using the sequence-appropriate 5'-silyl-2'-O-methyl-3'-phosphoramidites, in particular, 5'-O-benzhydroxy-bis(trimethylsilyloxy)-silyl-2'-O-methyl-3'-O—(N,N-diiso-propyl)methyl phosphoramidites (FIG. 16), and the same reaction cycle utilized for ribonucleoside incorporation described above.

Duplexes of General Formula III have a phosphate moiety on the 5'-terminus of the antisense strand. This phosphate group is introduced chemically using N,N-diisopropylamino-bis(2-cyanoethyl) phosphoramidite (FIG. 17) and the same reaction cycle utilized for ribonucleoside incorporation described above.

Following chain assembly, the fully protected oligonucleotide is treated with disodium-2-carbamoyl-2-cyanoethylene-1,1-dithiolate trihydrate to remove the methyl groups from the internucleotide phosphate linkages. The oligonucleotide is then cleaved from the support and the base protecting groups and the 2-cyanoethyl groups on the 5'-phosphate are removed by treatment with aqueous N-methylamine, first at room temperature and then at 55 degrees C., followed by drying under vacuum. At this point, the crude oligonucleotide is analyzed for quality by ion exchange HPLC and/or MALDI-TOF mass spectrometry, and gel purified if necessary. The oligonucleotide is then dissolved in RNAse-free water or buffer and quantified using ultraviolet spectroscopy.

In order to form the duplex siRNA from the component complementary strands, equal quantities of the sense strand and antisense strand are mixed. Since the oligonucleotides retain the 2'-orthoester protection at this point, they are treated with mild acid at 55 degrees C., which treatment removes these protecting groups. The deprotected strands are annealed to form the duplex by allowing the deprotection solution to cool slowly to room temperature. Finally, the duplex is desalted by precipitating it with ethanol, and the purified duplex is dissolved in RNAse-free water and quantified by ultraviolet spectroscopy. The quality of the duplexing process is assessed by native gel electrophoresis.

Transfection siRNA duplexes were annealed using standard buffer (50 millimolar HEPES pH 7.5, 100 millimolar KCl, 1 mM $MgCl_2$). The transfections are done according to the standard protocol described below.

Standard Transfection Protocol for 96 Well and 6 Well Plates: siRNAs

1. Protocols for 293 and Calu6, HeLa, MDA 75 are identical.

2. Cell are plated to be 95% confluent on the day of transfection.

3. SuperRNAsin (Ambion) is added to transfection mixture for protection against RNAses.

4. All solutions and handling have to be carried out in RNAse free conditions.

Plate 1 0.5-1 ml in 25 ml of media in a small flask or 1 ml in 50 ml in a big flask.

96 Well Plate

1. Add 3 ml of 0.05% trypsin-EDTA in a medium flask (6 in a large flask) incubate 5 min at 37 degrees C.

2. Add 7 ml (14 ml big) of regular media and pipet 10 times back and forth to re-suspend cells.

3. Take 25 microliters of the cell suspension from step 2 and 75 microliters of trypan blue stain (1:4) and place 10 microliters in a cell counter.

4. Count number of cells in a standard hemocytometer.

5. Average number of cells×4×10000 is number of cells per ml.

6. Dilute with regular media to have 350 000/ml.

7. Plate 100 microliters (35,000 cell for HEK293) in a 96 well plate.

Transfection for 2×96 Well Plates (60 Well Format)

1. OPTI-MEM 2 ml+80 microliters Lipofectamine 2000 (1:25)+15 microliters of SuperRNAsin (AMBION).

2. Transfer siRNA aliquots (0.8 microliters of 100 micromolar to screen (total dilution factor is 1:750, 0.8 microliters of 100 micromolar solution will give 100 nanomolar final) to the deepdish in a desired order (usually 3 columns×6 for 60 well format or four columns by 8 for 96 well).

3. Transfer 100 microliters of OPTI-MEM.

4. Transfer 100 microliters of OPTI-MEM with Lipofectamine 2000 and SuperRNAsin to each well.

5. Leave for 20-30 min RT.

6. Add 0.55 ml of regular media to each well. Cover plate with film and mix.

7. Array out 100×3×2 directly to the cells (sufficient for two plates).

Transfection for 2×6 Well Plates 8. 8 ml OPTI-MEM+160 microliters Lipofectamine 2000 (1:25). 30 microliters of SuperRNAsin (AMBION).

9. Transfer siRNA aliquots (total dilution factor is 1:750, 5 microliters of 100 micromolar solution will give 100 nanomolar final) to polystyrene tubes.

10. Transfer 1,300 microliters of OPTI-MEM with Lipofectamine 2000 and SuperRNAsin (AMBION).

11. Leave for 20-30 min RT.

12. Add 0.55 ml of regular media to each well. Cover plate with film and mix.

13. Transfer 2 ml to each well (sufficient for two wells).

The mRNA or protein levels are measured 24, 48, 72, and 96 hours post transfection with standard kits or Custom B-DNA sets and Quantigene kits (Bayer).

Example 5

Measurement of Activity/Detection

The level of siRNA-induced RNA interference, or gene silencing, was estimated by assaying the reduction in target mRNA levels or reduction in the corresponding protein levels. Assays of mRNA levels were carried out using B-DNA™ technology (Quantagene Corp.). Protein levels for FLUC and rLUC were assayed by STEADY GLO™ kits (Promega Corp.). Human alkaline phosphatase levels were assayed by Great EscAPe SEAP Fluorescence Detection Kits (#K2043-1), BD Biosciences, Clontech.

For microarray analysis: HeLa cells were transfected in 6-well plates using Oligofectamine (Invitrogen) and the indicated doses of siRNA duplex. Where not specified, the concentration of siRNA was 100 nM. RNA was isolated 24 hours following transfection. RNA from siRNA-transfected cells was hybridized against RNA from mock-transfected cells (treated with transfection reagent in the absence of RNA duplex). Total RNA was purified by Qiagen RNeasy kit, and processed for hybridization to microarrays containing oligonucleotides corresponding to approximately 21,000 human genes. Ratio hybridizations were performed with fluorescent label reversal to eliminate dye bias. Microarrays were either purchased from Agilent Technologies or synthesized as described in Hughes, T. R., et al. (2001) Expression profiling using microarrays fabricated by an ink-jet oligonucleotide synthesizer. Nat. Biotech. 19: 342-347. Each row represents the expression pattern resulting from transfection of an individual siRNA. Microarray data is presented in FIGS. 7-11. Data shown are signature genes that display a difference in expression level (p value<0.01 and log 10 intensity>−1.5) relative to mock-transfected cells. No cuts were placed on fold change in expression. Green indicates decreased expression; red indicates increased expression. Data were analyzed using Rosetta Resolver™ software. The histogram at the top of cluster diagrams reflects the similarity of gene expression changes between different genes analyzed in the experiment.

Example 6

Identification of Chemical Modifications that Modify Silencing Activity

Figure 5A:
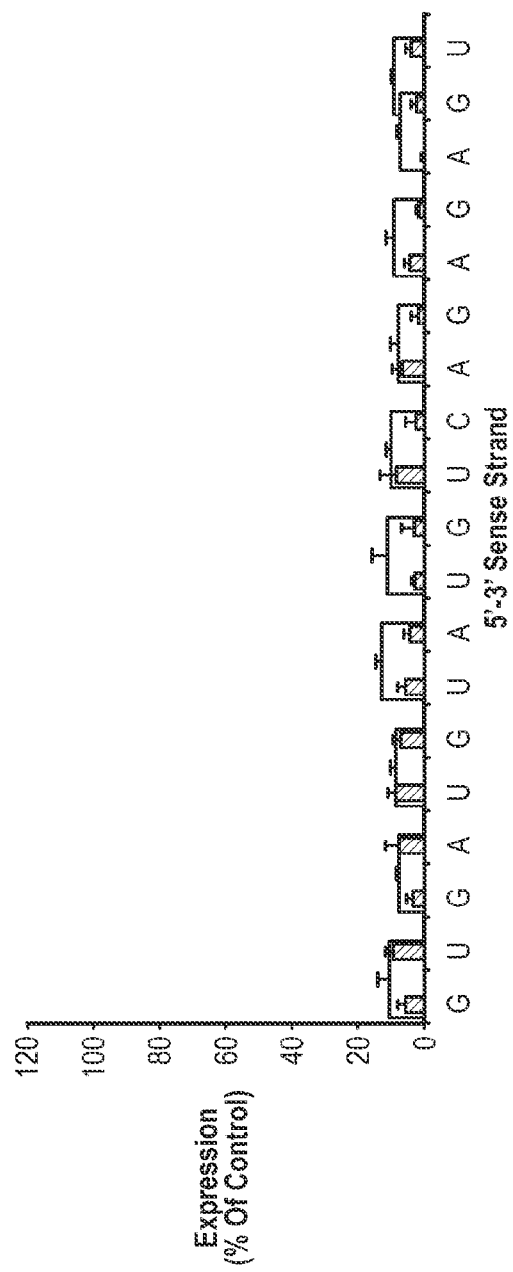
FIGS. 5A and 5B depict the relationship between modification and function for 2'-O-methylated SEAP-2217 siRNA. The figures demonstrate the effect on gene silencing of single base (black bars) and paired (gray) 2'-O-methyl modifications of the sense strand (FIG. 5A) and antisense strand (FIG. 5B) of SEAP-2217. The X-axis represents the relative position of the modification along each siRNA strand (5'->3'). The Y-axis represents the percent expression relative to controls.
Figure 5B:
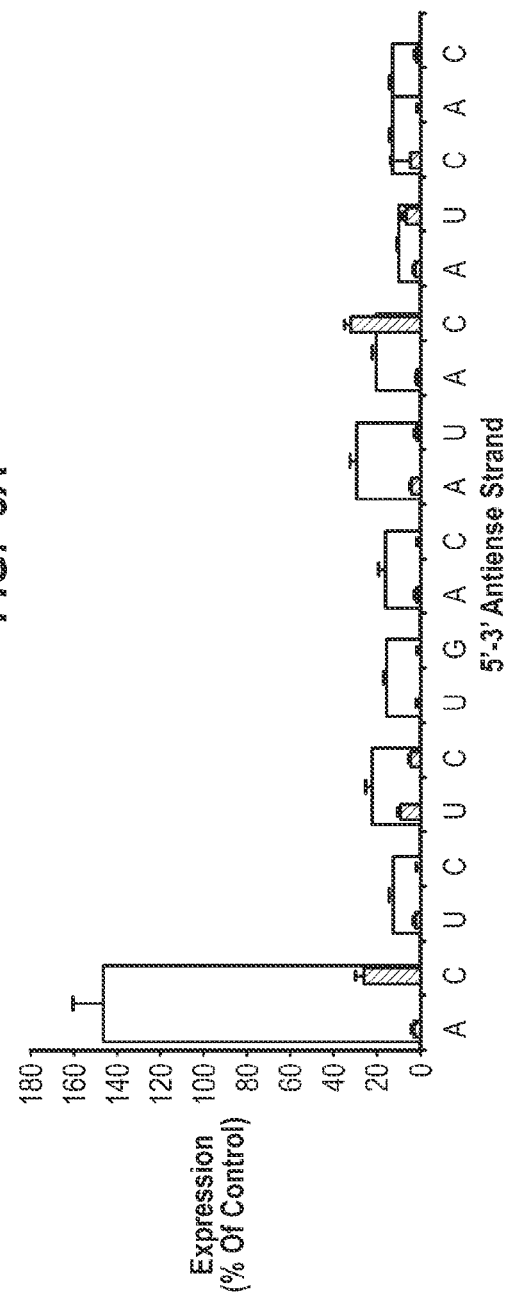
Figure 6A:
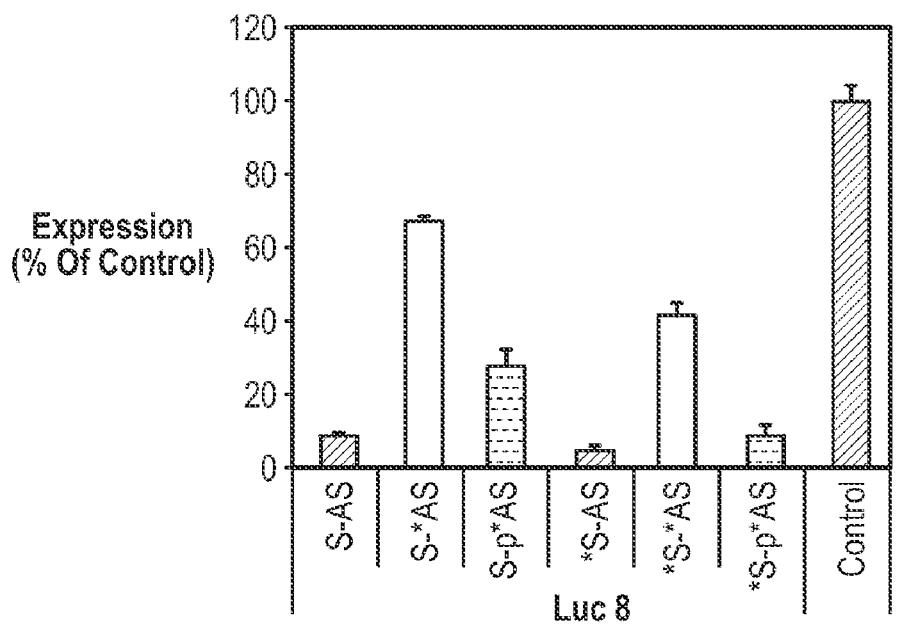
FIGS. 6A-6F show the effects of 2'-O-methylation with and without 5' phosphorylation on the antisense strands of six different luciferase-specific siRNA (luc 8, 18, 56, 58, 63, and 81). "S"=sense strand. "AS"=antisense strand. "*" indicates 2'-O-methylation at positions 1 and 2 of the designated strand. "p" indicates 5' phosphorylation of the designated strand. The Y-axis represents the % expression compared to control (untransfected) cells. "Control"=mock transfected cells.
Figure 6B:
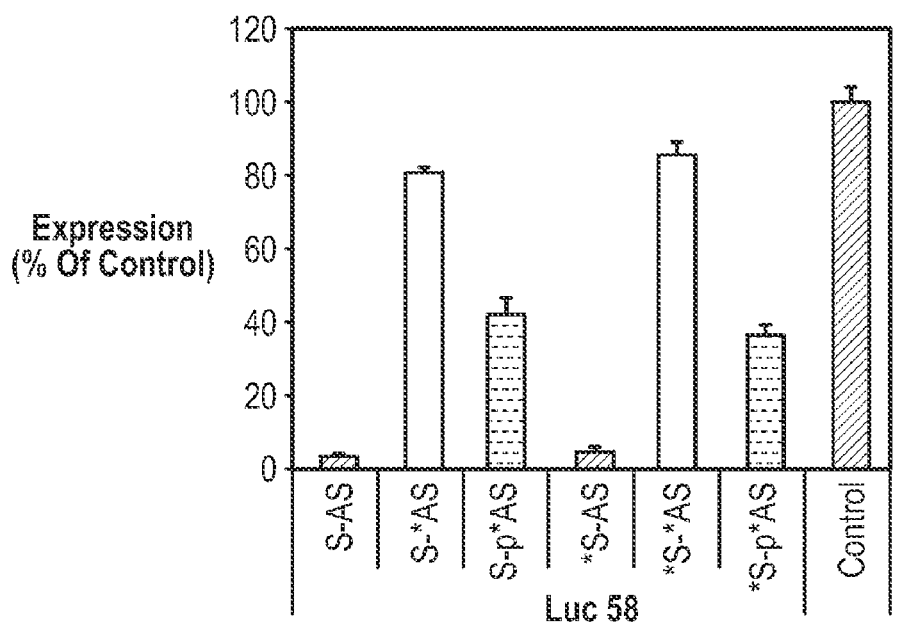
Figure 6C:
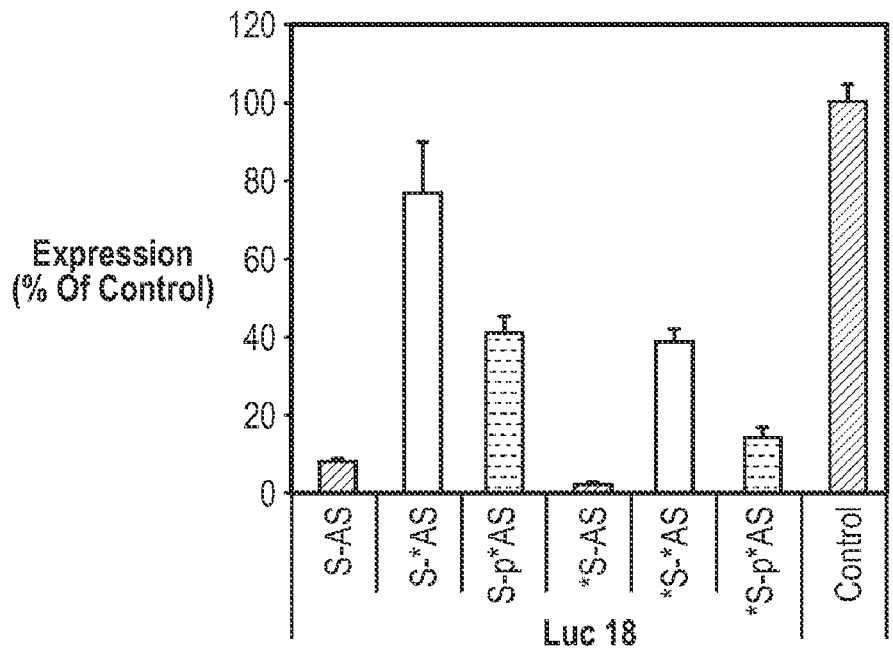
Figure 6D:
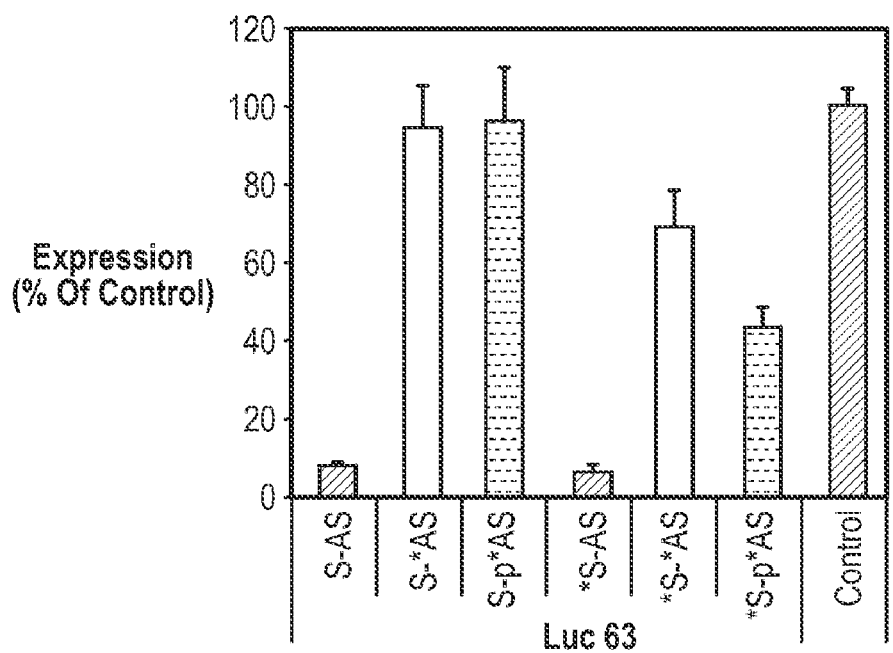
Figure 6E:
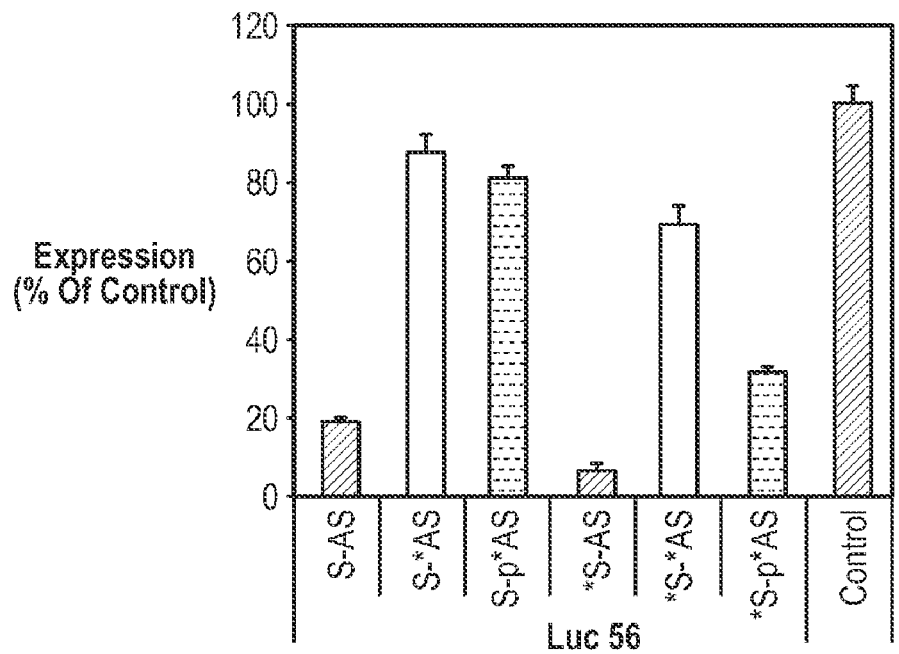
Figure 6F:
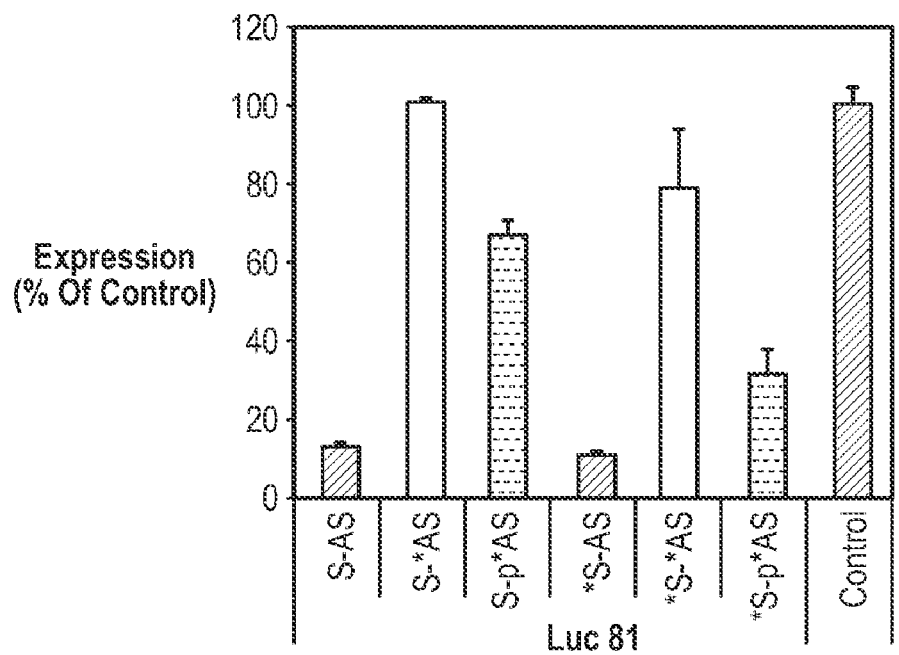

Using 2'-O-ACE chemistry as a platform for RNA synthesis, a modification walk consisting of one, two, or three consecutively modified nucleotides in sense (S) and antisense (AS) strands was performed on SEAP-2217, an siRNA directed against human secreted alkaline phosphatase (SEAP, SEAP-2217-sense strand 5'-GUGAUGUAUGUCA-GAGAGUdTdT-3' (SEQ. ID NO. 22). Subsequently, the silencing efficiency of these modified siRNAs was evaluated by cotransfecting each duplex with a SEAP expression vector (Clontech) into HEK293 cells (100 nM siRNA, 50 ng/well SEAP expression vector, Lipofectamine 2000) and assaying for a decrease in target protein activity twenty-four hours after transfection. FIG. 5 shows the relationship between modification and function for 2'-O-methylated SEAP-2217 siRNA. Unmodified duplexes targeting SEAP induce >90% silencing of the SEAP gene. Single base modifications of both S and AS strands induced little or no effect on siRNA activity, suggesting that no single 2'-hydroxyl group on either strand plays an indispensable role in target specific RNAi. In contrast, a walk of dual, side-by-side, modifications identified several key positions where the introduction of modified bases interfered significantly with silencing activity. The most profound interference with function was observed when two consecutive bases (positions 1 and 2) or three consecutive bases (positions 1, 2, and 3) of the 5' end of the AS strand were modified, thus hinting of a cooperative effect between adjacent modified groups. As similar modifications of the S strand failed to alter duplex functionality, paired 2'-O-methyl modified bases enable a distinction of S and AS strands and identification of key positions for target knockdown. Moreover, these experiments identify positions within the duplex that play a key role in target (and possibly off-target) silencing.

Example 7

Additional Analysis of the Effects of Various Combinations of Chemical Modifications on siRNA-Induced Gene Silencing To test the effects of 2'-O-methyl modifications on duplex functionality in various combinations, a series of siRNA directed against the luciferase gene (luc 8, 18, 56, 58, 63, and 81) were synthesized using 2'-O-ACE chemistry and modified to contain O-methyl groups at the 2' position of the ribose ring.

```
1 Luc  8   5'-GAAAAAUCAGAGAGAUCCU-3'   (SEQ. ID NO. 23)
  Luc 18   5'-UACCGGAAAACUCGACGCA-3'   (SEQ. ID NO. 24)
  Luc 56   5'-ACGUCGCCAGUCAAGUAAC-3'   (SEQ. ID NO. 25)
  Luc 58   5'-GAUUACGUCGCCAGUCAAG-3'   (SEQ. ID NO. 26)
  Luc 63   5'-AGAGAUCGUGGAUUACGUC-3'   (SEQ. ID NO. 27)
  Luc 81   5'-UGUUGUUUUGGAGCACGGA-3'   (SEQ. ID NO. 28)
```

(Sequences listed above are the sense strand.)

Specifically, siRNA containing 2'-O-methyl modifications on the two 5'-most nucleotides of (1) the sense strand, (2) the antisense strand, or (3) both strands, were co-transfected along with a Luc-expression plasmid (pCMVLuc, 50 ng/well) into HEK293 cells. Subsequently, a side-by-side comparison of the silencing ability of each duplex was performed to determine the effects of this modification on target transcript degradation.

Results of these studies showed that addition of the 2'-O-methyl groups only to the AS strand dramatically diminished the ability of the duplex to silence the target mRNA (see FIG. 6). In contrast, duplexes carrying this modification on the sense strand performed as well (luc 58, 63, 81) or better (luc 56, 8, 18) than equivalent, unmodified siRNA, suggesting that modification of the sense strand biased strand selection by RISC and (in some cases) increased the effective antisense strand concentration. Enhanced silencing could be the result of a decrease in the binding affinity of RISC to the 5' sense end of the molecule (and therefore an increase in the availability of free RISC for association to the opposing end), decreased ability of native kinases to phosphorylate the sense strand (thus decreasing competition between the sense and antisense strand for access to RISC), or a decline in the ability of RISC to unravel the duplex from the 5'-sense end. siRNA containing 2'-O-methyl modifications on both strands exhibited decreased silencing abilities that were between the values observed for molecules that contained modifications on either single strand. One interpretation of these results is that 2'-O-methyl modifications lowers the binding affinity that RISC has for the modified strand. In cases where both strands are modified, neither strand receives an advantage over its complement, and a new equilibrium representing an average of the functionality of both modified molecules is established.

To test whether the diminished level of silencing observed in cells containing 2'-O-methylated S/AS siRNA was the result of a debilitated capacity of cellular kinases to phosphorylate the duplexes, siRNAs carrying the 2'-O-methyl modifications were modified to carry a phosphate group on the 5' end of the AS strand. Specifically, Luc siRNAs carrying 2'-O-methyl groups on either: (1) positions 1 and 2 of the 5' end of the antisense strand; or (2) positions 1 and 2 of the 5' end of both antisense and sense strands, were 5'-phosphorylated on the AS strand during synthesis. These duplexes were then introduced into HEK293 cells using previously described procedures and tested for the ability to silence the desired target. Results showed that in 83% of the cases tested (10/12), 5' phosphorylation of the antisense strand improved the silencing efficiency of the duplex over the equivalent unphosphorylated molecule (FIG. 6). In the remaining two cases, silencing remained unchanged or was improved only marginally. These results demonstrate that the combination of 5' phosphorylation of the antisense strand and 2'O-methylation of positions 1 and 2 of the sense and antisense strands are compatible with maintaining duplex functionality. Moreover, as dual 2'-O-methyl modifications of positions 1 and 2 of a strand (in the absence of 5' phosphorylation of the terminal position) severely compromises the silencing ability of the unphosphorylated strand, this modification pattern (2'-O-methyl modification of positions 1 and 2 of the sense strand, 2'-O-methyl modification of positions 1 and 2 of the antisense strand, plus 5' phosphorylation of the antisense strand) identifies a strategy for eliminating sense strand off-targets without compromising on-target knockdown. Moreover, the potential effect of 2'-O-methylation on other steps led the authors to consider that the possibility that said modifications might also alter the ability of RISC to distinguish between intended targets that have 100% homology with the antisense strand and off-targets that have lesser amounts of homology.

Example 8

Figure 7:
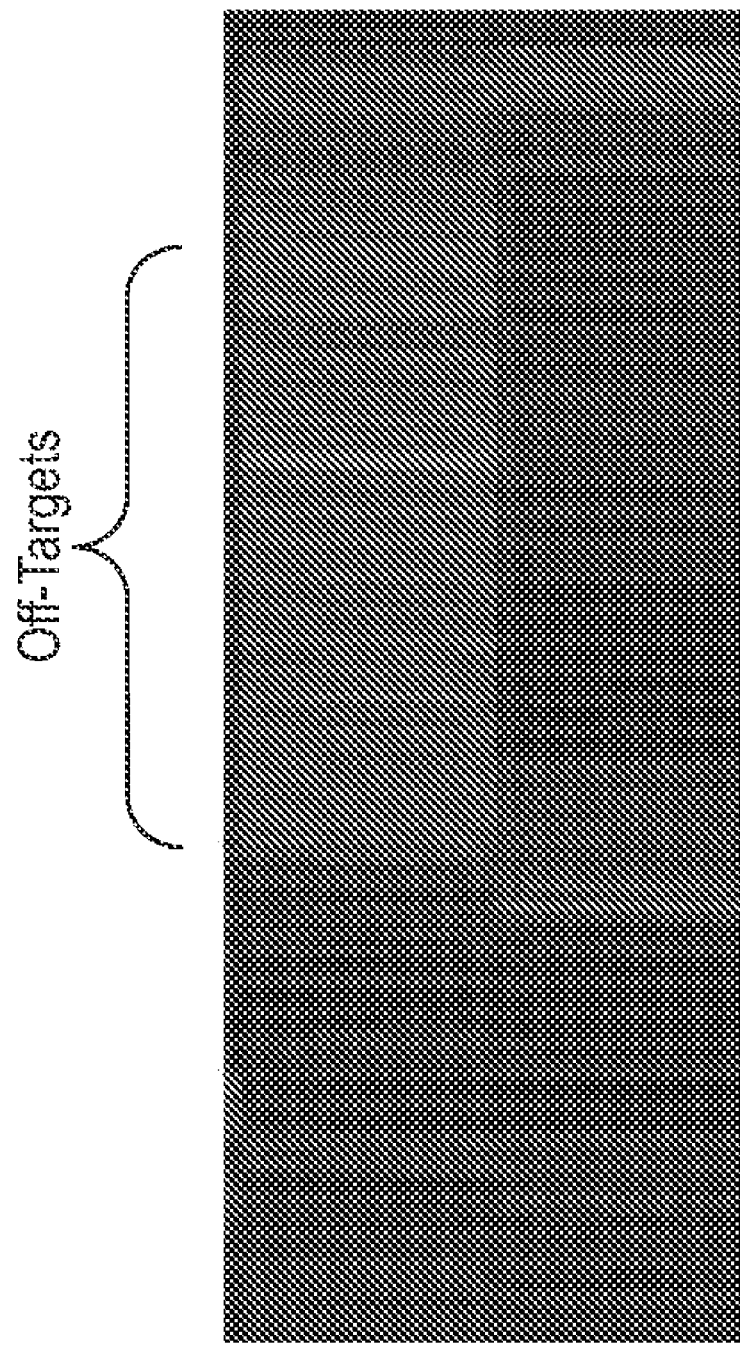
FIG. 7 depicts a microarray expression profile (a heatmap) generated in cells treated with IGF1R-73 targeting siRNA in unmodified (top) and modified (bottom) forms. The modification pattern includes 2'-O-methyl modification of positions 1 and 2 on both the sense and antisense strands, plus phosphorylation of carbon 5 of the ribose ring of the 5' terminal antisense nucleotide. (IGF1R-73: 5'-UGCUGACCUCUG-UUACCUC-3-', sense) (SEQ. ID NO. 1)
Figure 8A:
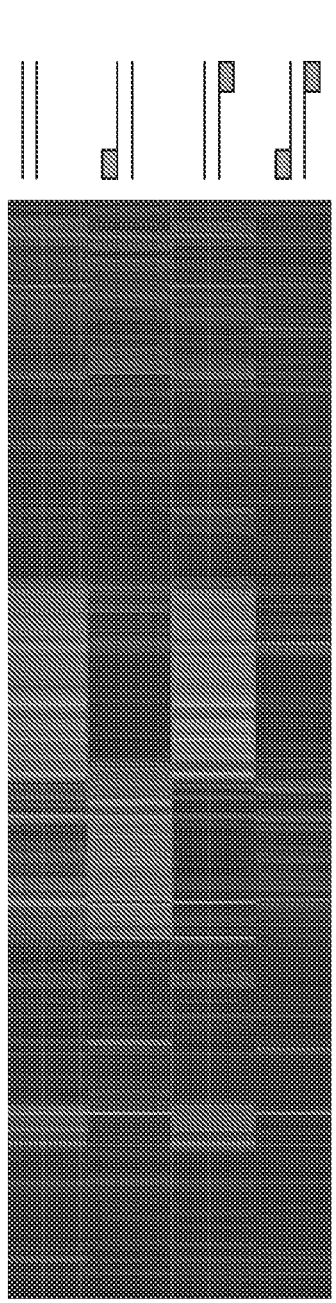
FIGS. 8A and 8B depict heatmaps of cells treated with siRNA targeting: (A) MAPK14, and (B) MPHOSPH1. Duplexes MAPK14-193 and MPHOSH1-202 are either unmodified (top), sense strand modified with 2'-O-methyl modification of positions 1 and 2 (second from top), antisense strand modified with 2'-O-methyl modification of positions 1 and 2 (third from top), or both strands modified with 2'-O-methyl modifications of positions 1 and 2 (bottom of each heat map). All duplexes tested contain a phosphate group on carbon 5 of the ribose ring of the 5' terminal antisense nucleotide. Arrows indicate the position and relative levels of silencing of the target. (MPHOS1-202: 5'-GACAUGC-GAAUGACACUAG-3' (SEQ. ID NO 2); Mapk14-193: 5'-CCUACAGAGAACUGCGGUU-3' (SEQ. ID NO. 3), sense strand.
Figure 8B:
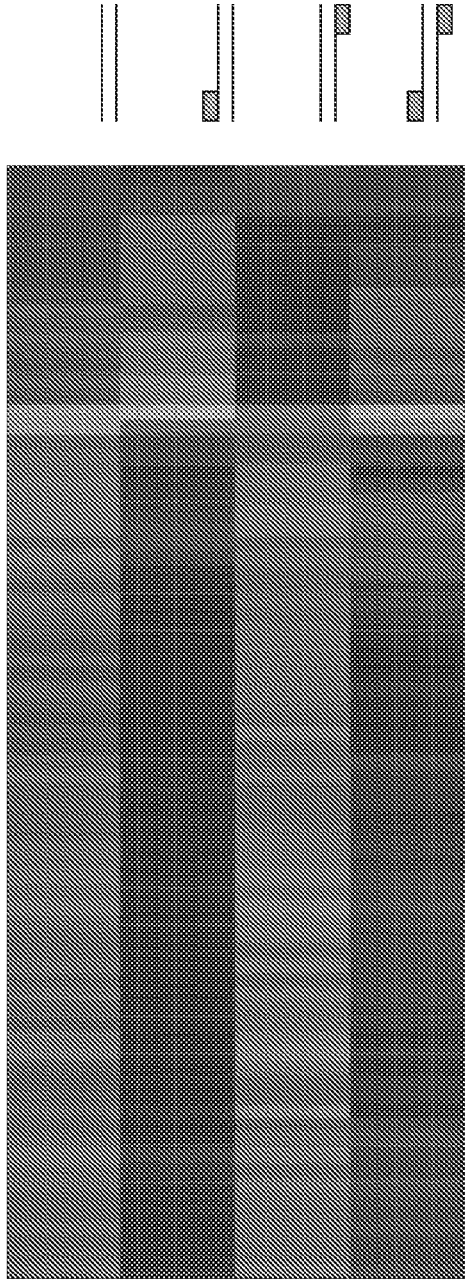
Figure 9:
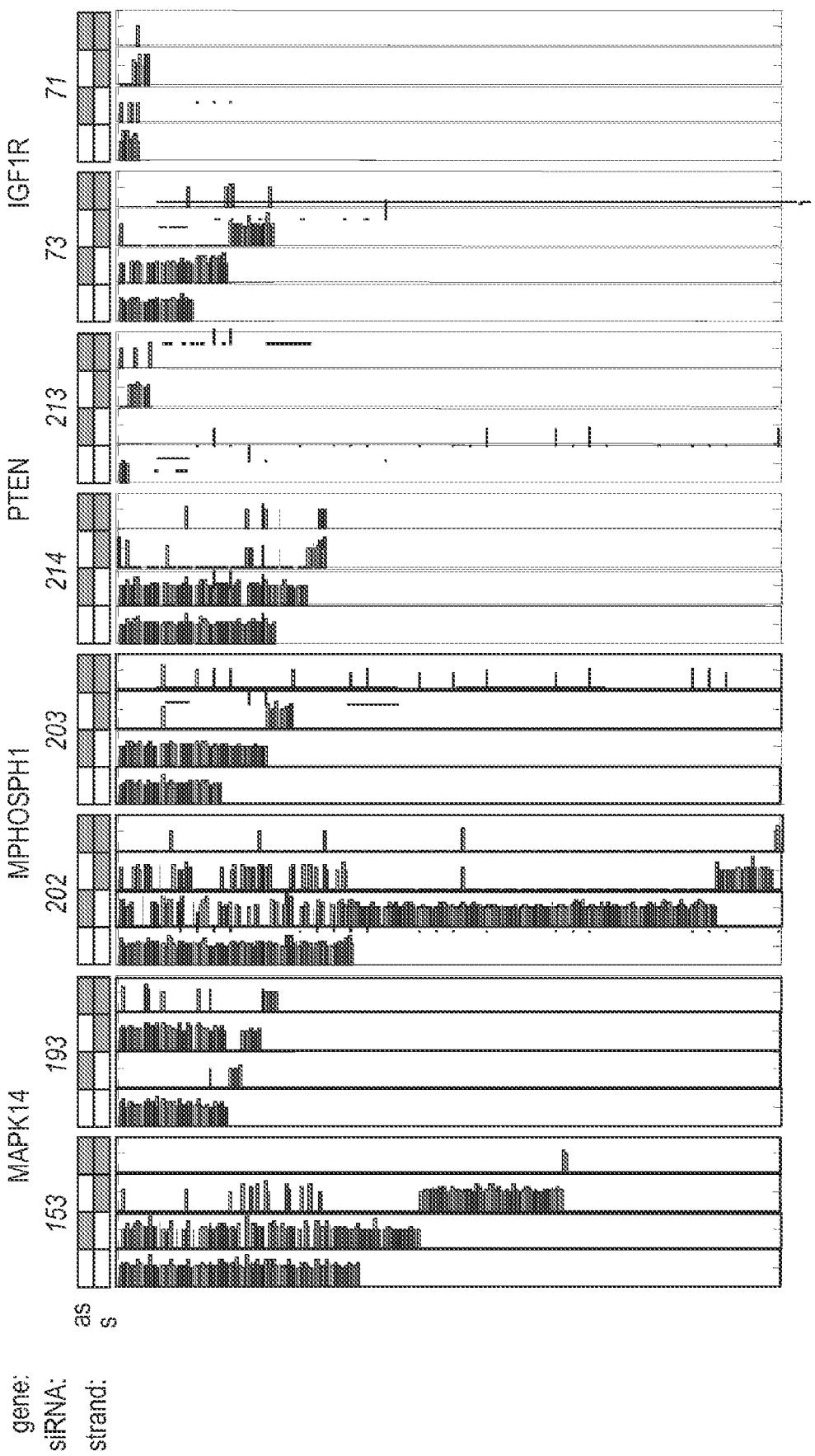
FIG. 9 depicts a summary of the number of off-targets for eight different siRNA targeting 4 separate targets MAPK14, MPHOSPH1, PTEN, and IGF1R. The pattern of siRNA chemical modification associated with each duplex is shown at the top of each column. In addition to (1) no 2'-O-methyl modifications, (2) 2'-O-methyl modifications on positions 1 and 2 of the antisense strand, (3) 2'-O-methyl modifications on positions 1 and 2 of the sense strand, or (4) 2'-O-methyl modifications on positions 1 and 2 of both strands, all duplexes tested contain a phosphate group on carbon 5 of the ribose ring of the 5' terminal antisense nucleotide. Sense strand sequences of molecules in this figure include: IGF1R-73: 5' UGCUGACCUCUGUUACCUC-3' (SEQ. ID NO. 4), Mapk14-193: 5' CCUACAGAGAA CUGCGGUU-3' (SEQ. ID NO. 5), Mapk14-153: 5' GUCAUCAGCUUUGUGC-CAC-3' (SEQ. ID NO. 6), MPHOS1-202:5' GACAUGC-GAAUGACACUAG-3' (SEQ. ID NO. 7), MPHOS1-203: 5' AGAGGAACU CUCUGCAAGC-3' (SEQ. ID NO. 8), PTEN 213: 5' UGGAGGGGAAUGCUCAGAA-3' (SEQ. ID NO. 9) and PTEN 214: 5' UAAAGAUGGCACUUUCCCG-3' (SEQ. ID NO. 10), IGFR-73: UGCUGACCUCUGUUACCUC-3' (SEQ. ID NO. 11), IGF1 R-71: 5' GCUCACGGUCAUUAC-CGAG-3' (SEQ. ID NO. 12)

Identification of Chemical Modification Patterns that Eliminate, Minimize, or Alter Off-Target Effects Generated by siRNA To determine whether siRNA containing (2'-O-methyl modification of positions 1 and 2 of the sense strand, 2'-O-methyl modification of positions 1 and 2 of the antisense strand, plus 5' phosphorylation of the antisense strand) modification pattern had the same or altered off-target effects, siRNA targeting IGFR1 (IGFR1-73) were transfected into cells in unmodified and modified states. As shown in FIG. 7, while the unmodified version of the siRNA induced significant off-target gene modulation, the modified form down regulated a much more limited subset. These findings were consistently observed across a broad range of siRNA tested (See FIG. 8 for MAPK14-153 heat map and MPHOSH1-202, and FIG. 9 for summation of results on 8 different siRNA targeting 4 genes). In all of these cases, silencing by the fully modified molecule was roughly equivalent to the unmodified molecule.

To determine whether the number or position of 2'-O-methyl modifications was important for the observed increased specificity, the inventors performed a walk of chemical modifications across the MAPK14-153. All of the duplexes in these studies with the exception of duplex D (unmodified duplex) and duplex F (2'-O-methyl modified on positions 1 and 2 of the antisense strand, no modification on the antisense strand) contain paired 2'-O-methyl modifications on positions 1 and 2 of the sense strand. Furthermore, all duplexes in this study (D->R) contain a phosphate group on the 5' end of the AS strand. In addition, the complementary strand in the remaining configurations (E, G->Q) contain the following modifications:

E: 2'O-methyl modification of positions 1 and 2 of the AS strand

G: 2'O-methyl modification of positions 2 and 3 of the AS strand

H: 2'O-methyl modification of positions 3 and 4 of the AS strand

I: 2'O-methyl modification of positions 4 and 5 of the AS strand

J: 2'O-methyl modification of positions 5 and 6 of the AS strand

K: 2'O-methyl modification of positions 6 and 7 of the AS strand

L: 2'O-methyl modification of positions 7 and 8 of the AS strand

M: 2'O-methyl modification of positions 8 and 9 of the AS strand

N: 2'O-methyl modification of positions 9 and 10 of the AS strand

O: 2'O-methyl modification of positions 10 and 111 of the AS strand

P: 2'O-methyl modification of position 1 of the AS strand

Q: 2'O-methyl modification of position 2 of the AS strand

As shown in FIG. 10a, only three modification patterns, E, G, and Q exhibit significant reductions in off-target effects. As the common element amongst all three of these molecules is the modification at position 2 on the antisense strand, this position is identified as a key element for eliminating off-targets.

To confirm this finding, three additional siRNAs targeting MAPK14, KNTC2, and STK6 were designed to contain: (1) the modifications on positions 1 and 2 of the sense strand; (2) the modifications on positions 1 and 2 of the sense strand plus the modifications on position 1 of the antisense strand; (3) the modifications on positions 1 and 2 of the sense strand plus the modifications on position 2 of the antisense strand; (4) the modifications on positions 1 and 2 of the sense strand plus the modifications on positions 1 and 2 of the antisense strand. The off-target effects generated by these molecules were compared with unmodified siRNA. In all of the cases studied, the antisense strand also contains a phosphate group on the 5' carbon of the 5'-terminal nucleotide. siRNA targeting MAPK14, KNTC2, and STK6 (MAPK14, 5' 193 CCUACA-GAGAACUGCGGUU-3' (SEQ. ID NO. 29), sense sequence; KNTC2, 5' GGCJUCCUUACAAGGAGAU-3' (SEQ. ID NO. 30), sense sequence; and STK6, 5' CGGGU-CUUGUGUCCUUCAA-3' (SEQ. ID NO. 31), sense sequence) all show significant levels of off-target effects when they are unmodified (FIG. 10b). In contrast, addition of the following modification pattern: 2'-O-methyl modification of sense nucleotides 1 and 2, plus 2'-O-methyl modification of antisense nucleotides 1 and 2 (or just 2), plus phosphorylation of the 5' carbon of the first antisense nucleotide, was sufficient to eliminate the majority of off-target effects. These studies demonstrate the fundamental importance of position 2 in limiting off-target effects and the ability of the chemical modification pattern described in embodiment 1 to reduce and/or eliminate these effects.

Example 9

Assessment of Base-Pair Mismatches to Eliminate Off-Target Effects: a Comparison with Chemically Modified siRNA To further explore the importance of position 2 in off-target effects, base pair mismatches were incorporated into siRNA targeting the MAPK14 gene. Duplexes carrying single base pair mismatches (between the antisense strand and the target site of the target) were then compared with siRNA carrying paired chemical modifications (2'-O-methyl modification) at positions across the molecule (i.e., positions 1 and 2, 2 and 3, 3 and 4, etc. . . . of the antisense strand). Results of these experiments are provided in FIG. 11 and demonstrate several important points. First, as observed previously, chemical modification of positions 1 and 2 have the greatest effect on eliminating the off-target signature, while paired 2'-O-methyl modifications at other positions provided lesser amounts of off-target silencing. Surprisingly, introduction of a basepair mismatches at various positions across the duplex provided variable results, depending upon the position of the mismatch. A mismatch at position 1 failed to eliminate the off-target signature of the unmodified molecule and led to additional/more enhanced down regulation of some of the genes. Introduction of base-pair mismatches at positions 2-7 eliminated a substantial portion of the signature generated by unmodified duplexes, but frequently led to altered patterns of expression of other off-targeted genes. For MAPK14-153, this was particularly evident when mismatches were introduced at position 4 of the antisense strand. Together, these studies demonstrate that while both base pair mismatches and embodiment 1 chemical modification patterns can alter siRNA off-target effects, chemical modification patterns are superior due to the fact that a secondary signature does not replace the pattern observed in unmodified molecules.

Example 10

Figure 12A:
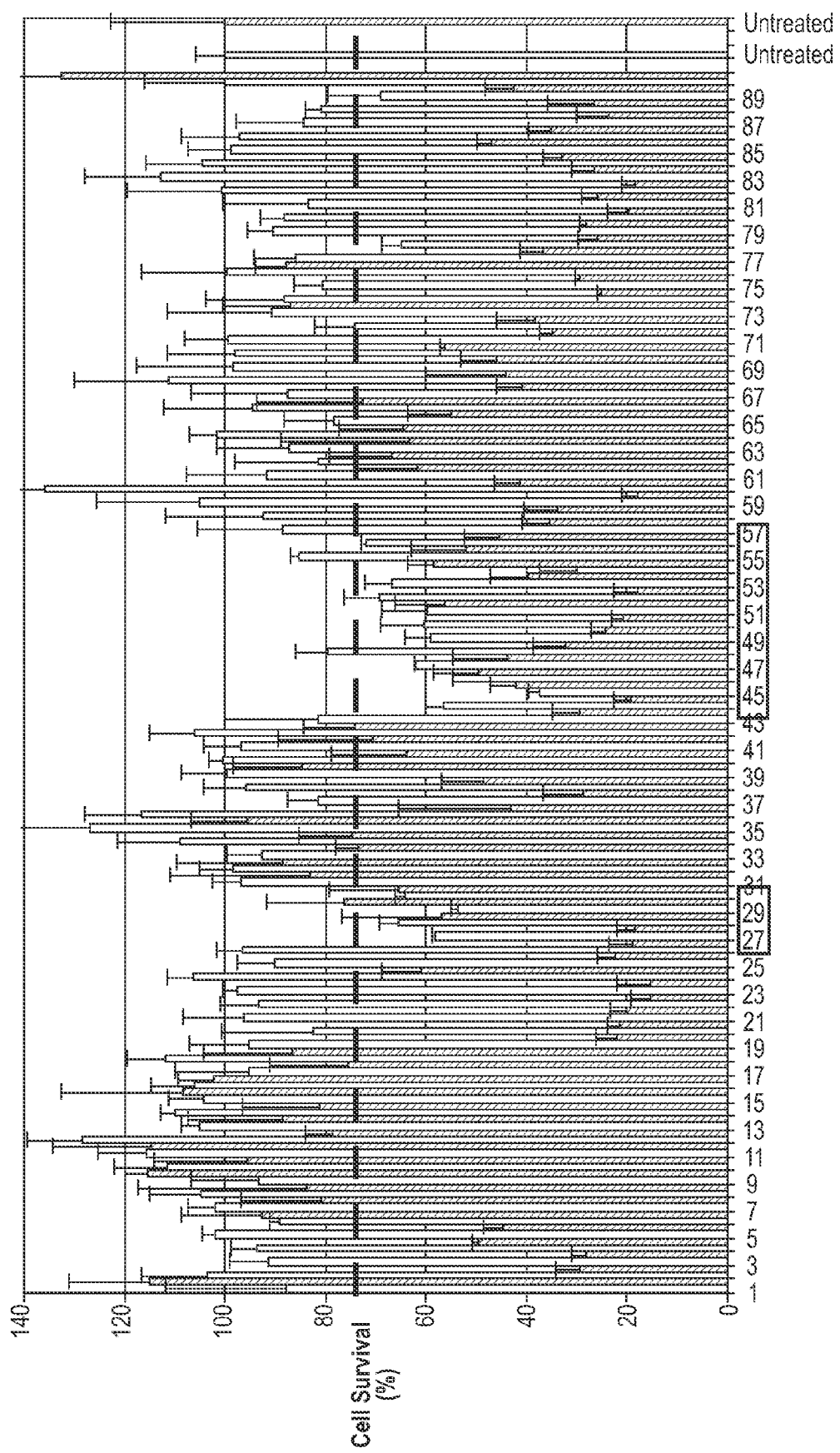

Demonstration that siRNA Off-Target Effects Generate Observable Phenotypes: Toxic siRNA The importance of the present invention became evident when it was recognized that off-target effects can induce phenotypes that were not associated with target knockdown. This phenomenon became apparent in a study of siRNA induced off-targeting and cellular toxicity. A population of randomly selected siRNA derived from a siRNA walk targeting DBI (NM-020548, position 202-291) were assessed for the ability to induce toxicity. The collection of targeting siRNA consisted of 90 individual (19 nt) duplexes and covered the respective region in single base steps. Duplexes were transfected into HeLa cells (10,00 cells per well, 10 nM siRNA) using Lipofectamine 2000 (Invitrogen) and a threshold of 75% cell viability was used as an arbitrary cutoff to distinguish toxic from nontoxic sequences. The survival of cells after treatment was determined by Alamar Blue (BioSource Int.) cytotoxicity assay according to manufacturers instructions.

siRNA transfected under these conditions were observed to induce varying levels of cellular toxicity. Overall, 14 out of 90 siRNA duplexes (15.5%) were found to decrease cellular viability below 75% (FIG. 12a). As examples of both toxic and non-toxic siRNA could be found to induce strong DBI silencing, the relative cytotoxicity of each siRNA was unrelated to target specific knockdown.

Figure 12B:
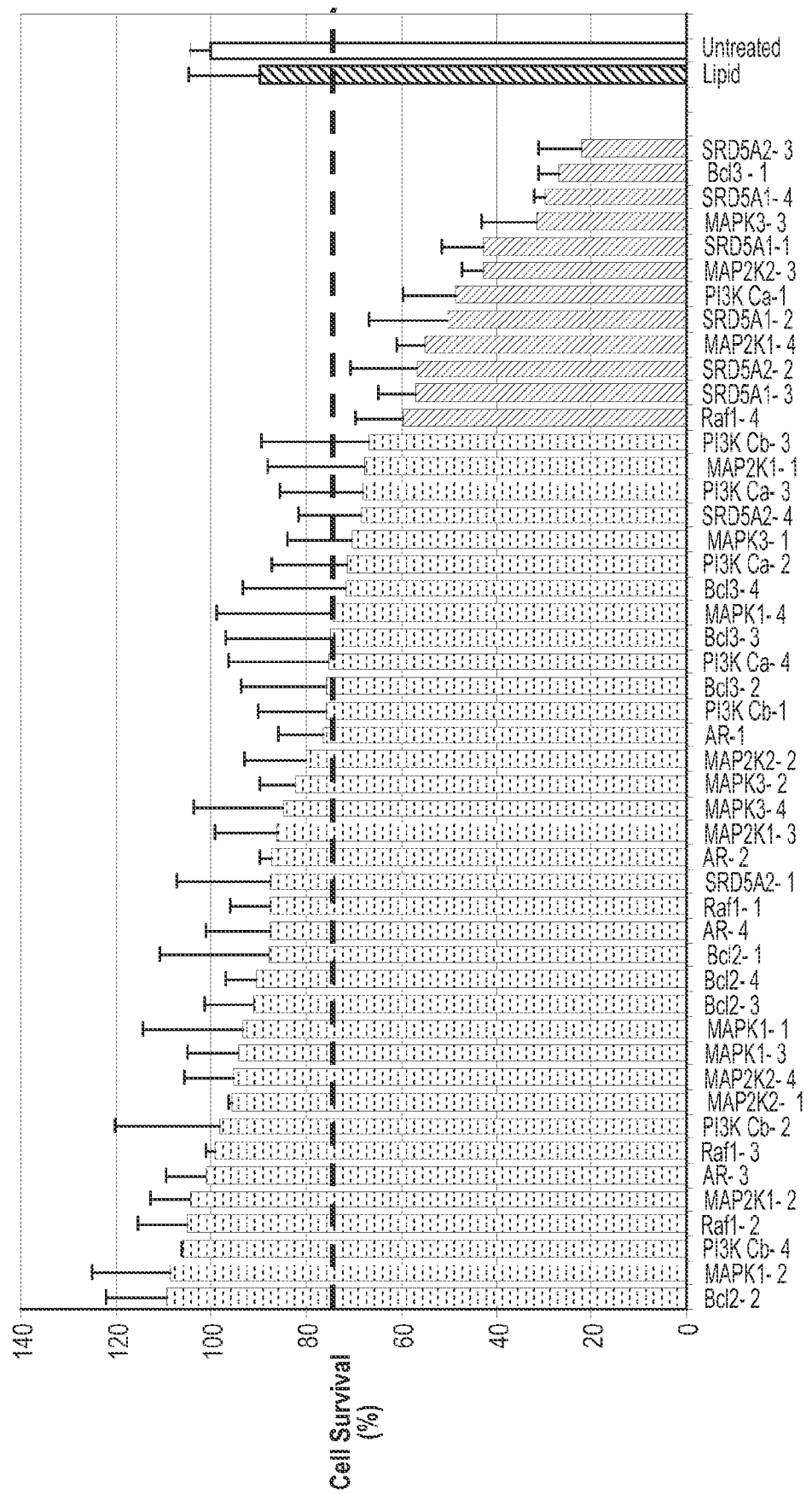
Figure 12C:
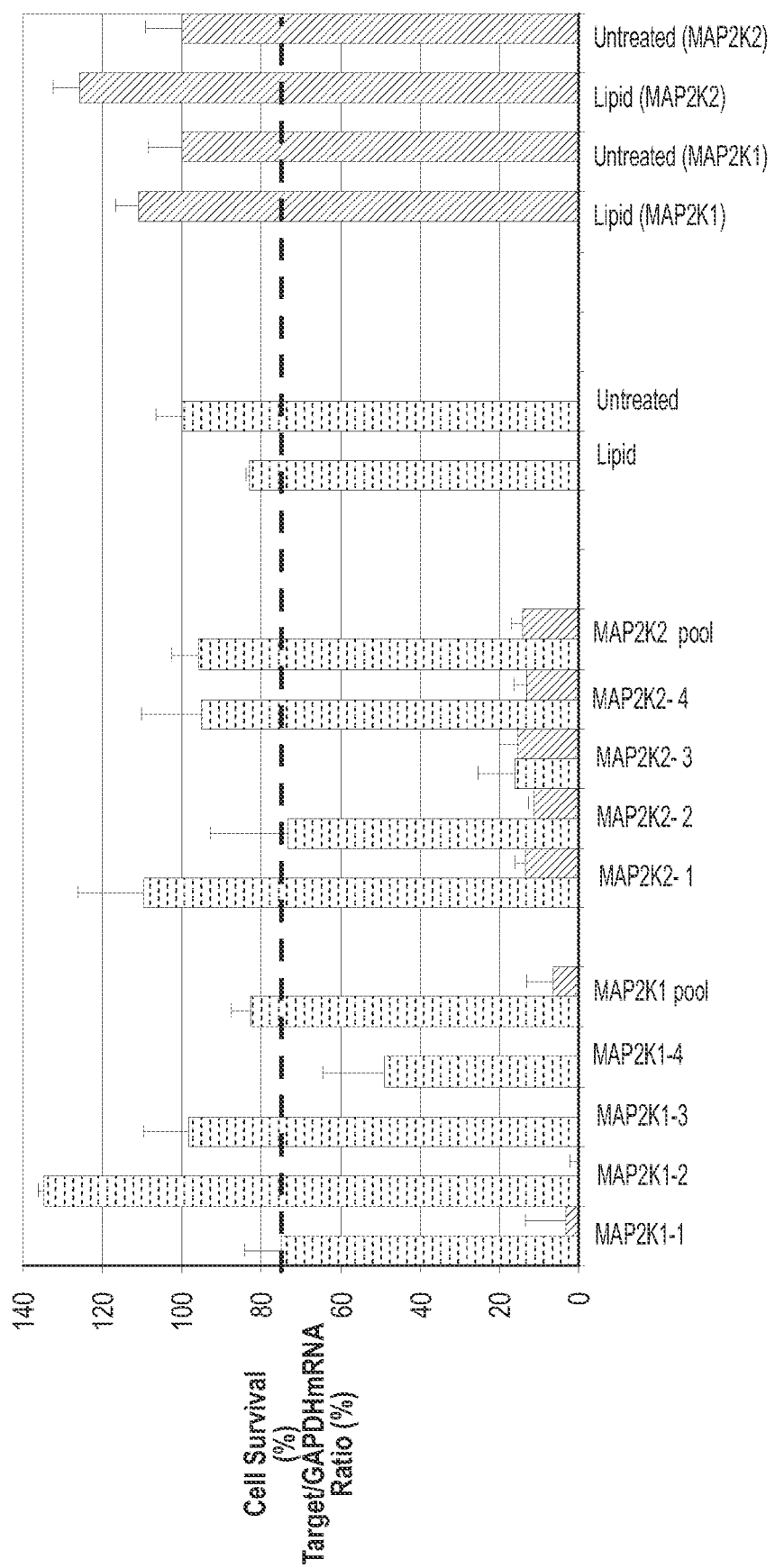
Figure 12D:
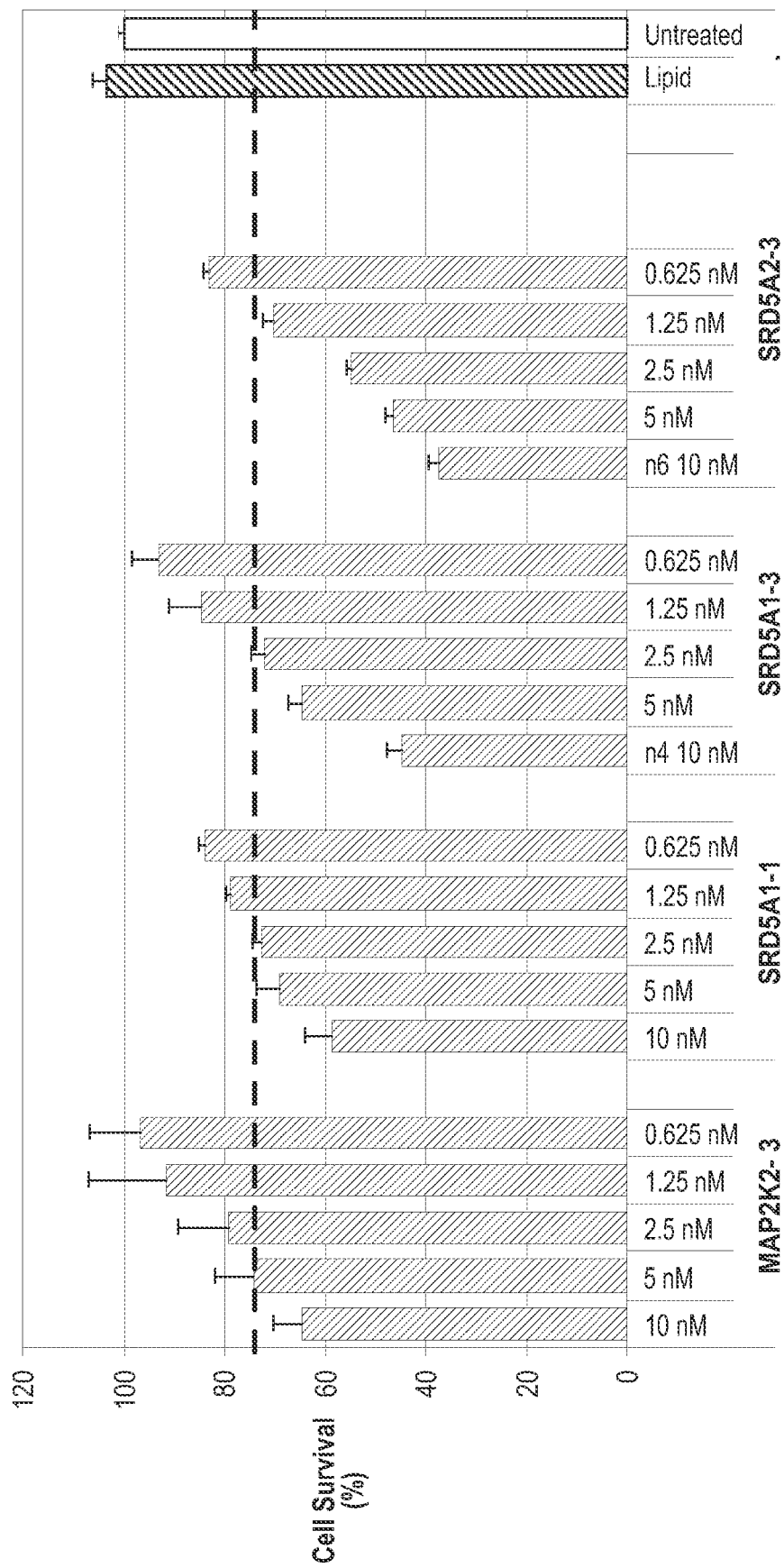

Independent confirmation of the siRNA induced toxicity was obtained from analysis of a separate collection of 48 functional (>70% silencing) siRNA targeting 12 different genes (ARAF1, NM-001654, MAP2K1, NM-002755, MAP2K2, NM-030662, PI3K-CA, NM-006218, Pi3K-CB, NM-006219 Bcl2, NM-000633, Bcl3, NM-005178, MAPK1, NM-002745, MAPK3, NM-002746, AR, NM-000044, SRD5a1, NM-001047, SRD5a2, NM-000348, four siRNAs per gene, FIG. 12b). Only twelve of the forty-eight sequences (25%) decreased cellular viability below 75%. An exemplary group of duplexes from this collection are shown in FIG. 12c. While all eight duplexes targeting MAPK1 and MAPK2 show greater than 80% gene silencing, only a single siRNA in each quartet reduces cell viability below 75% (MAPK1-d4 and MAPK2-d3). Thus, as the remaining siRNAs in each group were equally functional in the ability to silence the target, but non-toxic, the toxicity induced by MAP2K1-d4 and MAP2K2-d3 is unrelated to target knockdown. Furthermore, the relative level of toxicity was found to be dependent upon the concentration of the siRNA during transfection (FIG. 12d). As both siRNA induced toxicity and off-target effects show a dependence on siRNA concentration, it was predicted that siRNA induced toxicity was an off-target effect.

The linear display of the distribution of toxic siRNA along the DBI walk showed that the dispersal of these sequences was frequently non-random (i.e., clustered) and suggested the presence of one or more motifs that were responsible for the observed toxicity (FIG. 12a, boxed areas). Subsequent analysis of the toxic sequences from the random functional siRNA set revealed that all twelve sequences contained either an AAA/UUU or GCCA/UGGC motif. To test whether a correlation existed between the presence of these motifs and toxicity, three additional, randomly selected, groups of siRNA that contained either AAA/UUU motifs, GCCA/UGGC motifs, or neither motif, were chosen and tested for the ability to induce cell death. As shown in FIGS. 13a and 13b, siRNA containing the AAA/UUU and GCCA/UGGC motifs exhibited a higher probability of inducing toxicity (56% and 53%, respectively) than non-motif containing siRNA (FIG. 13c, 6%). As the T-Test p-value for these two samples was $1.3 \times 10^{-7}$ these findings strongly support the notion that a strong correlation exists between siRNA induced cellular toxicity and delivery of duplexes containing the AAA/UUU or GCCA/UGGC motifs. The target sequences for the siRNAs used to generate the data of FIGS. 12 and 13 are provided in Table 8. Modifications corresponding siRNAs, when employed, are indicated in the examples and figure descriptions.

Note: Sequences for 14L are also present in a modified form where positions 1 and 2 of the sense and antisense strands contain 2'-O-methyl groups and positions 1 of the antisense strand also contains a phosphate group on the 5' carbon.

The data above support a hypothesis that siRNA can induce toxicity in a sequence specific, target independent mechanism. The inventors performed two separate experiments to test the dependence of siRNA-induced toxicity on the RNAi mechanism. The results of these experiments are presented below and demonstrate that the toxicity is mediated by the RNAi pathway. As previous experiments demonstrated that the toxicity was not associated with target knockdown, a third experiment was performed to determine whether the chemical modification patterns described in the first embodiment could eliminate the toxicity.

Figure 14A:
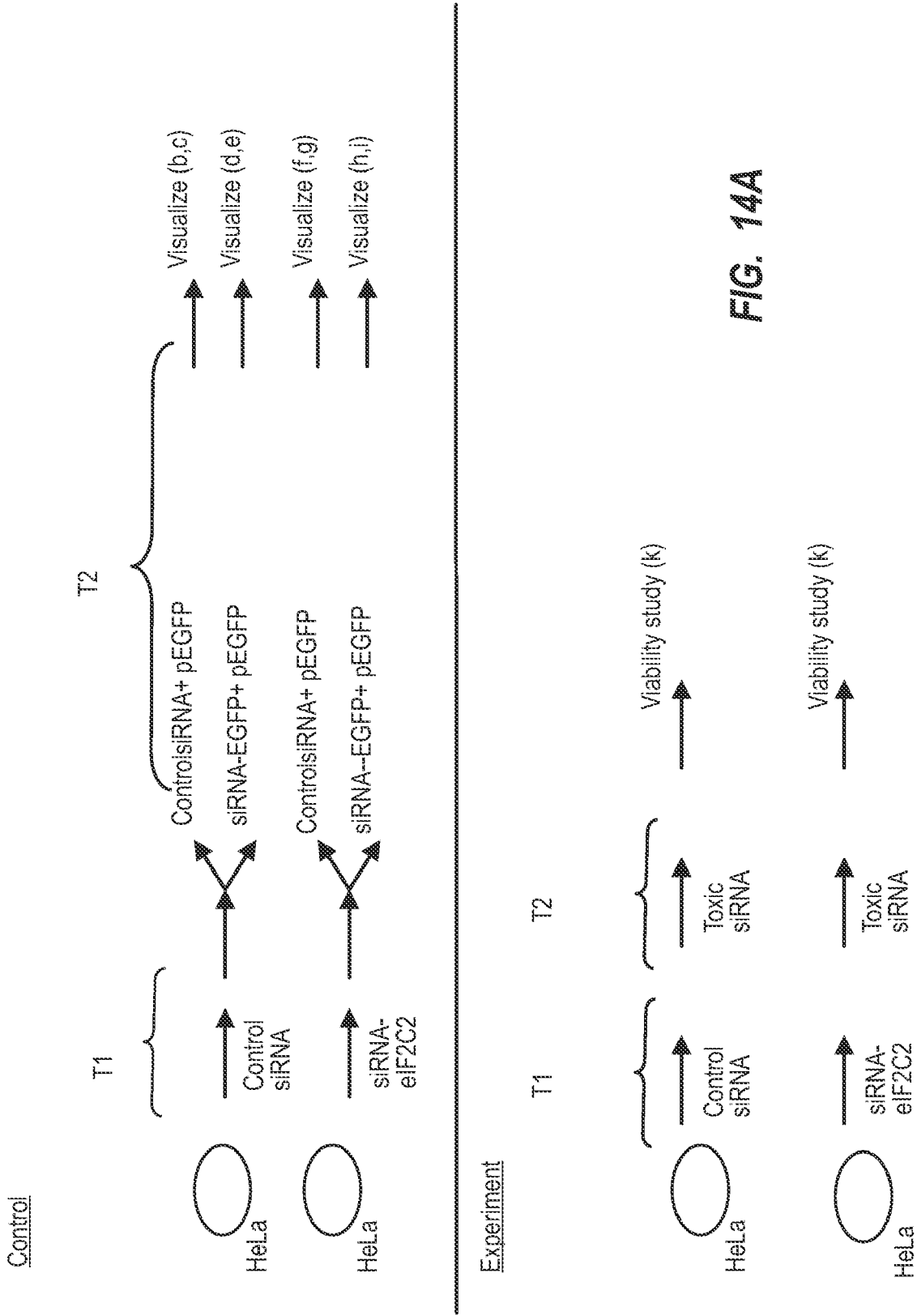
Figure 14G:
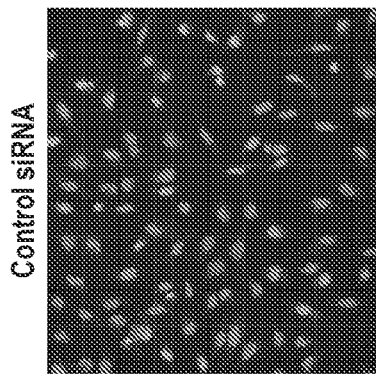
Figure 14I:
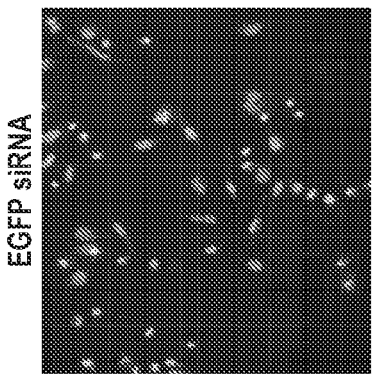
Figure 14F:
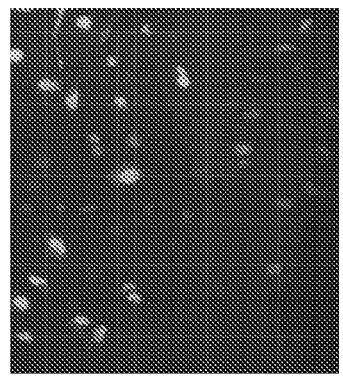
Figure 14H:
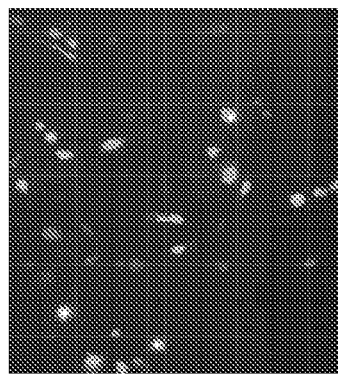
Figure 14C:
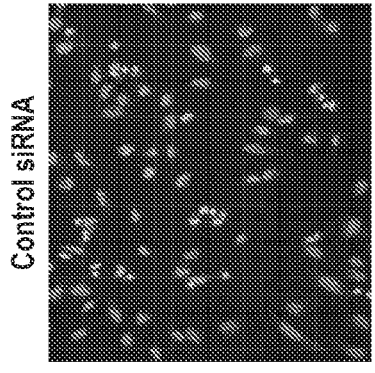
Figure 14E:
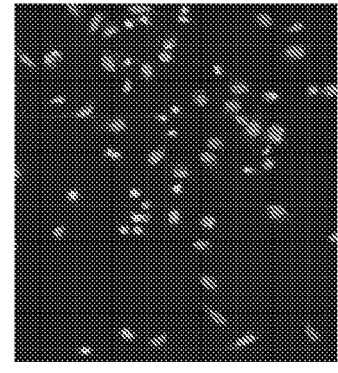
Figure 14B:
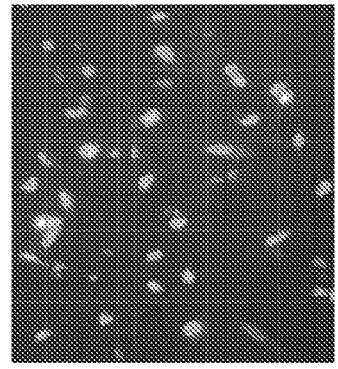
Figure 14D:
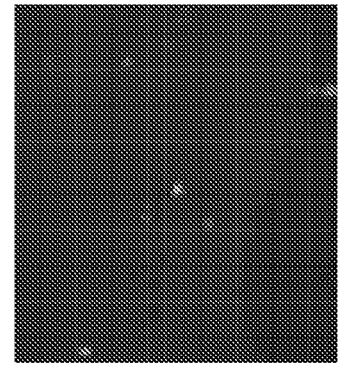
Figure 14J:
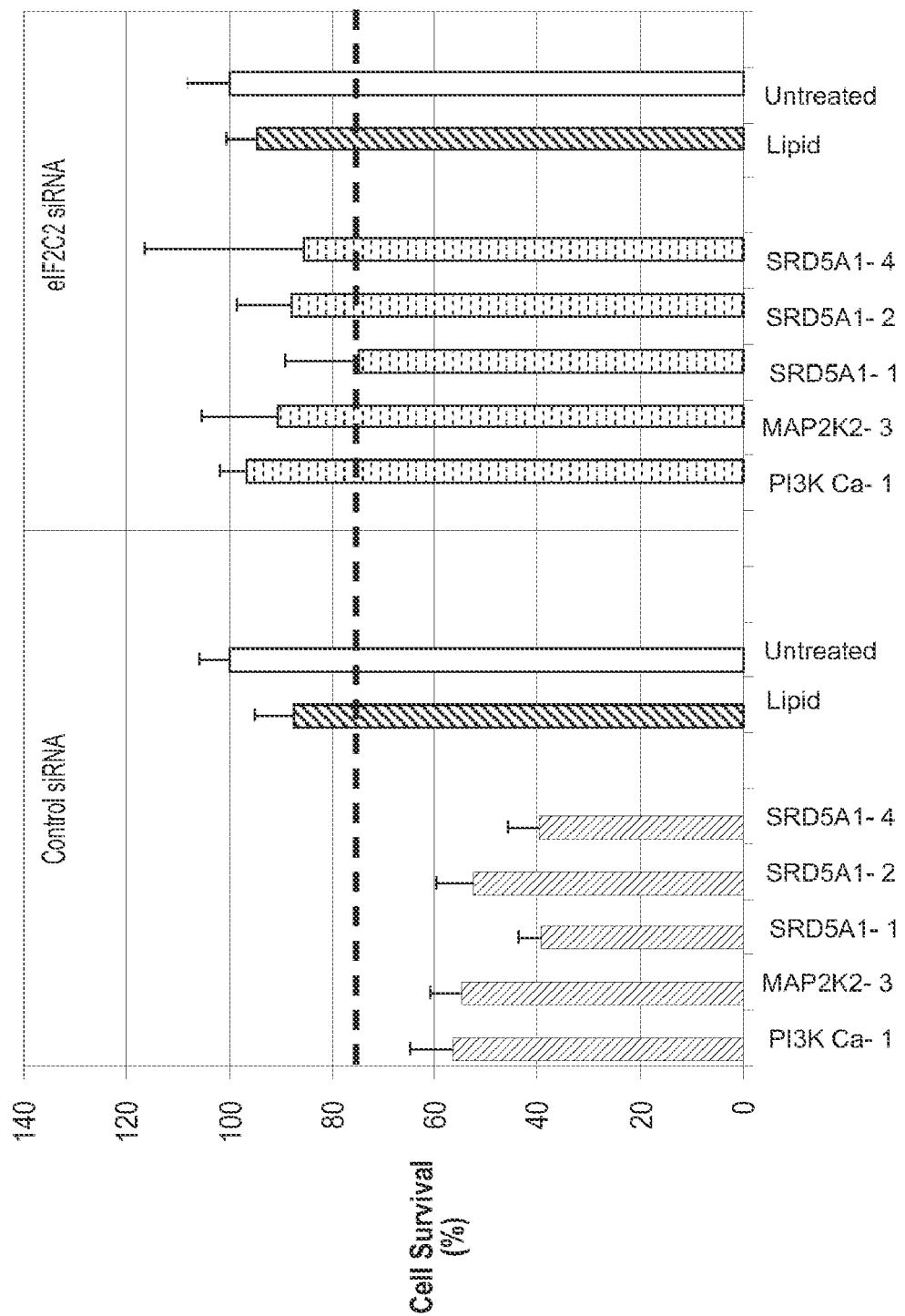
Figure 14K:
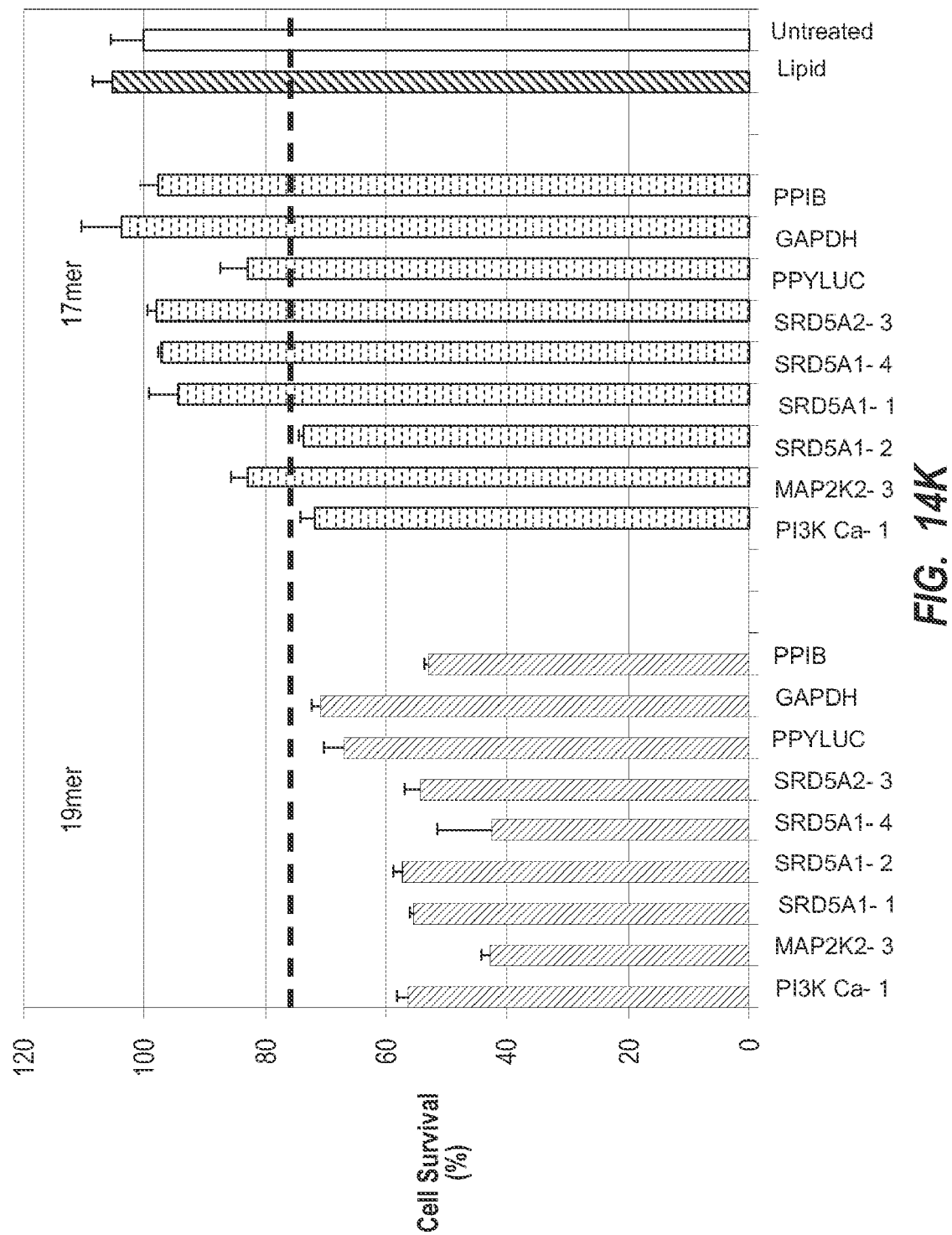
Figure 14L:
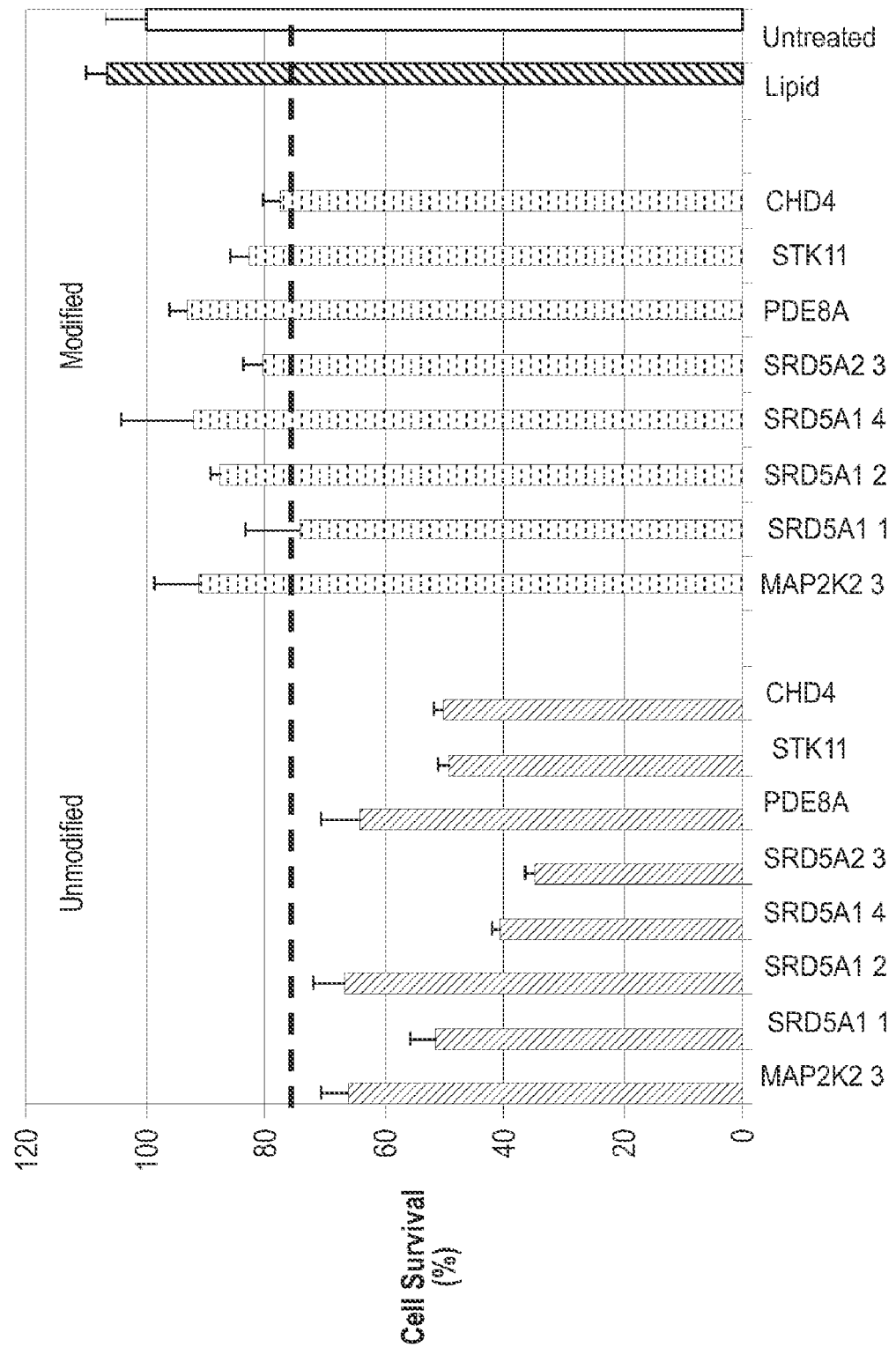

In the first experiment, the ability of toxic motif containing siRNA to induce cell death was investigated under circumstances where the RNAi mechanism was severely compromised. Previous studies revealed that eIF2C2/hAgo2 is responsible for mRNA cleavage and that knockdown of this gene product severely cripples this pathway. The inventors confirmed this finding (FIG. 14a-i) and then assessed the importance of this pathway in newly discovered siRNA-induced toxicity. To test this, cells transfected with the eIF2C2/hAgo2 siRNA pool (T1) were subsequently transfected with toxic siRNA containing either the AAA/UUU or GCCA/UGG motifs (FIG. 14a, "Experiment"). The results of these experiments demonstrated that in the absence of an intact RNAi pathway, toxic siRNA were unable to induce the cell death phenotype (FIG. 14j). As parallel experiments where the RNAi pathway was left intact exhibited toxicity characteristic of these sequences, it was concluded that an intact RNAi pathway was necessary for siRNA-induced toxicity. These experiment strongly support the hypothesis that toxic siRNA induce their phenotype through the RNAi pathway. Since the observed toxicity is unrelated to the level or degree of target knockdown, it is likely that off-targeting is responsible for the observed toxic phenotype.

Further support for the involvement of the RNAi pathway in siRNA toxicity came from an experiments where the size of the duplex was reduced from 19 bp to17 bp. Previous studies have shown that duplexes that are shorter than 19 bp targeted mRNA sequences inefficiently, most likely due to the fact that Dicer and/or RISC fail to mediate RNAi when duplex sequence length drops below 19 bp (Elbashir, S. M. et al. "Duplexes of 21-nucleotide RNAs mediate RNA interference in cultured mammalian cells" Nature 2001 May 24; 411(6836):494-8). When the length of known, 19 bp, toxic siRNA was reduced by 2 bp (17 bp total length, no disruption of the motif) the level of toxicity was reduced dramatically (FIG. 14k), suggesting that entry and/or processing by RISC is necessary for induction of toxicity. These results again implicate the RNAi pathway in this form of siRNA induced cellular toxicity. Since the observed toxicity is unrelated to the level or degree of target knockdown, it is likely that off-targeting is responsible for the observed toxic phenotype.

As noted above, the modifications described in the first embodiment of the invention have been shown to eliminate off-target effects. As siRNA-induced cellular toxicity is dependent on RNAi, but unrelated to target knockdown, the inventors decided to test whether modifications that eliminate off-targeting, abolish siRNA-induced cellular toxicity. To accomplish this, a variation of the chemical modification pattern described in the first embodiment was added to siRNA that were known to induce toxicity in an RNAi-dependent mechanism. Specifically, siRNA synthesized to carry the following modifications: 2'-O-methyl groups on positions 1 and 2 of both the sense and antisense strands, plus a 5' phosphate group on carbon 5 of the 5' terminal antisense nucleotide. As shown in FIG. 14-1, when eight separate unmodified, toxic siRNA (MAP2K2 d3, SRD5 u1 d1, SRD5 u1 d2, SRD5 u1 d4, SRD5A2 d3, PDE8A, STK11, and CHD4) were transfected into cells, each decreased cell viability below 75%. In contrast, chemical modification of all eight duplexes markedly decreased siRNA-induced toxicity without significantly altering target specific knockdown. These findings strongly support the premise that siRNA induced toxicity induced by AAA/UUU or GCCA/UGGC containing siRNA is the result of off-target effects. More importantly, the findings presented here suggest that off-target induced phenotypes can be eliminated by the addition of the modifications of the invention.

TABLE I

Sequences Used For the Data of FIGS. 12-14

| FIG. | Accession # | Gene Name | Designation | siRNA Target Sequence | SEQ. ID NO. |
|---|---|---|---|---|---|
| 12A | | | | | |
| | NM_020548 | DBI | | | |
| | | | 1 | ACGGGCAAGGCCAAGUGGG | 32 |
| | | | 2 | CGGGCAAGGCCAAGUGGGA | 33 |
| | | | 3 | GGGCAAGGCCAAGUGGGAU | 34 |
| | | | 4 | GGCAAGGCCAAGUGGGAUG | 35 |
| | | | 5 | GCAAGGCCAAGUGGGAUGC | 36 |
| | | | 6 | CAAGGCCAAGUGGGAUGCC | 37 |
| | | | 7 | AAGGCCAAGUGGGAUGCCU | 38 |
| | | | 8 | AGGCCAAGUGGGAUGCCUG | 39 |
| | | | 9 | GGCCAAGUGGGAUGCCUGG | 40 |
| | | | 10 | GCCAAGUGGGAUGCCUGGA | 41 |
| | | | 11 | CCAAGUGGGAUGCCUGGAA | 42 |
| | | | 12 | CAAGUGGGAUGCCUGGAAU | 43 |
| | | | 13 | AAGUGGGAUGCCUGGAAUG | 44 |
| | | | 14 | AGUGGGAUGCCUGGAAUGA | 45 |
| | | | 15 | GUGGGAUGCCUGGAAUGAG | 46 |

TABLE I-continued

Sequences Used For the Data of FIGS. 12-14

| FIG. | Accession # | Gene Name | Designation | siRNA Target Sequence | SEQ. ID NO. |
|---|---|---|---|---|---|
| | | | 16 | UGGGAUGCCUGGAAUGAGC | 47 |
| | | | 17 | GGGAUGCCUGGAAUGAGCU | 48 |
| | | | 18 | GGAUGCCUGGAAUGAGCUG | 49 |
| | | | 19 | GAUGCCUGGAAUGAGCUGA | 50 |
| | | | 20 | AUGCCUGGAAUGAGCUGAA | 51 |
| | | | 21 | UGCCUGGAAUGAGCUGAAA | 52 |
| | | | 22 | GCCUGGAAUGAGCUGAAAG | 53 |
| | | | 23 | CCUGGAAUGAGCUGAAAGG | 54 |
| | | | 24 | CUGGAAUGAGCUGAAAGGG | 55 |
| | | | 25 | UGGAAUGAGCUGAAAGGGA | 56 |
| | | | 26 | GGAAUGAGCUGAAAGGGAC | 57 |
| | | | 27 | GAAUGAGCUGAAAGGGACU | 58 |
| | | | 28 | AAUGAGCUGAAAGGGACUU | 59 |
| | | | 29 | AUGAGCUGAAAGGGACUUC | 60 |
| | | | 30 | UGAGCUGAAAGGGACUUCC | 61 |
| | | | 31 | GAGCUGAAAGGGACUUCCA | 62 |
| | | | 32 | AGCUGAAAGGGACUUCCAA | 63 |
| | | | 33 | GCUGAAAGGGACUUCCAAG | 64 |
| | | | 34 | CUGAAAGGGACUUCCAAGG | 65 |
| | | | 35 | UGAAAGGGACUUCCAAGGA | 66 |
| | | | 36 | GAAAGGGACUUCCAAGGAA | 67 |
| | | | 37 | AAAGGGACUUCCAAGGAAG | 68 |
| | | | 38 | AAGGGACUUCCAAGGAAGA | 69 |
| | | | 39 | AGGGACUUCCAAGGAAGAU | 70 |
| | | | 40 | GGGACUUCCAAGGAAGAUG | 71 |
| | | | 41 | GGACUUCCAAGGAAGAUGC | 72 |
| | | | 42 | GACUUCCAAGGAAGAUGCC | 73 |
| | | | 43 | ACUUCCAAGGAAGAUGCCA | 74 |
| | | | 44 | CUUCCAAGGAAGAUGCCAU | 75 |
| | | | 45 | UUCCAAGGAAGAUGCCAUG | 76 |
| | | | 46 | UCCAAGGAAGAUGCCAUGA | 77 |
| | | | 47 | CCAAGGAAGAUGCCAUGAA | 78 |
| | | | 48 | CAAGGAAGAUGCCAUGAAA | 79 |
| | | | 49 | AAGGAAGAUGCCAUGAAAG | 80 |
| | | | 50 | AGGAAGAUGCCAUGAAAGC | 81 |
| | | | 51 | GGAAGAUGCCAUGAAAGCU | 82 |
| | | | 52 | GAAGAUGCCAUGAAAGCUU | 83 |

TABLE I-continued

Sequences Used For the Data of FIGS. 12-14

| FIG. | Accession # | Gene Name | Designation | siRNA Target Sequence | SEQ. ID NO. |
|---|---|---|---|---|---|
| | | | 53 | AAGAUGCCAUGAAAGCUUA | 84 |
| | | | 54 | AGAUGCCAUGAAAGCUUAC | 85 |
| | | | 55 | GAUGCCAUGAAAGCUUACA | 86 |
| | | | 56 | AUGCCAUGAAAGCUUACAU | 87 |
| | | | 57 | UGCCAUGAAAGCUUACAUC | 88 |
| | | | 58 | GCCAUGAAAGCUUACAUCA | 89 |
| | | | 59 | CCAUGAAAGCUUACAUCAA | 90 |
| | | | 60 | CAUGAAAGCUUACAUCAAC | 91 |
| | | | 61 | AUGAAAGCUUACAUCAACA | 92 |
| | | | 62 | UGAAAGCUUACAUCAACAA | 93 |
| | | | 63 | GAAAGCUUACAUCAACAAA | 94 |
| | | | 64 | AAAGCUUACAUCAACAAAG | 95 |
| | | | 65 | AAGCUUACAUCAACAAAGU | 96 |
| | | | 66 | AGCUUACAUCAACAAAGUA | 97 |
| | | | 67 | GCUUACAUCAACAAAGUAG | 98 |
| | | | 68 | CUUACAUCAACAAAGUAGA | 99 |
| | | | 69 | UUACAUCAACAAAGUAGAA | 100 |
| | | | 70 | UACAUCAACAAAGUAGAAG | 101 |
| | | | 71 | ACAUCAACAAAGUAGAAGA | 102 |
| | | | 72 | CAUCAACAAAGUAGAAGAG | 103 |
| | | | 73 | AUCAACAAAGUAGAAGAGC | 104 |
| | | | 74 | UCAACAAAGUAGAAGAGCU | 105 |
| | | | 75 | CAACAAAGUAGAAGAGCUA | 106 |
| | | | 76 | AACAAAGUAGAAGAGCUAA | 107 |
| | | | 77 | ACAAAGUAGAAGAGCUAAA | 108 |
| | | | 78 | CAAAGUAGAAGAGCUAAAG | 109 |
| | | | 79 | AAAGUAGAAGAGCUAAAGA | 110 |
| | | | 80 | AAGUAGAAGAGCUAAAGAA | 111 |
| | | | 81 | AGUAGAAGAGCUAAAGAAA | 112 |
| | | | 82 | GUAGAAGAGCUAAAGAAAA | 113 |
| | | | 83 | UAGAAGAGCUAAAGAAAAA | 114 |
| | | | 84 | AGAAGAGCUAAAGAAAAAA | 115 |
| | | | 85 | GAAGAGCUAAAGAAAAAAU | 116 |
| | | | 86 | AAGAGCUAAAGAkAAAAUA | 117 |
| | | | 87 | AGAGCUAAAGAkAAAAUAC | 118 |
| | | | 88 | GAGCUAAAGAAAAAUACG | 119 |

TABLE I-continued

Sequences Used For the Data of FIGS. 12-14

| FIG. | Accession # | Gene Name | Designation | siRNA Target Sequence | SEQ. ID NO. |
|---|---|---|---|---|---|
| | | | 89 | AGCUAAAGAAAAAAUACGG | 120 |
| | | | 90 | GCUAAAGAAAAAAUACGGG | 121 |
| 12B | | | | | |
| | NM_000633 | Bcl2 | Bcl2 2 | GAAGUACAUCCAUUAUAAG | 122 |
| | NM_002745 | MAPK1 | MAPK1 2 | AAACAGAUCUUUACAAGCU | 123 |
| | NM_006219 | PI3K Cb | PI3K Cb4 | UUUCAAGUGUCUCCUAAUA | 124 |
| | NM_001654 | ARaf1 | Raf1 2 | GCAAAGAACAUCAUCCAUA | 125 |
| | NM_002755 | MAP2K1 | MAP2K1 2 | GCAGAGAGAGCAGAUUUGA | 126 |
| | NM_000044 | AR | AR 3 | UCAAGGAACUCGAUCGUAU | 127 |
| | NM_001654 | ARaf1 | Raf1 3 | GACAUGAAAUCCAACAAUA | 128 |
| | NM_006219 | PI3K Cb | PI3K Cb2 | UCAAGUGUCUCCUAAUAUG | 129 |
| | NM_030662 | MAP2K2 | MAP2K2 1 | CAAAGACGAUGACUUCGAA | 130 |
| | NM_030662 | MAP2K2 | MAP2K2 4 | GGAAGCUGAUCCACCUUGA | 131 |
| | NM_002745 | MAPK1 | MAPK1 3 | CAAGAGGAUUGAAGUAGAA | 132 |
| | NM_002745 | MAPK1 | MAPK1 1 | CCAAAGCUCUGGACUUAUU | 133 |
| | NM_000633 | Bcl2 | Bcl2 3 | GUACGACAACCGGGAGAUA | 134 |
| | NM_000633 | Bcl2 | Bcl2 4 | AGAUAGUGAUGAAGUACAU | 135 |
| | NM_000633 | Bcl2 | Bcl2 1 | GGGAGAUAGUGAUGAAGUA | 136 |
| | NM_000044 | AR | AR 4 | GAAAUGAUUGCACUAUUGA | 137 |
| | NM_001654 | ARaf1 | Raf1 1 | GCACGGAGAUGUUGCAGUA | 138 |
| | NM_000348 | SRD5A2 | SRD5A2 1 | GCUACUAUCUGAUUUACUG | 139 |
| | NM_000044 | AR | AR 2 | CAAGGGAGGUUACACCAAA | 140 |
| | NM_002755 | MAP2K1 | MAP2K1 3 | GAGGUUCUCUGGAUCAAGU | 141 |
| | NM_002746 | MAPK3 | MAPK3 4 | GCUACACGCAGUUGCAGUA | 142 |
| | NM_002746 | MAPK3 | MAPK3 2 | AGACUGACCUGUACAAGUU | 143 |
| | NM_030662 | MAP2K2 | MAP2K2 2 | GAUCAGCAUUUGCAUGGAA | 144 |
| | NM_000044 | AR | AR-1 | GGAACUCGAUCGUAUCAUU | 145 |
| | NM_006219 | PI3K Cb | PI3KCb-1 | CGACAAGACUGCCGAGAGA | 146 |
| | NM_005178 | Bcl3 | Bcl3 2 | GAGCCUUACUGCCUUUGUA | 147 |
| | NM_006218 | PI3K Ca | PI3K Ca4 | CUGAAGAAAGCAUUGACUA | 148 |
| | NM_005178 | Bcl3 | Bcl3 3 | GGCCGGAGGCGCUUUACUA | 149 |
| | NM_002745 | MAPK1 | MAPK1 4 | GUACAGGGCUCCAGAAAUU | 150 |
| | NM_005178 | Bcl3 | Bcl3 4 | UCGACGCAGUGGACAUUAA | 151 |
| | NM_006218 | PI3K Ca | PI3K Ca2 | AACUAGAAGUAUGUUGCUA | 152 |
| | NM_002746 | MAPK3 | MAPK3 1 | GACCGGAUGUUAACCUUUA | 153 |
| | NM_000348 | SRD5A2 | SRD5A2 4 | UUGGGUGUCUUCUUAUUUA | 154 |
| | NM_006218 | PI3K Ca | PI3K Ca3 | AAUGGCUUUGAAUCUUUGG | 155 |

TABLE I-continued

Sequences Used For the Data of FIGS. 12-14

| FIG. | Accession # | Gene Name | Designation | siRNA Target Sequence | SEQ. ID NO. |
|---|---|---|---|---|---|
| | NM_002755 | MAP2K1 | MAP2K1 1 | GCACAUGGAUGGAGGUUCU | 156 |
| | NM_006219 | PI3K Cb | PI3K Cb3 | GGAUUCAGUUGGAGUGAUU | 157 |
| | NM_001654 | ARaf1 | Raf1 4 | CAAAGAACAUCAUCCAUAG | 158 |
| | NM_001047 | SRD5A1 | SRD5A1 3 | GAAAGCCUAUGCCACUGUU | 159 |
| | NM_000348 | SRD5A2 | SRD5A2 2 | GCUAUGCCCUGGCCACUUG | 160 |
| | NM_002755 | MAP2K1 | MAP2K1 4 | GAGCAGAUUUGAAGCAACU | 161 |
| | NM_001047 | SRD5A1 | SRD5A1 2 | UAACUGCAGCCAACUAUUU | 162 |
| | NM_006218 | PI3K Ca | PI3KCa-1 | AUGUUUACUACCAAAUGGA | 163 |
| | NM_030662 | MAP2K2 | MAP2K2 3 | UCCAGGAGUUUGUCAAUAA | 164 |
| | NM_001047 | SRD5A1 | SRD5A1-1 | GCAGAUACUUGAGCCAUUG | 165 |
| | NM_002746 | MAPK3 | MAPK3 3 | GAAACUACCUACAGUCUCU | 166 |
| | NM_001047 | SRD5A1 | SRD5A1 4 | CCGGAAAUUUGAAGAGUAU | 167 |
| | NM_005178 | Bcl3 | Bcl3 1 | GAACACCGAGUGCCAAGAA | 168 |
| | NM_000348 | SRD5A2 | SRD5A2 3 | GGACAUUUGUGUACUCACU | 169 |
| 12 C | | | | | |
| | NM_002755 | MAP2K1 | MAP2K1 1 | GCACAUGGAUGGAGGUUCU | 170 |
| | NM_002755 | MAP2K1 | MAP2K1 2 | GCAGAGAGAGCAGAUUUGA | 171 |
| | NM_002755 | MAP2K1 | MAP2K1 3 | GAGGUUCUCUGGAUCAAGU | 172 |
| | NM_002755 | MAP2K1 | MAP2K1 4 | GAGCAGAUUUGAAGCAACU | 173 |
| | NM_030662 | MAP2K2 | MAP2K2 1 | CAAAGACGAUGACUUCGAA | 174 |
| | NM_030662 | MAP2K2 | MAP2K2 2 | GAUCAGCAUUUGCAUGGAA | 175 |
| | NM_030662 | MAP2K2 | MAP2K2 3 | UCCAGGAGUUUGUCAAUAA | 176 |
| | NM_030662 | MAP2K2 | MAP2K2 4 | GGAAGCUGAUCCACCUUGA | 177 |
| 12 D | | | | | |
| | NM_030662 | MAP2K2 | MAP2K2 3 | UCCAGGAGUUUGUCAAUAA | 178 |
| | NM_001047 | SRD5A1 | SRD5A1 1 | GCAGAUACUUGAGCCAUUG | 179 |
| | NM_001047 | SRD5A1 | SRD5A1 3 | CCGGAAAUUUGAAGAGUAU | 180 |
| | NM_000348 | SRD5A2 | SRD5A2 3 | GGACAUUUGUGUACUCACU | 181 |
| 13A | | | | | |
| | NM_005990 | STK10 | | GAAACGAGAUUCCUUCAUC | 182 |
| | AY406545 | MADH6 | | CAAGAUCGGUUUUGGCAUA | 183 |
| | NM_170679 | SKP1A | | CAAACAAUCUGUGACUAUU | 184 |
| | NM_002257 | KLK1 | | CAACUUGUUUGACGACGAA | 185 |
| | NM_000942 | PPIB | | GAAAGGAUUUGGCUACAAA | 186 |
| | NM_005083 | U2AF1L1 | | GAGCAUGUUUACAACGUUU | 187 |
| | NM_000942 | PPIB | | GGAAAGACUGUUCCAAAAA | 188 |
| | NM_006622 | SNK | | ACAUUUACAUUCUCUUGGA | 189 |

TABLE I-continued

Sequences Used For the Data of FIGS. 12-14

| FIG. | Accession # | Gene Name | Designation | siRNA Target Sequence | SEQ. ID NO. |
|---|---|---|---|---|---|
| | NM_000942 | PPIB | | GAAAGAGCAUCUACGGUGA | 190 |
| | NM_005379 | MYO1A | | ACAAGGAGAUUUAUACCUA | 191 |
| | NM_002620 | PF4V1 | | AGGAACAUUUGGAGAGUUA | 192 |
| | NM_005627 | Sgk1 | | CAUCGUUUAUAGAGACUUA | 193 |
| | NM_022550 | XRCC4 | | GAAAGUAAGCAGAAUCUAU | 194 |
| | AY313906 | SARS SEP | | AACCAACGGUUUACGUCUA | 195 |
| | NM_181523 | PIK3R1 | | GAAAGACAAGAGACCAAUA | 196 |
| | NM_020183 | ARNTL2 | | CAACAGCGAUUUUAGGAUA | 197 |
| | NM_018131 | C10ORF3 | | GGAAACAGCUGCUCAUUCA | 198 |
| | NM_139025 | ADAMTS13 | | ACAUUUGGCUGUGAUGGUA | 199 |
| | NM_005767 | P2RY5 | | GAAACUACAACUUACAUGA | 200 |
| | NM_147199 | MRGX1 | | GAUGAUGUUUUCCUACUUU | 201 |
| | NM_001892 | CSNK1A1 | | AGAAUUUGCGAUGUACUUA | 202 |
| | NM_006930 | SKP1A | | AGGUUUGCUUGAUGUUACA | 203 |
| | M15077 | PPYLUC | | CGAAAGGUCUUACCGGAAA | 204 |
| | NM_006257 | PRKCQ | | CAAAGAGUAUGUCGAAUCA | 205 |
| | NM_018131 | C10ORF3 | | AAGGAAAGCUGACUGAUAA | 206 |
| | NM_013391 | DMGDH | | CAUCAAAGCUGCCAUGGAA | 207 |
| | BC025733 | FADD | | CAGCAUUUAACGUCAUAUG | 208 |
| | NM_005541 | INPP5D | | AUUGCGUUUACACUUACAG | 209 |
| | NM_006395 | GSA7 | | GAUCAAAGGUUUUCACUAA | 210 |
| | AC146999 | Human Herpes-virus 5 | | CAAACCAGCGCGCUAAUGA | 211 |
| | NM_153202 | ADAM33 | | CAAACAGCGUCUCCUGGAA | 212 |
| | NM_005508 | CCR4 | | GAAAGCAUAUACAGCAAUU | 213 |
| | NM_002605 | PDE8A | | CAAAGAAGAUAACCAAUGU | 214 |
| | NM_000455 | STK11 | | GAAACAUCCUCCGGCUGAA | 215 |
| | AF493910 | RALA | | GAGCAGAUUUUAAGAGUAA | 216 |
| | NM_012184 | FOXD4L1 | | GGACAAUUUUGCAGCAACA | 217 |
| | NM_001273 | CHD4 | | CAAAGGUGCUGCUGAUGUA | 218 |
| | NM_002434 | MPG | | ACAUCAUUUACGGCAUGUA | 219 |
| 13B | | | | | |
| | NM_004429 | EFNB1 | | CCACACCGCUGGCCAAGAA | 220 |
| | NM_002717 | PPP2R2A | | UAUCAAGCCUGCCAAUAUG | 221 |
| | XM_110671 | M11 | | UCAUAAGCCAUCUUCUAA | 222 |
| | NM_001282 | AP2B1 | | GAGCUAAUCUGCCACAUUG | 223 |
| | NM_001846 | COL4A2 | | CGAAGGCGGUGGCCAAUCA | 224 |
| | AF100153 | CNK | | GCACAUCCGUUGGCCAUCA | 225 |

TABLE I-continued

Sequences Used For the Data of FIGS. 12-14

| FIG. | Accession # | Gene Name | Designation | siRNA Target Sequence | SEQ. ID NO. |
|---|---|---|---|---|---|
| | NM_001136 | AGER | | GCCAGGCAAUGAACAGGAA | 226 |
| | NM_007122 | USF1 | | GGAAGCCAGCGCUCAAUUG | 227 |
| | NM_001136 | AGER | | GCGAGCCACUGGUGCUGAA | 228 |
| | NM_018653 | GPRC5C | | CCACCUCCGUUGCCAUAUG | 229 |
| | NM_001431 | EPB41L2 | | GAAGGACUCUAGCCAGUUA | 230 |
| | NM_000119 | EPB42 | | GACCACACCUUGCCAUCAA | 231 |
| | NM_004448 | ERBB2 | | GCAGUUACCAGUGCCAAUA | 232 |
| | NM_005971 | FXYD3 | | GGACGCCAAUGACCUAGAA | 233 |
| | NM_003494 | DYSF | | GAACUAUGCUGCCAUGAAG | 234 |
| | NM_013391 | DMGDH | | CAUCAAAGCUGCCAUGGAA | 235 |
| | NM_022353 | OSGEPL1 | | AGACAUUGCUGCCACAGUA | 236 |
| | NM_003367 | USF2 | | GGCCAGUUCUACGUCAUGA | 237 |
| | NM_172390 | NFATc1 | | GCCAGGAGCUGAACAUUAA | 238 |
| 13C | | | | | |
| | NM_005378 | MYCN | | CACGUCCGCUCAAGAGUGU | 239 |
| | NM_000147 | FUCA1 | | UAACAAUGCUGGGAAUUCA | 240 |
| | NM_003566 | EFA1 | | AGACAGAGCUUGAGAAUAA | 241 |
| | NM_004707 | APG12L | | UGUUGCAGCUUCCUACUUC | 242 |
| | NM_003918 | GYG2 | | GACCAAGGCUUACUGAAUA | 243 |
| | NM_004462 | FDFT1 | | CAUAGUUGGUGAAGACAUA | 244 |
| | XM_291277 | SgK223 | | GAGCUCCACUUCAAUGAGA | 245 |
| | NM_004573 | PLC beta 2 | | GAACAGAAGUUACGUUGUC | 246 |
| | NM_003955 | SOCS3 | | CACCUGGACUCCUAUGAGA | 247 |
| | NM_203330 | CD59 | | CUACAACUGUCCUAACCCA | 248 |
| | NM_002377 | MAS1 | | CUACACAAUUGUCACAUUA | 249 |
| | NM_153326 | AKR1A1 | | UGAGGAGGCUGAGUAAUUC | 250 |
| | NM_001749 | CAPNS1 | | CCACAGAACUCAUGAACAU | 251 |
| | NM_016735 | LIMK1 | | UCAACUUCAUCACUGAGUA | 252 |
| | NM_002393 | MDM4 | | CGUCAGAGCUUCUCCGUAA | 253 |
| | NM_021969 | NR0B2 | | CGUAGCCGCUGCCUAUGUA | 254 |
| | NM_002741 | PRKCL1 | | ACAGCGACGUGUUCUCUGA | 255 |
| | NM_014452 | TNFRSF21 | | CAGAAGGCCUCGAAUCUCA | 256 |
| | NM_139343 | BIN1 | | GCUCAAGGCUGGUGAUGUG | 257 |
| | NM_001003945 | ALAD | | GAUGCAUACAGCCUAUCA | 258 |
| | NM_013315 | TPTE | | UUUAUUCGAUUCCUCGUUA | 259 |
| | NM_024560 | FLJ21963 | | UCGAGUGGAUGAUGUAAUA | 260 |
| | L07868 | ERBB4 | | AGGAUCUGCAUAGAGUCUU | 261 |

TABLE I-continued

Sequences Used For the Data of FIGS. 12-14

| FIG. | Accession # | Gene Name | Designation | siRNA Target Sequence | SEQ. ID NO. |
|---|---|---|---|---|---|
| | NM_001003809 | DLGAP1 | | CAACCUGGAUGGUGACAUG | 262 |
| | NM_005232 | EPHA1 | | UGAAGAACGGUACCAGAUG | 263 |
| | NM_003818 | CDS2 | | GUGAGACAGUGACGGAUUA | 264 |
| | NM_153675 | FOXA2 | | ACGAACAGGUGAUGCACUA | 265 |
| | XM_496495 | GGT2 | | AAUAAUGAAUGGACGACUU | 266 |
| | NM_020676 | ABHD6 | | GAUGACCUGUCCAUAGAUG | 267 |
| | NM_000487 | ARSA | | UCUAUGACCUGUCCAAGGA | 268 |
| | AF348074 | NAT2 | | AUACAGAUCUGGUCGAGUU | 269 |
| | U02388 | CYP4F2 | | CAUAUUGACUUCCUGUAUU | 270 |
| 14 A-14 I | | | | | |
| | | EGFP | | GCAAAGACCCCAACGAGAA | 271 |
| | NM_012154 | eIF2C2 | | GCACGGAAGUCCAUCUGAA | 272 |
| | | | | GCAGGACAAAGAUGUAUUA | 273 |
| | | | | GGGUCUGUGGUGAUAAAUA | 274 |
| | | | | GUAUGAGAACCCAAUGUCA | 275 |
| | NM_012154e | IF2C2 | | GCACGGAAGUCCAUCUGAA | 276 |
| | | | | GCAGGACAAAGAUGUAUUA | 277 |
| | | | | GGGUCUGUGGUGAUAAAUA | 278 |
| | | | | GUAUGAGAACCCAAUGUCA | 279 |
| 14J | NM_006218 | PI3K Ca | PI3KCa-1 | AUGUUUACUACCAAAUGGA | 280 |
| | NM_001047 | SRD5A1 | SRD5A1 2 | UAACUGCAGCCAACUAUUU | 281 |
| | NM_030662 | MAP2K2 | MAP2K2 3 | UCCAGGAGUUUGUCAAUAA | 282 |
| | NM_001047 | SRD5A1 | SRD5A1-1 | GCAGAUACUUGAGCCAUUG | 283 |
| | NM_001047 | SRD5A1 | SRD5A1 4 | CCGGAAAUUUGAAGAGUAU | 284 |
| 14K | | | | | |
| | NM_006218 | PI3K Ca | PI3K Ca1 | AUGUUUACUACCAAAUGGA | 285 |
| | NM_001047 | SRD5A1 | SRD5A1 2 | UAACUGCAGCCAACUAUUU | 286 |
| | NM_030662 | MAP2K2 | MAP2K2 3 | UCCAGGAGUUUGUCAAUAA | 287 |
| | NM_001047 | SRD5A1 | SRD5A1 1 | GCAGAUACUUGAGCCAUUG | 288 |
| | NM_001047 | SRD5A1 | SRD5A1 4 | CCGGAAAUUUGAAGAGUAU | 289 |
| | NM_000348 | SRD5A2 | SRD5A2 3 | GGACAUUUGUGUACUCACU | 290 |
| | M15077 | PPYLUC | | UGUUUGUGGACGAAGUACC | 291 |
| | BC020308 | GAPDH | | CCUGGCCAAGGUCAUCCAU | 292 |
| | NM_000942 | PPIB | | GAGAAAGGAUUUGGCUACA | 293 |

TABLE I-continued

Sequences Used For the Data of FIGS. 12-14

| FIG. | Accession # | Gene Name | Designation | siRNA Target Sequence | SEQ. ID NO. |
|---|---|---|---|---|---|
| 14L | | | | | |
| | NM_001047 | SRD5A1 | SRD5A12 | UAACUGCAGCCAACUAUUU | 294 |
| | NM_030662 | MAP2K2 | MAP2K23 | UCCAGGAGUUUGUCAAUAA | 295 |
| | NM_001047 | SRD5A1 | SRD5A11 | GCAGAUACUUGAGCCAUUG | 296 |
| | NM_001047 | SRD5A1 | SRD5A14 | CCGGAAAUUUGAAGAGUAU | 297 |
| | NM_000348 | SRD5A2 | SRD5A23 | GGACAUUUGUGUACUCACU | 298 |
| | NM_001273 | CHD4 | | CAAAGGUGCUGCUGAUGUA | 299 |
| | NM_002605 | PDE8A | | CAAAGAAGAUAACCAAUGU | 300 |
| | NM_000455 | STK11 | | GAAACAUCCUCCGGCUGAA | 301 |

What is claimed is:

1. A functional double stranded polyribonucleotide for silencing a target gene, said double stranded polyribonucleotide comprising:
   a. a sense strand comprising a sense region, wherein said sense region comprises:
      i. a first 5' sense nucleotide having a first 2'-O-alkyl modification; and
      ii. a second 5' sense nucleotide having a second 2'-O-alkyl modification; and
   b. an antisense strand comprising an antisense region, wherein said antisense region comprises:
      i. a first 5' antisense nucleotide having a third 2'-O-alkyl modification and a 5' terminal phosphate; and
      ii. a second 5' antisense nucleotide having a fourth 2'-O-alkyl modification;
   wherein said sense region and said antisense region form a duplex of 18-24 base pairs of nucleotides that has at least 80% complementarity over the range of the duplex, and within said duplex said first 5' sense nucleotide is the 5' most nucleotide of the sense strand, said second 5' sense nucleotide is immediately adjacent to and downstream of the first 5' sense nucleotide, said first 5' antisense nucleotide is the 5' most nucleotide of the antisense strand and said second 5' antisense nucleotide is immediately adjacent to and downstream of the first 5' antisense nucleotide, wherein all nucleotides of each strand of said double stranded polyribonucleotide other than said first 5' sense nucleotide, said second 5' sense nucleotide, said first 5' antisense nucleotide, and said second 5' antisense nucleotide comprises a 2'-OH, and wherein said double stranded polyribonucleotide is capable of silencing a target gene with reduced off-target gene silencing.

2. The double stranded polyribonucleotide of claim 1, wherein said first 2'-O-alkyl modification, second 2'-O-alkyl modification, third 2'-O-alkyl modification, and fourth 2'-O-alkyl modification are independently selected from the group consisting of 2'-O-methyl, 2'-O-ethyl, 2'-O-propyl, 2'-O-isopropyl, 2'-O-butyl, 2'-O-isobutyl, 2'-O-ethyl-O-methyl, and 2'-O-ethyl-OH.

3. The double stranded polyribonucleotide of claim 2, wherein said first 2'-O-alkyl modification comprises a 2'-O-methyl, said second 2'-O-alkyl modification comprises a 2'-O-methyl, said third 2'-O-alkyl modification comprises a 2'-O-methyl, and said fourth 2'-O-alkyl modification comprises a 2'-O-methyl.

4. The double stranded polyribonucleotide of claim 1, further comprising a 3' overhang, and said 3' overhang is 1 to 6 bases on at least one of said sense strand or said antisense strand.

5. The double stranded polyribonucleotide of claim 4, wherein said 3' overhang is 2 bases on at least one of said sense strand or said antisense strand.

6. The double stranded polyribonucleotide of claim 1, wherein only said first 5' antisense nucleotide has a 5' terminal phosphate.

7. The double stranded polyribonucleotide of claim 1, wherein said double stranded polyribonucleotide has reduced off-target gene silencing activity compared to a double stranded polyribonucleotide having the same nucleotide sequence as said double stranded polyribonucleotide, but does not contain 2'-O-alkyl modifications in said sense and antisense strands.

8. The double stranded polyribonucleotide of claim 1, wherein said double stranded polyribonucleotide has reduced off-target gene silencing activity compared to a double stranded polyribonucleotide having the same nucleotide sequence as said double stranded polyribonucleotide, but does not contain 2'-O-alkyl modifications in said antisense strand.

9. The double stranded polyribonucleotide of claim 1, further comprising at least one conjugate molecule coupled to the 3' terminus of the sense or antisense strand.

* * * * *